US008367619B2

(12) United States Patent
Wight et al.

(10) Patent No.: US 8,367,619 B2
(45) Date of Patent: Feb. 5, 2013

(54) METHODS FOR PROMOTING ELASTOGENESIS AND ELASTIN FIBER FORMATION BY INCREASING TROPOELASTIN EXPRESSION

(75) Inventors: Thomas N. Wight, Seattle, WA (US); Mervyn Merrilees, Auckland (NZ)

(73) Assignee: Benaroya Research Institute at Virginia Mason, Seattle, WA (US)

( * ) Notice: Subject to any disclaimer, the term of this patent is extended or adjusted under 35 U.S.C. 154(b) by 93 days.

(21) Appl. No.: 12/526,625

(22) PCT Filed: Feb. 7, 2008

(86) PCT No.: PCT/US2008/053341
§ 371 (c)(1),
(2), (4) Date: Mar. 26, 2010

(87) PCT Pub. No.: WO2008/100789
PCT Pub. Date: Aug. 21, 2008

(65) Prior Publication Data
US 2010/0197563 A1  Aug. 5, 2010

Related U.S. Application Data

(60) Provisional application No. 60/901,951, filed on Feb. 16, 2007.

(51) Int. Cl.
| | |
|---|---|
| *A61K 38/16* | (2006.01) |
| *A61K 38/00* | (2006.01) |
| *C12N 5/00* | (2006.01) |
| *C12N 5/02* | (2006.01) |
| *A61P 43/00* | (2006.01) |
| *A61P 19/00* | (2006.01) |
| *A61P 17/00* | (2006.01) |

(52) U.S. Cl. ..... 514/21.2; 435/375; 514/16.5; 514/17.1; 514/18.6

(58) Field of Classification Search .......... None
See application file for complete search history.

(56) References Cited

U.S. PATENT DOCUMENTS

| | | | | |
|---|---|---|---|---|
| 6,864,236 | B1 | 3/2005 | Fallon et al. | 514/12 |
| 7,816,335 | B2 * | 10/2010 | Wight et al. | 514/44 R |
| 2004/0146539 | A1 | 7/2004 | Gupta | 424/401 |
| 2004/0213762 | A1 | 10/2004 | Wight et al. | 424/93.2 |

FOREIGN PATENT DOCUMENTS

| | | |
|---|---|---|
| CA | 2 518 794 | 9/2003 |
| CA | 2 520 057 | 10/2004 |
| FR | 2 847 816 | 6/2004 |
| JP | 2004-250395 | 9/2004 |
| WO | 99/45942 | 9/1999 |
| WO | WO01/79284 | * 10/2001 |
| WO | 01/91700 | 12/2001 |
| WO | 2004/012665 | 2/2004 |
| WO | 2005/082386 | 9/2005 |

OTHER PUBLICATIONS

Bork P. Genome Research 10:398-400, 2000.*
Bork P. Trends in Genetics 12(10):425-427, Oct. 1996.*
Brenner SE. Trends in Genetics 15(4):132-133, Apr. 1999.*
Doerks T, et al. Trends in Genetics 14(6):248-250, Jun. 1998.*
Skolnick J and Fetrow JS. Trends in Biotech 18(1):34-39, 2000.*
Smith TF and Zhang X. Nature Biotechnology 15:1222-1223, 1997.*
Cunningham BC and Wells JA. Science 244:1081-1085, Jun. 2, 1989.*
Barry et al., "Hyaluronan-binding region of aggrecan from pig laryngeal cartilage," *Biochem. J.*, 286:761-769, 1992.
Barta et al., "Evolution of the hyaluronan-binding module of link protein," *Biochem. J.*, 292:947-949, 1993.
Boyd et al., "Increased Elastin mRNA Levels Associated with Surgically Induced Intimal Injury," *Connective Tissue Research*, 18:65-78, 1988.
Brissett et al., "The protein fold of the hyaluronate-binding proteoglycan tandem repeat domain of link protein, aggrecan and CD44 is similar to that of the C-type lectin superfamily," *FEBS Letters*, 388:211-216, 1996.
Caterson et al., "Monoclonal Antibodies as Probes for Determining the Microheterogeneity of the Link Proteins of Cartilage Proteoglycan," *The Journal of Biological Chemistry*, 260(19):11348-11356, 1985.
Chu et al., "Cloning and characterization of five overlapping cDNAs specific for the human proα1(I) collagen chain," *Nucleic Acids Research*, 10(19):5925-5934, 1982.
Fisher et al., "Human biglycan gene. Putative promoter, intron-exon junctions, and chromosomal localization," *The Journal of Biological Chemistry*, 266(22):14371-14377, 1991.
Fisher et al., "Antisera and cDNA probes to human and certain animal model bone matrix noncollagenous proteins," *Acta Orthop Scand*, 66(Suppl. 266):61-65, 1995.
Genbank Accession No. GI:3309591, Apr. 29, 1999.
Grande-Allen et al., "Glycosaminoglycans and proteoglycans in normal mitral valve leaflets and chordae: association with regions of tensile and compressive loading," *Glycobiology*, 14(7):621-633, 2004.
Hinek et al., "Impaired Elastin Fiber Assembly Related to Reduced 67-kD Elastin-binding Protein in Fetal Lamb Ductus Arteriosus and in Cultured Aortic Smooth Muscle Cells Treated with Chondroitin Sulfate," *J. Clin. Invest.*, 88:2083-2094, 1991.
Hinek et al., "The 67-kD Elastin/Laminin-binding Protein Is Related to an Enzymatically Inactive, Alternatively Spliced Form of β-Galactosidase," *J. Clin. Invest.*, 91:1198-1205, 1993.
Hinek, "Nature and the Multiple Functions of the 67-kD Elastin-/Laminin Binding Protein," *Cell Adhesion and Communication*, 2:185-193, 1994.
Hinek, "Biological Roles of the Non-Integrin Elastin/Laminin Receptor," *Biol. Chem.*, 377:471-480, 1996.
Hinek, "Impaired Elastogenesis in Hurler Disease," *American Journal of Pathology*, 156(3):925-938, 2000.

(Continued)

*Primary Examiner* — Robert Landsman
(74) *Attorney, Agent, or Firm* — Seed IP Law Group PLLC

(57) ABSTRACT

Compositions and methods are provided for promoting elastin fiber formation (elastogenesis) in a cell, including methods that comprise contacting a cell that is capable of elastogenesis with (i) a mutated biglycan polypeptide that lacks chondroitin sulphate proteoglycan chains, (ii) a versican V3 isoform polypeptide that lacks most or all of the polypeptide regions encoded by one or more of exons 4, 5 or 6 or by exons 9-10 or 11-13, and/or with (iii) metastatin.

20 Claims, 10 Drawing Sheets

OTHER PUBLICATIONS

Figure 1:
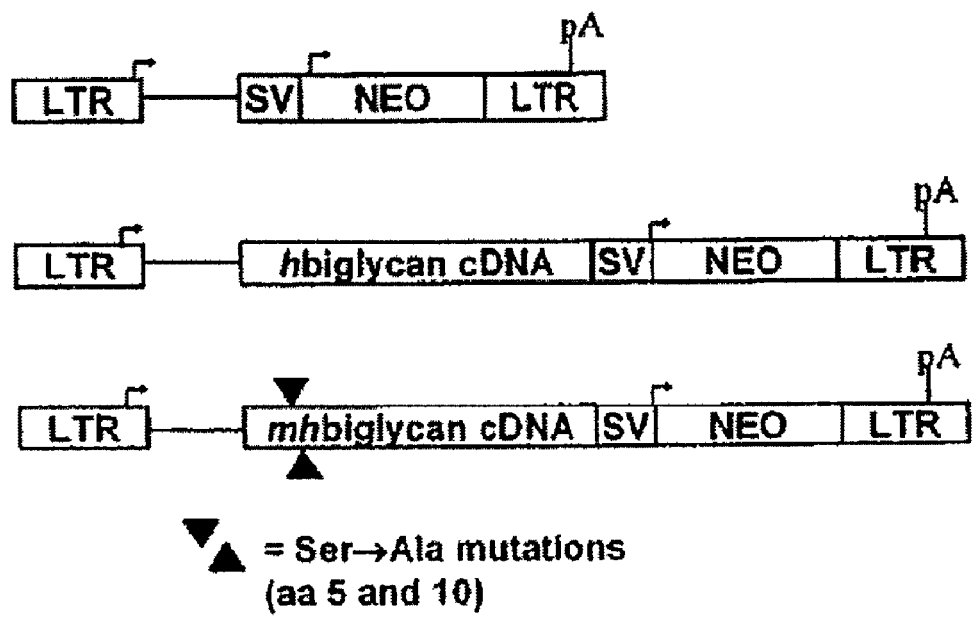

Hinek et al., "Decreased Elastin Deposition and High Proliferation of Fibroblasts from Costello Syndrome Are Related to Functional Deficiency in the 67-kD Elastin-Binding Protein," *Am. J. Hum. Genet.*, 66:859-872, 2000.

Hinek et al., "Impaired Elastic-Fiber Assembly by Fibroblasts from Patients with Either Morquio B Disease or Infantile GM1-Gangliosidosis Is Linked to Deficiency in the 67-kD Spliced Variant of β-Galactosidase," *Am. J. Hum. Genet.*, 67:23-36, 2000.

Hinek et al., "Impaired elastogenesis and development of the non-atherosclerotic occlusive arterial diseases in children," *Ann. Diagnost. Pediatr. Pathol.*, 7:7-14, 2003.

Hinek et al., "Retrovirally Mediated Overexpression of Versican V3 Reverses Impaired Elastogenesis and Heightened Proliferation Exhibited by Fibroblasts from Costello Syndrome and Hurler Disease Patients," *American Journal of Pathology*, 164(1):119-131, 2004.

Huang et al., "Inhibition of Versican Synthesis by Antisense Alters Smooth Muscle Cell Phenotype and Induces Elastic Fiber Formation In Vitro and in Neointima After Vessel Injury," *Circulation Research*, 98(3):370-377, 2006.

Itabashi et al., "Interaction Between Proteoglycans and α-Elastin in Construction of Extracellular Matrix of Human Yellow Ligament," *Connective Tissue Research*, 46:67-73, 2005.

Jung et al., "Tropoelastin and Elastin Degradation Products Promote Proliferation of Human Astrocytoma Cell Lines," *Journal of Neuropathology and Experimental Neurology*, 57(5):439-448, 1998.

Kelleher et al., *Current Topics in Developmental Biology*, vol. 62, Elsevier Inc., St. Louis, Missouri, 2004, Chapter 6, "Vascular Extracellular Matrix and Aortic Development," pp. 153-188.

Kinsella et al., "The Regulated Synthesis of Versican, Decorin, and Biglycan: Extracellular Matrix Proteoglycans That Influence Cellular Phenotype," *Critical Reviews™ in Eukaryotic Gene Expression*, 14(3):203-234, 2004.

Kirwan et al., "Influence of cyclical mechanical strain on extracellular matrix gene expression in human lamina cribrosa cells in vitro," *Molecular Vision*, 11:798-810, 2005.

Kohda et al., "Solution Structure of the Link Module: A Hyaluronan-Binding Domain Involved in Extracellular Matrix Stability and Cell Migration," *Cell*, 86:767-775, 1996.

Kolodgie et al., "Differential Accumulation of Proteoglycans and Hyaluronan in Culprit Lesions. Insights Into Plaque Erosion," *Arteriosclerosis, Thrombosis, and Vascular Biology*, 22:1642-1648, 2002.

Liu et al., "Metastatin: A Hyaluronan-binding Complex from Cartilage That Inhibits Tumor Growth," *Cancer Research*, 61:1022-1028, 2001.

Liu et al., "Failure of Elastic Fiber Homeostasis Leads to Pelvic Floor Disorders," *American Journal of Pathology*, 168(2):519-528, 2006.

Merrilees et al., "Retrovirally Mediated Overexpression of Versican V3 by Arterial Smooth Muscle Cells Induces Tropoelastin Synthesis and Elastic Fiber Formation In Vitro and In Neointima After Vascular Injury," *Circulation Research*, 90:481-487, 2002.

Merrilees et al., "Matrix proteoglycans and remodeling of interstitial lung tissue in lymphangioleiomyomatosis," *Journal of Pathology*, 203:653-660, 2004.

Mochizuki et al., "Signaling Pathways Transduced through the Elastin Receptor Facilitate Proliferation of Arterial Smooth Muscle Cells," *The Journal of Biological Chemistry*, 277(47):44854-44863, 2002.

Nikkari et al., "Smooth Muscle Cell Expression of Extracellular Matrix Genes after Arterial Injury," *American Journal of Pathology*, 144(6):1348-1356, 1994.

Peach et al., "Identification of Hyaluronic Acid Binding Sites in the Extracellular Domain of CD44," *The Journal of Cell Biology*, 122(1):257-264, 1993.

Reinboth et al., "Developmental expression of dermatan sulfate proteoglycans in the elastic bovine nuchal ligament," *Matrix Biology*, 19:149-162, 2000.

Reinboth et al., "Molecular Interactions of Biglycan and Decorin with Elastic Fiber Components," *The Journal of Biological Chemistry*, 277(6):3950-3957, 2002.

Robb et al., "Characterization of an In Vitro Model of Elastic Fiber Assembly," *Molecular Biology of the Cell*, 10:3595-3605, 1999.

Schaefer et al., "Regulation of Fibrillin-1 by Biglycan and Decorin Is Important for Tissue Preservation in the Kidney During Pressure-Induced Injury," *American Journal of Pathology*, 165(2):383-396, 2004.

Schwarz et al., "Biosynthesis and Properties of a Further Member of the Small Chondroitin/Dermatan Sulfate Proteoglycan Family," *The Journal of Biological Chemistry*, 265(35):22023-22028, 1990.

Shimizu-Hirota et al., "Extracellular Matrix Glycoprotein Biglycan Enhances Vascular Smooth Muscle Cell Proliferation and Migration," *Circulation Research*, 94:1067-1074, 2004.

Stanescu, "The Small Proteoglycans of Cartilage Matrix," *Seminars in Arthritis and Rheumatism*, 20(3), Suppl. 1:51-64, 1990.

Starcher et al., "Elastin Defects in the Lungs of Avian and Murine Models of Homocysteinemia," *Experimental Lung Research*, 31:873-885, 2005.

Theocharis et al., "Decreased biglycan expression and differential decorin localization in human abdominal aortic aneurysms," *Atherosclerosis*, 165:221-230, 2002.

Tufvesson et al., "Biglycan isoforms with differences in polysaccharide substitution and core protein in human lung fibroblasts," *Eur. J. Biochem.*, 269:3688-3696, 2002.

Urbán et al., "Connection between Elastin Haploinsufficiency and Increased Cell Proliferation in Patients with Supravalvular Aortic Stenosis and Williams-Beuren Syndrome," *Am. J. Hum. Genet.*, 71:30-44, 2002.

Wight, "Versican: a versatile extracellular matrix proteoglycan in cell biology," *Current Opinion in Cell Biology*, 14:617-623, 2002.

Wight, *Atherothrombosis and Coronary Artery Disease*, Lippincott Williams and Wilkins, Philadelphia, PA, 2004, Chapter 29, "The Vascular Extracellular Matrix," pp. 421-437.

Wight et al., "Proteoglycans in Atherosclerosis and Restenosis: Key Roles for Versican," *Circulation Research*, 94:1158-1167, 2004.

Yao et al., "Identification of the Proteoglycan Versican in Aorta and Smooth Muscle Cells by DNA Sequence Analysis, in Situ Hybridization and Immunohistochemistry," *Matrix Biology*, 14:213-225, 1994.

Zimmermann et al., "Versican Is Expressed in the Proliferating Zone in the Epidermis and in Association with the Elastic Network of the Dermis," *The Journal of Cell Biology*, 124(5):817-825, 1994.

* cited by examiner

METHODS FOR PROMOTING ELASTOGENESIS AND ELASTIN FIBER FORMATION BY INCREASING TROPOELASTIN EXPRESSION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 140160_401USPC_SEQUENCE_LISTING.txt. The text file is 93 KB, was created on Mar. 26, 2010 and is being submitted electronically via EFS-Web.

BACKGROUND OF THE INVENTION

1. Field of the Invention

The present invention relates generally to biomedical compositions and methods for treating diseases, disorders and conditions affecting connective tissues. In particular, the present invention provides compositions and methods for enhancing elastic fiber content by promoting molecular mechanisms of elastogenesis.

2. Description of the Related Art

The extracellular matrix (ECM) plays an important role in the development and maintenance of vertebrate tissues, including the organization of various ECM components to provide structurally and functionally significant connective tissue compartments (reviewed in e.g., Hay, 1981 *J. Cell Biol.* 91:205s; Dallas et al., 2006 *Curr. Top. Dev. Biol.* 75:1; Ushiki, 2002 *Arch. Histol. Cytol.* 65:109). An important but incompletely characterized component of the ECM comprises the elastic fibers, a system of microfibrils that contains the protein elastin and other polypeptides in a framework that confers elasticity and resilience to selected tissues, including blood vessels, cardiac tissues including heart valves, lung, gastrointestinal and urogenital tracts, cartilage, ligaments, tendons and skin (Kielty et al., 2002 *J. Cell Sci.* 115: 2817; Cleary and Gibson, 1996 in *Extracellular Matrix* (Comper, W. D. ed.) Vol. 2, pp. 95-140, Harwood Academic Publishers, Amsterdam; Mecham and Heuser, 1991 in *Cell Biology of the Extracellular Matrix* (Hay, E. D., ed.) 2nd Ed., pp. 79-109, Plenum Publishing Corp., New York; Pasquali-Ronchetti et al., 1997 *Microsc. Res. Tech.* 38:428).

While many ECM components are synthesized throughout the lifetimes of most vertebrates, elastic fiber biosynthesis, or elastogenesis, takes place largely in developing tissues (Davis, 1993 *Histochem.* 100:17) with little or no de novo elastic fiber synthesis being seen in mature tissues. As such, the elastic fiber compartment of the ECM is not replenished following elastic fiber degradation due to aging or disease, or subsequent to tissue damage incurred in the course of injury, surgery or other clinical insults. The resultant loss of tissue elasticity and resiliency may exacerbate the disease, for example, by impairing the physiological function of the affected tissue and/or predisposing the afflicted individual to further tissue damage. The benefits of a functional elastic fiber system in an individual may thus be compromised by disease and/or related sequelae, for instance, by aneurysms, restenosis lesions, emphysema, or Marian syndrome, by skin wounds or aging-associated damage such as skin wrinkling, and/or by genetic defects linked to the elastin gene (see, e.g., Robb et al., 1999 *Mol. Biol. Cell* 10:3595 and references cited therein).

As known in the art, certain naturally occurring cell surface glycoconjugates act as elastogenic inhibitors by binding to the cell surface elastin binding protein (EBP) and disrupting EBP elastogenic activities. For example, several recent studies have highlighted the reciprocal relationship between elastogenesis and matrix proteoglycan content of tissues (e.g., Wight and Merrilees, 2004 *Circ. Res.* 94:1158; Hinek et al., 1991 *J. Clin. Invest.* 88:2083). Elastic fibers are generally absent or depleted in matrices rich in chondroitin sulphate (CS)-containing proteoglycans, and correspondingly increased in matrices depleted of CS proteoglycans (Kolodgie et al., 2002 *Arterioscler. Thromb. Vasc. Biol.* 22:1642-1648). Several lines of evidence point to the premature detachment of the elastin binding protein (EBP) from the cell surface as the mechanism by which the assembly of elastic fibers is disrupted (Hinek et al., 2000 *Am. J. Hum. Genet.* 66:859-872). There is compelling evidence that this detachment is due to the high concentration CS-containing proteoglycans, notably versican, found in pericellular coats of matrix rich tissues (Huang et al., 2006 *Circ. Res.* 98:370). EBP is an inactive splice variant of β galactosidase that binds both tropoleastin monomers and galactosugars such as CS (e.g., Hinek et al., 1993 *J. Clin. Invest.* 91:1198). Premature release of EBP from the cell surface occurs when the binding pocket for galactosugars is occupied (Hinek et al., 1991 *J. Clin. Invest.* 88:2083).

Proteoglycan rich matrices usually contain two major proteoglycans, versican and biglycan. (For versican see, e.g., Wight and Merrilees, 2004 *Circ. Res.* 94:1158; Wight, 2002 *Curr. Opin. Cell Biol.* 14:617; Yao et al., 1994 *Matrix Biol.* 14:213; Wight, The vascular extracellular matrix. In: Fuster V., Topol E., Nabel E., eds., *Atherosclerosis and Coronary Artery Disease,* 2004 Lippincott Williams and Wilkins, Philadelphia, Pa.; Nikkari et al., 1994 *Am. J. Pathol.* 144:1348; for biglycan see, e.g., Schwarz et al., 1990 *J. Biol. Chem.* 265: 22023; Itabashi et al., 2005 *Connect Tissue Res.* 46:67; Tufvesson et al., 2002 *Eur. J. Biochem.* 269:3688; Grande-Allen et al., 2004 *Glycobiol.* 14:621; Theocharis et al., 2002 *Atherosclerosis* 165:221; Stanescu 1990 *Sem. Arth. Rheum.* 20(3 Suppl. 1):51). Versican, with its multiple CS GAG chains, has been shown to be an effective inhibitor of elastogenesis (Huang et al., 2006 *Circ. Res.* 98:370). It is unclear, however, whether biglycan, a small leucine-rich proteoglycan (SLRP) which possesses two GAG chains containing chondroitin and dermatan sulphates, may also play a role in modulating elastic fiber formation.

For example, biglycan core protein was shown to be capable of binding to tropelastin and to elastic fiber microfibrils (Reinboth et al., 2002 *J. Biol. Chem.* 277:3950), and in a kidney injury model, biglycan stimulated expression of fibrillin-1, a major component of the microfibrils that form the scaffold on which tropoelastin is deposited (Schaefer et al., 2004 *Am. J. Pathol.* 165:383). Biglycan gene expression also decreased in abdominal aortic aneurysms where elastin was disrupted and fragmented (Theocharis et al., 2002 *Atherosclerosis* 165:221). On the other hand, biglycan stimulated cellular proliferation and migration, and induced cell elongation, features that are associated with a non-elastogenic phenotype (Shimizu-Hirota et al., 2004 *Circ. Res.* 94:1067; Kinsella et al., 2004 *Crit. Rev. Euk. Gene Expr.* 14:203).

Existing strategies to encourage ECM remodeling typically involve administering compositions containing preformed ECM components or materials derived therefrom, but generally lack any demonstration of induced ECM biosynthesis or of de novo elastic fiber formation.

For example, JP2004/250395 describes a topically applied composition containing collagen, elastin, chondroitin sulfate and hyaluronic acid to counteract aging in skin, bone and hair. WO2004/012665 describes an orally administered composition containing chondroitin sulfate, glucosamine, methylsulfonylmethane (MSM) and for disorders of joints and connective tissue. CA2518794 describes a lipid for topical application to deep airway alveoli to reduce lung surface tension in emphysema. CA2520057 describes plant flavonolignans ("silymarins") purported to promote type I collagen and/or elastin production in skin. WO2005/082386 describes cationic iron and magnesium salts used with digested elastic tissue to stimulate smooth muscle cell (SMC) elastogenesis and inhibit SMC proliferation, and to promote skin ECM deposition and dermal fibroblast proliferation. US2004/0146539 describes topical formulations containing vitamins, metabolites and/or plant extracts for cosmetic improvement to skin, including reducing wrinkles and other effects of aging. FR2847816 describes topical formulations containing an artificial peptide and vitamins (other than vitamin C) or nutrients for cosmetic improvement to skin, including reducing wrinkles and other effects of aging.

WO 0191700 describes small peptides derived from the amino acid sequence of elastin, and related structures, for administration orally, topically or via other parenteral routes to enhance connective tissue elasticity; peptide-coated vascular stents are also contemplated for improving flexibility and elasticity of blood vessels. WO99/45942 teaches the use of metastatin, a hyaluronan-binding complex derived from proteolytically digested cartilage, to inhibit cancer and angiogenesis, but is silent with respect to elastogenesis.

Transgenic approaches to promote elastic fiber biosynthesis in vitro have been described including transfection of cells with recombinant expression constructs encoding the elastin precursor subunit polypeptide tropoelastin (Robb et al., 1999 *Mol. Biol. Cell* 10:3595), and the V3 splice variant of the versican proteoglycan polypeptide (US 2004/0213762), which lacks chondroitin sulfate proteoglycan (CSPG) carbohydrate moieties but contains an intact hyaluronan-binding domain (Wight and Merrilees, 2004 *Circ. Res.* 94:1158). In this regard it is not completely understood what is the mechanism by which V3 may promote elastogenesis, in particular where both V3 and the CSPG-containing versican isoforms may be capable of influencing elastin fiber assembly at the cell surface by virtue of their binding interactions with cell surface hyaluronic acid (Wight and Merrilees, 2004 *Circ. Res.* 94:1158; Hinek et al., 2004 *Am. J. Pathol.* 164:119; Hinek et al., 2000 *Am. J. Hum. Genet.* 66:859; Hinek, 1996 *Biol. Chem.* 377:471; Hinek, 1994 *Cell Adhes. Commun.* 2:185).

Clearly there is a need for improved compositions and methods that exploit heretofore unrecognized molecular interactions to promote elastogenesis. The presently disclosed invention embodiments fulfill such a need and offer other related advantages.

BRIEF SUMMARY OF THE INVENTION

According to certain of the herein described embodiments, there is provided a method for promoting elastogenesis in a cell, comprising contacting a cell that is capable of elastogenesis with a composition that is selected from: (a) a mutant biglycan polypeptide which comprises an amino acid sequence as set forth in SEQ ID NO:3, (b) a mutated biglycan polypeptide which comprises an amino acid sequence as set forth in SEQ ID NO:37, (c) a mutated biglycan polypeptide which comprises a mutated form of a wildtype biglycan polypeptide, wherein the wildtype biglycan polypeptide comprises an amino acid sequence as set forth in SEQ ID NO:4 and the mutated form comprises the amino acid sequence of SEQ ID NO:4 in which at least one serine residue selected from a first serine residue at position 42 and a second serine residue at position 47 is mutated to an amino acid other than serine, and (d) a recombinant expression construct comprising a promoter operably linked to a polynucleotide sequence that encodes a polypeptide according to any one of (a) through (c), and thereby promoting elastogenesis in the cell.

In certain other embodiments there is provided a method for promoting elastogenesis in a cell, comprising contacting a cell that is capable of elastogenesis with a composition that is selected from (a) a mutant biglycan polypeptide which comprises an amino acid sequence having at least 80 percent sequence identity to SEQ ID NO:3, (b) a mutated biglycan polypeptide which comprises an amino acid sequence having at least 80 percent sequence identity to SEQ ID NO:37, (c) a mutated biglycan polypeptide which comprises an amino acid sequence that (i) includes at least amino acids 38 through 52 of SEQ ID NO:4 in which at least one serine residue selected from a first serine residue at position 42 and a second serine residue at position 47 is mutated to an amino acid other than serine, and (ii) has at least 80 percent sequence identity to SEQ ID NO:4, and (d) a recombinant expression construct comprising a promoter operably linked to a polynucleotide sequence that encodes a polypeptide according to any one of (a) through (c), and thereby promoting elastogenesis in the cell.

In certain other embodiments there is provided a method for promoting elastogenesis in a cell, comprising contacting a cell that is capable of elastogenesis with a composition that is selected from (a) a mutant biglycan polypeptide which comprises an amino acid sequence having at least 85 percent sequence identity to SEQ ID NO:3, (b) a mutated biglycan polypeptide which comprises an amino acid sequence having at least 85 percent sequence identity to SEQ ID NO:37, (c) a mutated biglycan polypeptide which comprises an amino acid sequence that (i) includes at least amino acids 38 through 52 of SEQ ID NO:4 in which at least one serine residue selected from a first serine residue at position 42 and a second serine residue at position 47 is mutated to an amino acid other than serine, and (ii) has at least 85 percent sequence identity to SEQ ID NO:4, (d) a mutant biglycan polypeptide which comprises an amino acid sequence having at least 90 percent sequence identity to SEQ ID NO:3, (e) a mutated biglycan polypeptide which comprises an amino acid sequence having at least 90 percent sequence identity to SEQ ID NO:37, (f) a mutated biglycan polypeptide which comprises an amino acid sequence that (i) includes at least amino acids 38 through 52 of SEQ ID NO:4 in which at least one serine residue selected from a first serine residue at position 42 and a second serine residue at position 47 is mutated to an amino acid other than serine, and (ii) has at least 90 percent sequence identity to SEQ ID NO:4, and (g) a recombinant expression construct comprising a promoter operably linked to a polynucleotide sequence that encodes a polypeptide according to any one of (a) through (f), and thereby promoting elastogenesis in the cell.

According to certain further embodiments of the above described methods, the step of contacting is performed in vitro. According to certain other further embodiments of the above described methods, the step of contacting is performed in vitro and the cell is present in an engineered biological tissue, which in certain still further embodiments is a connective tissue, or is selected from cartilage, ligament and tendon, or is selected from a blood vessel, heart tissue, skin, lung tissue, urogenital tissue and gastrointestinal tissue. According to certain further embodiments of the above described methods, the step of contacting is performed in a human or in a non-human mammal, wherein in certain further embodiments the non-human mammal is a non-human primate, a lagomorph, a rodent, an ungulate, a feliform, or a caniform, wherein in certain still further embodiments the lagomorph is selected from a rabbit, a hare and a pika, and the rodent is selected from a mouse, a rat, a gerbil, a guinea pig and a hamster.

According to certain further embodiments of the above described methods, the cell is a connective tissue cell. In certain embodiments the cell is a smooth muscle cell, a fibroblast, a myofibroblast, a chondrocyte, a pericyte, a glial cell, a glioma cell, a macrophage or an epithelial cell. In certain further embodiments the smooth muscle cell is a vascular smooth muscle cell, a gastrointestinal tract smooth muscle cell, a respiratory tract smooth muscle cell or a urogenital tract smooth muscle cell. In certain related embodiments the smooth muscle cell is a vascular smooth muscle cell that is an arterial smooth muscle cell or a venous smooth muscle cell.

Turning to certain other herein described embodiments, there is provided a method for treating a condition associated with inadequate elastin fiber formation, comprising administering, to a subject having or suspected of being at risk for having a condition associated with inadequate elastin fiber formation, an effective amount of a composition that is selected from (a) a mutant biglycan polypeptide which comprises an amino acid sequence having at least 80 percent sequence identity to SEQ ID NO:3, (b) a mutated biglycan polypeptide which comprises an amino acid sequence having at least 80 percent sequence identity to SEQ ID NO:37, (c) a mutated biglycan polypeptide which comprises an amino acid sequence that (i) includes at least amino acids 38 through 52 of SEQ ID NO:4 in which at least one serine residue selected from a first serine residue at position 42 and a second serine residue at position 42 is mutated to an amino acid other than serine, and (ii) has at least 80 percent sequence identity to SEQ ID NO:4, and (d) a recombinant expression construct comprising a promoter operably linked to a polynucleotide sequence that encodes a polypeptide according to any one of (a) through (c), and thereby treating the condition associated with inadequate elastin fiber formation. In certain further embodiments the condition associated with inadequate elastin fiber formation is selected from emphysema, chronic obstructive pulmonary disease, idiopathic pulmonary fibrosis, lymphangioleiomyomatosis, atherosclerosis, aneurysm, aortic dissection and restenosis. In certain other further embodiments the condition associated with inadequate elastin fiber formation is selected from cutis laxa, pseudoxanthoma elasticum and a pelvic floor disorder. In certain other further embodiments the condition associated with inadequate elastin fiber formation is an aging-associated condition, or results in wrinkled skin, or comprises a valvular disease. In certain other further embodiments the condition associated with inadequate elastin fiber formation is selected from Costello Syndrome, Hurler Disease, Williams-Beuren Syndrome, Morquio B disease, infantile GM1-gangliosidosis, supravalvular aortic stenosis, pregnancy, Marfan's syndrome, Ehlers-Danlos syndrome, aortic coarctation and bicuspid aortic valve disease.

According to certain further embodiments of the above described methods, the recombinant expression construct is present in a vector, which in certain further embodiments is a viral vector, which in certain still further embodiments is present in or derived from a virus that is selected from an adenovirus, an adeno-associated virus, a herpesvirus, a lentivirus, a poxvirus, and a retrovirus. In certain other embodiments the recombinant expression construct is present in a host cell.

Other embodiments described herein provide a method for promoting elastogenesis in a cell, comprising contacting a cell that is capable of elastogenesis with a composition that is selected from (a) a polypeptide which comprises an amino acid sequence as set forth in one of SEQ ID NOS:11, 13, 15, 17, 19, 21, 23 and 25, (b) a polypeptide which comprises an amino acid sequence having at least 80% sequence identity to (a), (c) a polypeptide which comprises an amino acid sequence having at least 90% sequence identity to (a), and (d) a recombinant expression construct comprising a promoter operably linked to a polynucleotide sequence that encodes a polypeptide according to any one of (a) through (c), and thereby promoting elastogenesis in the cell. In certain further embodiments the step of contacting is performed in vitro, and in certain other further embodiments the step of contacting is performed in vitro and the cell is present in an engineered biological tissue. In certain still further embodiments the engineered biological tissue is a connective tissue, which in certain still further embodiments is selected from cartilage, ligament and tendon. In certain other related embodiments the engineered biological tissue is selected from a blood vessel, heart tissue, skin, lung tissue, urogenital tissue and gastrointestinal tissue. In certain other further embodiments of the above described method, the step of contacting is performed in a human or in a non-human mammal, wherein in certain still further embodiments the non-human mammal is selected from a non-human primate, a lagomorph, a rodent, an ungulate, a feliform, and a caniform. In certain further embodiments the lagomorph is selected from a rabbit, a hare and a pika, and the rodent is selected from a mouse, a rat, a gerbil, a guinea pig and a hamster.

In certain other embodiments of the above described method for promoting elastogenesis in a cell, the cell is a connective tissue cell. In certain embodiments the cell is selected from a smooth muscle cell, a fibroblast, a myofibroblast, a chondrocyte, a pericyte, a glial cell, a glioma cell, a macrophage and an epithelial cell. In certain further embodiments the smooth muscle cell is selected from a vascular smooth muscle cell, a gastrointestinal tract smooth muscle cell, a respiratory tract smooth muscle cell and a urogenital tract smooth muscle cell. In certain other further embodiments the smooth muscle cell is a vascular smooth muscle cell that is selected from an arterial smooth muscle cell and a venous smooth muscle cell.

In another herein described embodiment there is provided a method for treating a condition associated with inadequate elastin fiber formation, comprising administering, to a subject having or suspected of being at risk for having a condition associated with inadequate elastin fiber formation, an effective amount of a composition that is selected from (a) a polypeptide which comprises an amino acid sequence as set forth in one of SEQ ID NOS:11, 13, 15, 17, 19, 21, 23 and 25, (b) a polypeptide which comprises an amino acid sequence having at least 80% sequence identity to (a), (c) a polypeptide which comprises an amino acid sequence having at least 90% sequence identity to (a), and (d) a recombinant expression construct comprising a promoter operably linked to a polynucleotide sequence that encodes a polypeptide according to any one of (a) through (c), and thereby treating the condition associated with inadequate elastin fiber formation.

In certain further embodiments the condition associated with inadequate elastin fiber formation is selected from emphysema, chronic obstructive pulmonary disease, idiopathic pulmonary fibrosis, lymphangioleiomyomatosis, atherosclerosis, aneurysm, aortic dissection and restenosis. In certain other further embodiments the condition associated with inadequate elastin fiber formation is selected from cutis laxa, pseudoxanthoma elasticum and a pelvic floor disorder. In certain other further embodiments the condition associated with inadequate elastin fiber formation is an aging-associated condition or results in wrinkled skin, or comprises a valvular disease. In certain further embodiments the condition associated with inadequate elastin fiber formation is selected from Costello Syndrome, Hurler Disease, Williams-Beuren Syndrome, Morquio B disease, infantile GM1-gangliosidosis, supravalvular aortic stenosis, pregnancy, Marfan's syndrome, Ehlers-Danlos syndrome, aortic coarctation, and bicuspid aortic valve disease.

In certain further embodiments of the above described method for promoting elastogenesis in a cell and method for treating a condition associated with inadequate elastin fiber formation, the recombinant expression construct is present in a vector, which in certain embodiments is a viral vector, which in certain still further embodiments is present in or derived from a virus that is selected from an adenovirus, an adeno-associated virus, a herpesvirus, a lentivirus, a poxvirus, and a retrovirus. In certain other further embodiments the recombinant expression construct is present in a host cell.

According to other embodiments herein disclosed there is provided a method for promoting elastogenesis in a cell, comprising contacting a cell that is capable of elastogenesis with a composition that comprises a metastatin proteoglycan which comprises a product of a process comprising (i) digesting cartilage with trypsin under conditions and for a time sufficient to generate a hyaluronan-binding complex therefrom, wherein said hyaluronan-binding complex comprises one or more tryptic fragments of a hyaluronan-binding region of aggrecan (HABR) or a link 2 polypeptide that comprises at least one amino acid sequence selected from the group consisting of SEQ ID NOS:28-36 and 38-41; and (ii) isolating the hyaluronan-binding complex by affinity binding of said complex to hyaluronan to obtain said metastatin proteoglycan; and thereby promoting elastogenesis in the cell.

In certain further embodiments the step of contacting is performed in vitro, and in certain other embodiments the step of contacting is performed in vitro and the cell is present in an engineered biological tissue. In certain further embodiments the biological tissue is a connective tissue, which in certain still further embodiments is selected from cartilage, ligament and tendon. In certain other embodiments the engineered biological tissue is selected from a blood vessel, heart tissue, skin, lung tissue, urogenital tissue and gastrointestinal tissue. In certain other embodiments of the above described method, the step of contacting is performed in a human or in a non-human mammal, wherein according to certain further embodiments the non-human mammal is selected from a non-human primate, a lagomorph, a rodent, an ungulate, a feliform, and a caniform, and wherein according to certain other further embodiments the lagomorph is selected from a rabbit, a hare and a pika, and the rodent is selected from a mouse, a rat, a gerbil, a guinea pig and a hamster.

In certain other embodiments of the above described method, the cell is a connective tissue cell. In certain other embodiments the cell is selected from a smooth muscle cell, a fibroblast, a myofibroblast, a chondrocyte, a pericyte, a glial cell, a glioma cell, a macrophage and an epithelial cell. In certain further embodiments the smooth muscle cell is selected from a vascular smooth muscle cell, a gastrointestinal tract smooth muscle cell, a respiratory tract smooth muscle cell and a urogenital tract smooth muscle cell. In certain other embodiments the smooth muscle cell is a vascular smooth muscle cell that is an arterial smooth muscle cell or a venous smooth muscle cell.

Also disclosed herein is a method for treating a condition associated with inadequate elastin fiber formation, comprising administering, to a subject having or suspected of being at risk for having a condition associated with inadequate elastin fiber formation, an effective amount of a composition that comprises a metastatin proteoglycan which comprises a product of a process comprising (i) digesting cartilage with trypsin under conditions and for a time sufficient to generate a hyaluronan-binding complex therefrom, wherein said hyaluronan-binding complex comprises one or more tryptic fragments of a hyaluronan-binding region of aggrecan (HABR) or a link 2 polypeptide that comprises at least one amino acid sequence selected from the group consisting of SEQ ID NOS:28-36 and 38-41; and (ii) isolating the hyaluronan-binding complex by affinity binding of said complex to hyaluronan to obtain said metastatin proteoglycan; and thereby treating the condition associated with inadequate elastin fiber formation. In a further embodiment the condition associated with inadequate elastin fiber formation is selected from emphysema, chronic obstructive pulmonary disease, idiopathic pulmonary fibrosis, lymphangioleiomyomatosis, atherosclerosis, aneurysm, aortic dissection and restenosis. In another further embodiment the condition associated with inadequate elastin fiber formation is selected from cutis laxa, pseudoxanthoma elasticum and a pelvic floor disorder. In certain related embodiments the condition associated with inadequate elastin fiber formation is an aging-associated condition or results in wrinkled skin or comprises a valvular disease. In certain embodiments the condition associated with inadequate elastin fiber formation is selected from Costello Syndrome, Hurler Disease, Williams-Beuren Syndrome, Morquio B disease, infantile GM1-gangliosidosis, supravalvular aortic stenosis, pregnancy, Marfan's syndrome, Ehlers-Danlos syndrome, aortic coarctation, and bicuspid aortic valve disease.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWING(S)

FIG. 1 shows a schematic depiction of retroviral vectors LXSN, LBSN and LMBSN. LTR, long terminal repeat; NEO, neomycin phosphotransferase; SV, SV40 fragment containing early promoter; pA, polyadenylation site; hbiglycan, hman biglycan cDNA; mhbiglycan, mutant human biglycan cDNA. Arrows indicate transcriptional start sites and direction of transcription. Arrowheads indicate sites of serine to alanine mutations, to prevent covalent attachment of glycosaminoglycan (GAG) side chains.

FIGS. 2A-2D shows expression of rat biglycan (LXSN), human biglycan (LBSN) and mutant human biglycan (LMBSN) by Fisher 344 rat aortic smooth muscle cells (ASMC) at day 14 following transduction with indicated retroviral vectors. (FIG. 2A) Northern blot was probed with cDNA of human biglycan (hbi) that hybridized to endogenous rat biglycan (rb) and the mutant human biglycan. Endogenous rat and human biglycan mRNA is 1.7 kb, increased to 2.5 kb following transduction with the LXSN vector due to inclusion of the neomycin phosphotransferase sequence (794 bp). (FIG. 2B) Western blot of biglycan core protein isolated from media conditioned for 48 hours prior to collection at day 14, digestion with chondroitin ABC lyase, and detection by antibody LF51 specific for human biglycan core protein to the exclusion of rat biglycan core protein. (FIG. 2C) Western blot of samples collected over DEAD column prior to chondroitinase digestion, showing lack of binding of mutant human biglycan due to lack of glycosaminoglycan (GAG) chains. (FIG. 2D) SDS gradient PAGE 94% to 12%) loaded with equal counts ($25 \times 10^3$ dpm) [$^{35}$S] sulphate-labeled secreted proteoglycans, showing overexpression of biglycan (bi) by LBSN-transduced cells compared with LXSN-transduced cells, and reduction of sulphate-labeled chains by LMBSN-transduced cells.

Figure 3:
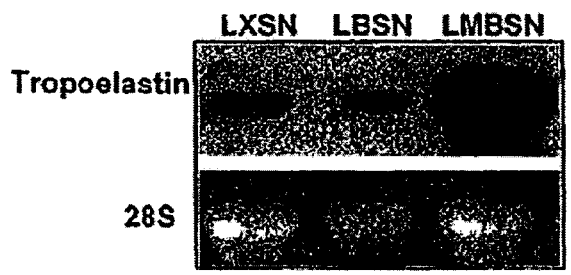
Figure 3:
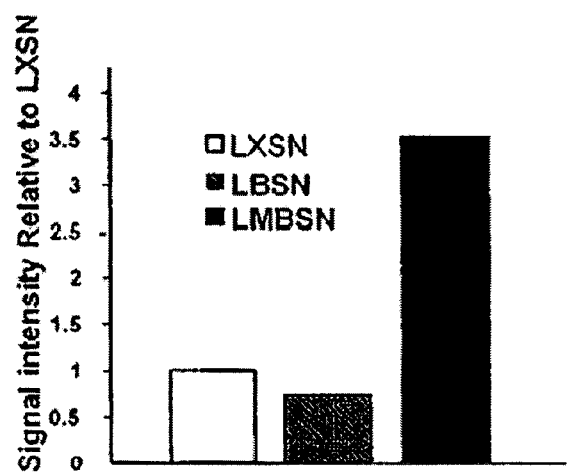
Figure 3:
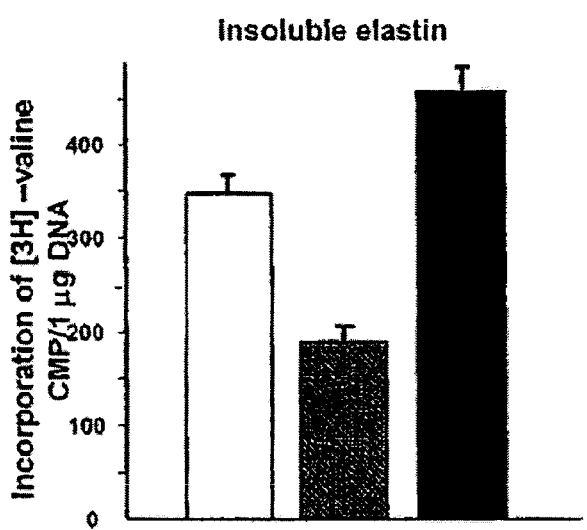

FIGS. 3A-3C shows elastin expression by cells transduced with LBSN, LMBSN or LXSN. (FIG. 3A) Expression of tropoelastin mRNA: Northern blot of 14-day ASMC cultures probed with tropoelastin cDNA showing increased expression of message in LMBSN-transduced cells compared with LXSN-transduced and LBSN-transduced cells. (FIG. 3B) Signal intensity corrected to 28S rRNA subunit and relative to LXSN level. (FIG. 3C) Quantitative analysis of immunoprecipitable [$^3$H]-valine labeled insoluble elastin showing significant ($p<0.05$) increase in LMBSN-transduced cells and significant decrease ($p<0.05$) in LBSN-transduced cells.

Figure 4:
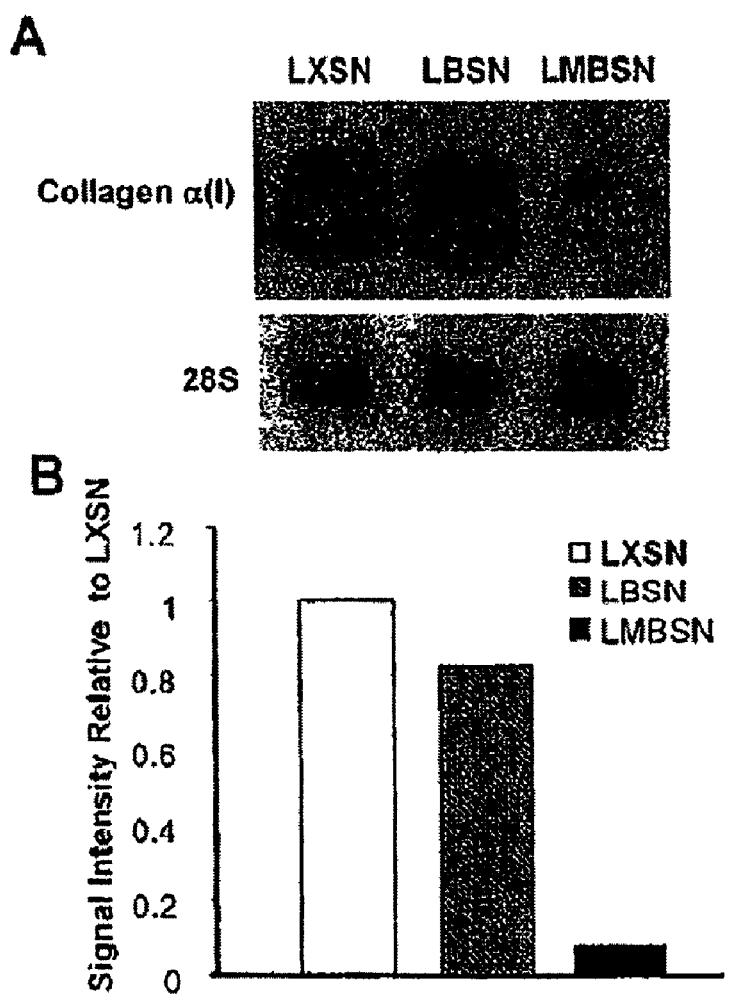

FIGS. 4A-4B shows collagen expression by cells transduced with LBSN, LMBSN or LXSN. (FIG. 4A) Expression of collagen $\alpha$(I) mRNA. Northern blot of 14-day rat ASMC cultures probed for collagen $\alpha$(I) showing markedly decreased expression by LMBSN cells. (FIG. 4B) Signal intensity corrected to 28S and relative to LXSN expression.

Figure 5:
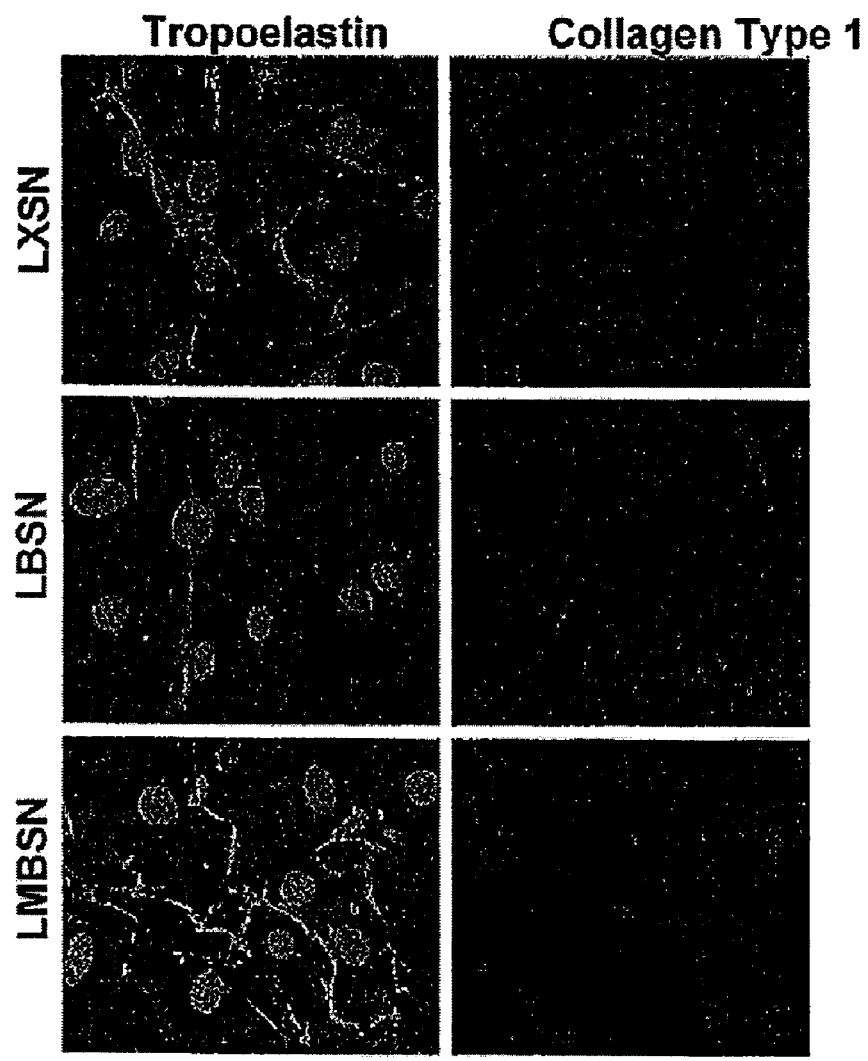

FIG. 5 shows immunostaining for tropoelastin and Type I collagen in 10-day cultures of rat ASMC transduced with LBSN, LMBSN or LXSN. Tropoelastin decreased and Type I collagen increased in LBSN-transduced cells overexpressing human biglycan, compared with LXSN- and LMBSN-transduced cells; LMBSN-transduced cells exhibited increased elastin and decreased collagen immunostaining.

Figure 6:
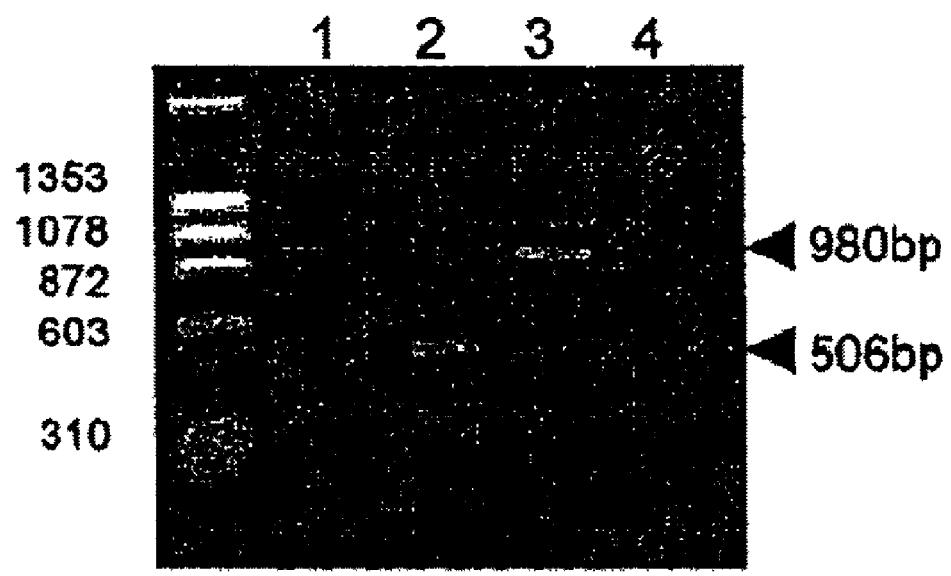

FIG. 6 shows RT-PCR determination of in vivo expression of transgenic human biglycan four weeks after carotid artery balloon injury and seeding in Fisher 344 rats of ASMC transduced with LBSN, LMBSN or LXSN. Lane 1, conditional negative control; lane 2, LXSN cell-seeded vessel with LXSN forward and LXSN reverse primers; lane 3, LBSN cell-seeded vessel with LXSN forward and biglycan reverse primers; lane 4, LMBSN cell-seeded vessel with LSXN forward and biglycan reverse primers.

Figure 7:
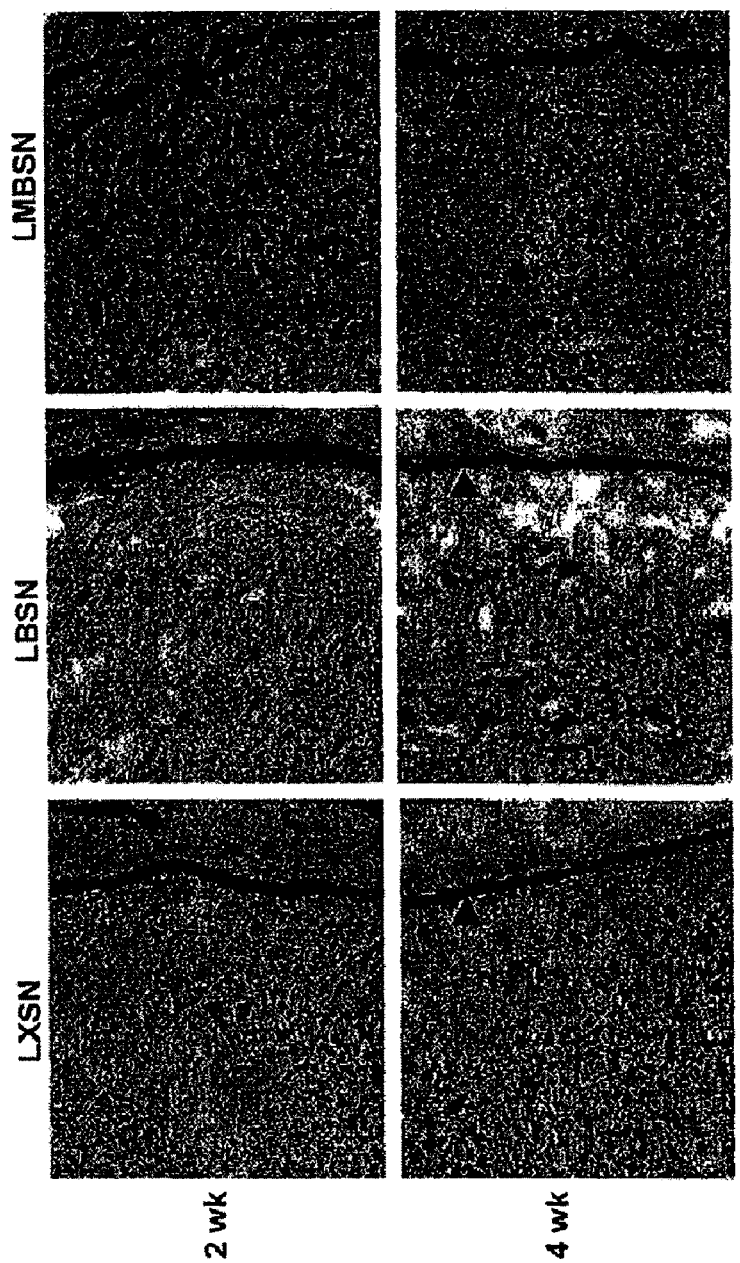

FIG. 7 shows orcein (dark red) staining of deep neointimae showing more abundant and more organized elastin deposits in rat blood vessels seeded with LMBSN-transduced ASMC compared to vessels seeded with LXBSN-transduced and LBSN-transduced cells. Elastin deposits in neointima formed from mutant biglycan-expressing cells were generally aggregated into lamellae-like structures, mostly parallel to the internal elastic lamina (arrowheads).

Figure 8:
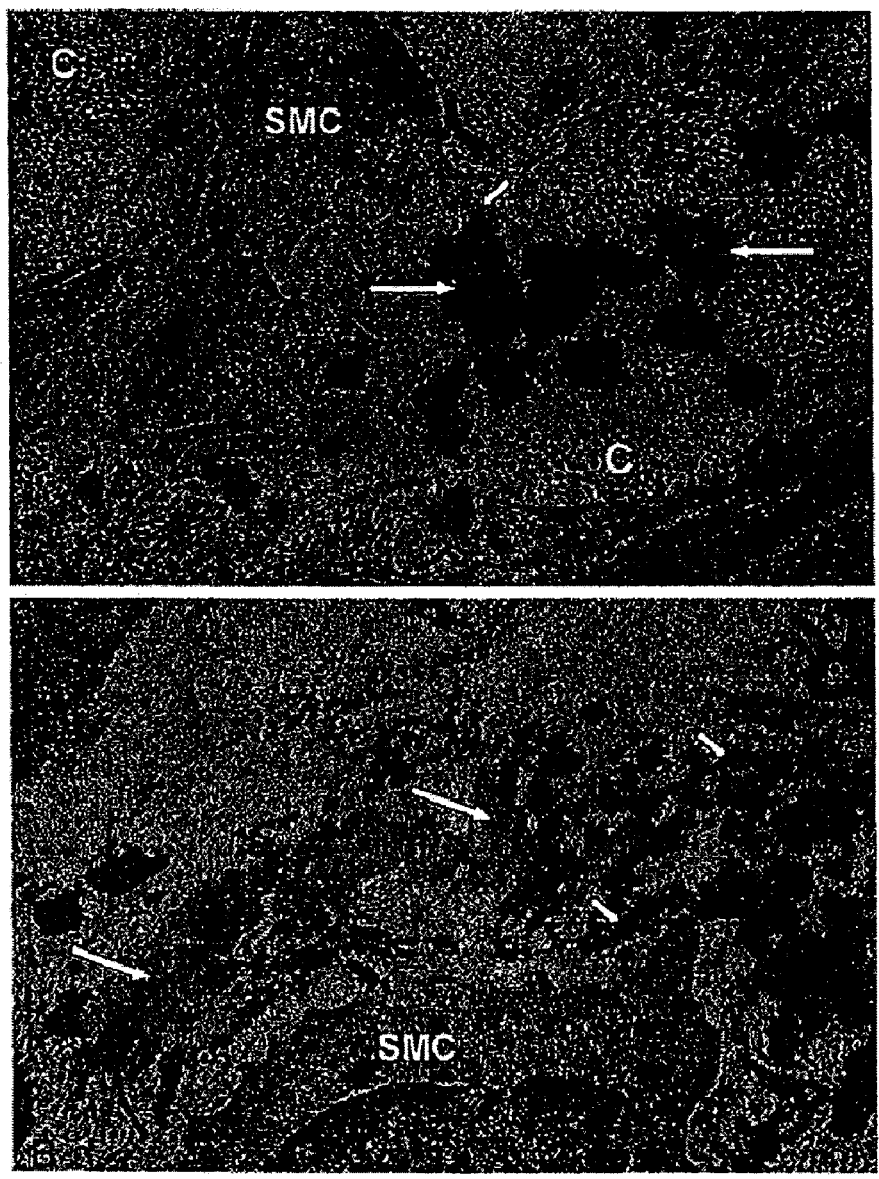

FIG. 8 shows electron micrographs of two-week old neointimae formed by LBSN- (FIG. 8A) and LMBSN- (FIG. 8B) transduced cells showing more abundant and aggregated mature elastin (long arrows) and microfibrillar-rich immature elastin (short arrows), and reduced collagen content (C), in the extracellular matrix produced by mutant biglycan cells compared with matrix formed by cells overexpressing normal human biglycan. SMC; smooth muscle cells.

Figure 9:
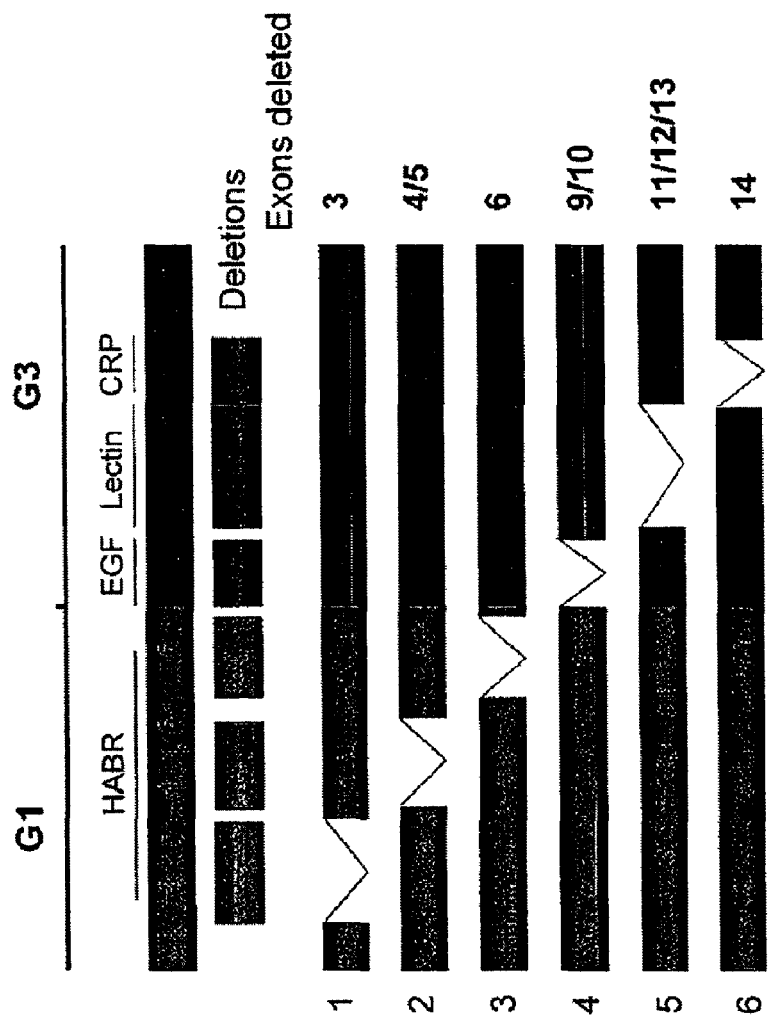

FIG. 9 shows a schematic diagram of versican V3 isoform exon utilization by the engineered versican V3-derived polypeptides comprising the amino acid sequences set forth in SEQ ID NOS:9 (exon 3 deleted), 11 (exons 4/5 deleted), 12 (exon 6 deleted), 15 (exons 9/10 deleted), 17 (exons 11/12/13 deleted) and 19 (exon 14 deleted).

Figure 10:
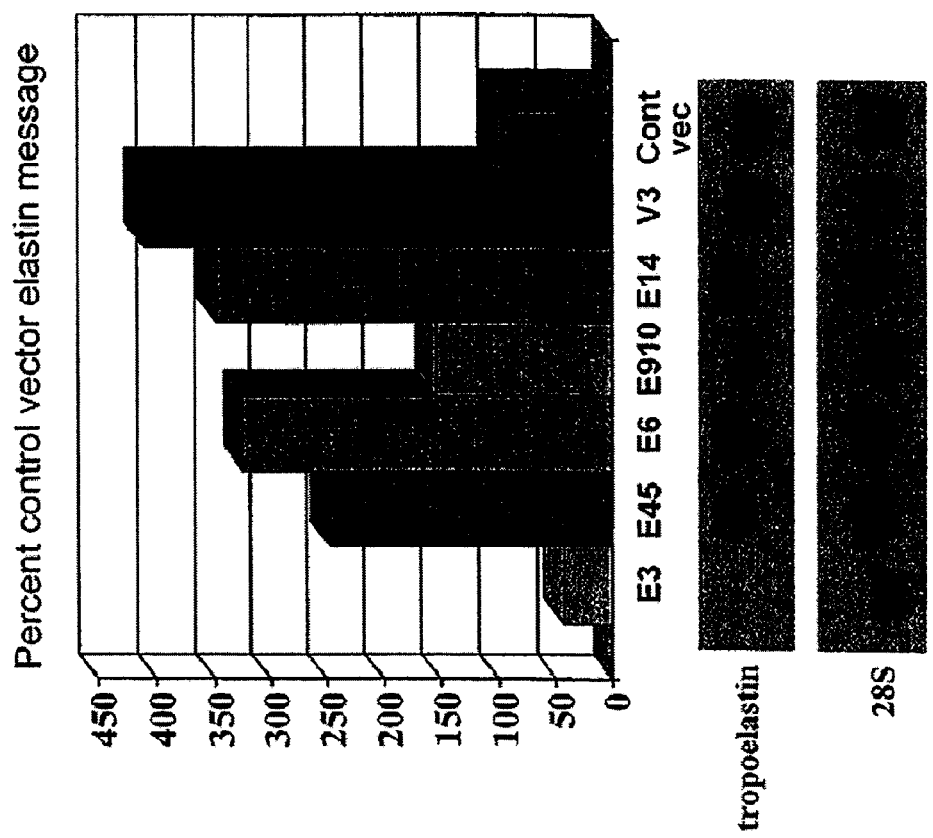

FIG. 10 shows northern blot analysis of smooth muscle cell tropoelastin mRNA expression and the effects of the engineered V3-derived polypeptides comprising the amino acid sequences set forth in SEQ ID NOS:9 (exon 3 deleted), 11 (exons 4/5 deleted), 12 (exon 6 deleted), 15 (exons 9/10 deleted), and 19 (exon 14 deleted); V3, SEQ ID NO:27, "Cont vec", vector-only control.

DETAILED DESCRIPTION OF THE INVENTION

The present invention relates, according to certain herein disclosed embodiments, to compositions and methods for altering (i.e., increasing or decreasing in a statistically significant manner, and in preferred embodiments, increasing) biological elastic fiber formation, or elastogenesis, in higher vertebrates including humans and other mammals. Described herein is the discovery that in the presence of certain presently disclosed agents having unexpected pro-elastogenic functionality, elastogenesis can be promoted by counteracting natural cell surface mechanisms that would otherwise impair elastin fiber formation. Such pro-elastogenic agents include, in certain embodiments, structurally modified biglycan, including mutated biglycan polypeptides, which lack one or both of the glycosaminoglycan chains that are present in wildtype biglycan, for example, by virtue of such mutants (e.g., SEQ ID NO:3) having mutations such as point mutations (e.g., amino acid substitutions) at one or both of the two glycosaminoglycan attachment sites found in wildtype (e.g., SEQ ID NO:4) biglycan polypeptides, such that one or both GAG chains are absent. In certain other embodiments, pro-elastogenic agents may include non-naturally occurring polypeptides that comprise selected portions of the ECM chondroitin sulfate proteoglycan referred to above and known as versican. In certain other embodiments, pro-elastogenic agents include metastatin, a cartilage link protein-derived, peptide-containing hyaluronan-binding complex that contains aggrecan hyaluronan-binding region (HABR) polypeptides.

These and related embodiments are useful in a variety of contexts, for example, to promote elastogenesis in situations where it may be desirable to create, restore and/or enhance an elastic (e.g., elastin fiber-containing) extracellular matrix and/or connective tissue component in one or more bodily tissues, organs and/or interstitial spaces. Accordingly, presently disclosed compositions and methods find utility in providing treatments for diseases, disorders, conditions and the like, in which altered elastogenesis may be desired, such as a condition associated with inadequate elastin fiber formation. For example, clinical benefit may be obtained according to embodiments disclosed herein, by enhancing the elastin fiber-containing elastic connective tissue compartment in tissues such as blood vessel walls, skin, heart, central nervous system (CNS), lung and/or other cells, tissues and organs. Accordingly, certain non-limiting examples in which the presently disclosed embodiments may find use include uses in the treatment of Costello Syndrome, Hurler Disease, Williams-Beuren Syndrome, Morquio B disease, infantile GM1-gangliosidosis, supravalvular aortic stenosis, pregnancy, Marfan's syndrome, Ehlers-Danlos syndrome, aortic coarctation, and bicuspid aortic valve disease.

Compositions and methods according to certain embodiments disclosed herein relate to agents that, according to non-limiting theory, may promote elastogenesis in part by interfering with specific anti-elastogenic intermolecular binding events on the surfaces of elastogenic cells, i.e., cells that are capable of expressing protein constituents of elastic fibers (e.g., tropoelastin, fibrillin-1, fibrillin-2, MAGP-1, MAGP2, emilin), and/or of organizing the assembly of these constituents into elastic fibers. Naturally derived and artificial pro-elastogenic agents as provided herein exhibit useful biological activities that have not been previously contemplated for counteracting endogenous cell surface elastogenic inhibitors.

Accordingly, presently disclosed embodiments provide compositions and methods for promoting elastogenesis that relate to assembly of monomeric tropoelastin, the elastin precursor subunit, into elastic fibers which comprise microfibrils containing fibrillins 1 and 2 along with crosslinked tropoelastin, microfibril-associated proteins such as MAGP1 and MAGP2, the elastin-microfibril interface protein emilin and other components (see e.g., Reinboth et al., 2002 *J. Biol. Chem.* 277:3950, and references cited therein; Zimmermann et al., 1994 *J. Cell Biol.* 124:817). According to these and related embodiments, elastogenesis may be promoted when, in a statistically significant manner, an elastic (e.g., elastin fiber-containing) extracellular matrix and/or connective tissue component is created, restored, increased and/or enhanced.

For instance, promotion of elastogenesis may take place at a cell surface or in an extracellular milieu in one or more bodily tissues, organs and/or interstitial spaces, and/or in an artificial or bioengineered cell, tissue and/or organ system. Histological, biochemical and immunochemical methodologies and criteria for determining elastogenesis are known to those familiar with the art, including immunostaining and morphometric analysis (e.g., Hinek et al., 2004 *Am. J. Pathol.* 164:119; Merrilees et al., 2002 *Circ. Res.* 90:481), assays for soluble tropoelastin and insoluble elastin (Hinek et al., 2004 *Am. J. Pathol.* 164:119; Robb et al. 1999 *Mol. Biol. Cell* 10:3595; Starcher 2005 *Exp. Lung Res.* 31:873), tropoelastin mRNA quantification and elastin binding protein immunoprecipitation (Hinek et al., 1991 *J. Clin. Invest.* 88:2083; Hinek et al., 2004 *Am. J. Pathol.* 164:119; Kelleher et al., 2004 *Curr. Top. Dev. Biol.* Chapter 6, pp. 153-188) and other methodologies (e.g., Hinek et al., 1998 *J. Neuropath. Exp. Neurol.* 57:439; Hinek et al., 2000 *Am. J. Hum. Genet.* 66:859; Hinek et al., 2000 *Am J. Hum. Genet.* 67:23; Hinek et al., 2000 *Am. J. Pathol.* 156:925).

As described herein, release of elastin or tropoelastin from a cell surface elastin binding protein, and/or dissociation of a cell surface elastin binding protein from the cell surface, may be effected by binding interactions between an elastogenic inhibitor and the elastin binding protein (EBP). Accordingly, such release of elastin or tropoelastin from the EBP, and/or dissociation of the EBP from the cell surface, are substantially impaired by certain of the herein described methods when cell surface EBPs substantially but not necessarily completely retain detectably bound elastin or tropoelastin, and/or when cell surfaces substantially but not necessarily completely retain detectable EBP. Elastin/tropoelastin release and/or EBP dissociation are thus substantially impaired when cell surface EBPs retain preferably at least 50% of detectably bound elastin or tropoelastin and/or cell surfaces retain at least 50% of detectable cell surface EBP; and more preferably when cell surface EBPs retain at least 75% of detectably bound elastin or tropoelastin and/or cell surfaces retain at least 75% of detectable surface EBP. Most preferably, elastin/tropoelastin release and/or EBP dissociation are substantially impaired when cell surface EBPs retain >90% of detectably bound elastin or tropoelastin and/or cell surfaces retain >90% of detectable cell surface EBP.

In certain preferred embodiments elastogenesis may be promoted through activities involving a cell that is capable of elastogenesis, which includes any cell that naturally or as the result of natural or artificial induction, stimulation, activation or the like, and/or as a result of genetic engineering, participates in promotion of elastogenesis as also described above. According to certain related embodiments the cell that is capable of elastogenesis may be a connective tissue cell, including, for instance, a fibroblast, a mesangial cell, a chondrocyte, an adipocyte and/or a macrophage, and also including a mast cell, a monocyte, a lymphocyte, a plasma cell and/or an eosinophil, or other cells that may be found in connective tissue. Accordingly, in certain preferred embodiments, a cell that is capable of elastogenesis may comprise one or more of a smooth muscle cell (e.g., a vascular smooth muscle cell such as an arterial smooth muscle cell or a venous smooth muscle cell, a gastrointestinal tract smooth muscle cell, a respiratory tract smooth muscle cell, or a urogenital tract smooth muscle cell), a fibroblast, a myofibroblast, a chondrocyte, a pericyte, a glial cell, a glioma cell, a macrophage, and an endothelial cell, or another cell type.

A cell that is capable of elastogenesis may also include any cell that is capable of synthesizing elastin naturally or as the result of genetic engineering, including by introduction into such a cell of polynucleotide sequences encoding elastin polypeptides (e.g., tropoelastin-encoding sequences) and also including by introduction of regulatory polynucleotides that do not themselves encode elastin or tropoelastin polypeptides but that induce expression of endogenous cellular elastin expression through gene activation mechanisms, such as those described in U.S. Pat. No. 5,968,502.

Certain related embodiments thus provide promotion of elastogenesis in an engineered biological tissue, for instance, an engineered biological tissue comprising a cell that is capable of elastogenesis as described above. Other engineered biological tissues are also contemplated for certain such embodiments, including specific tissues that may be derived from stem cells through prescribed in vitro and/or in vivo culture conditions as are known to those familiar with the art, including methodologies for inducing cellular differentiation along desired developmental pathways or cell type lineages. The engineered biological tissue, whether or not derived from a stem cell, may comprise a blood vessel, heart tissue, skin, lung tissue, urogenital tissue, gastrointestinal tissue or another cell or tissue type. For example, production of extracellular matrix components is described in tissue-engineered blood vessels by Heydarkhan-Hagvall et al. (2006 *Tiss. Eng.* 12(4):831-842); in tissue-engineered skin by Bello et al. (2001 *Am. Jl. Clin. Dermatol.* 2:305-313) and by Casasco et al. (2004 *J. Mol. Histol.* 35:421-428); in tissue-engineered lung by Cortiella et al. (2006 *Tiss. Engineer.* 12:1213); and in tissue-engineered airway wall by Choe et al. (2006 *Am J. Respir. Cell Mol. Biol.* 35:306-313).

Conditions associated with inadequate elastin fiber formation include diseases, disorders, conditions and the like, and/or related sequelae, wherein the presence of elastic fibers in a subject is decreased in a statistically significant manner, and/or distribution of elastic fibers is inappropriate, relative to that seen in a normal healthy control subject in the same or a corresponding tissue. Such conditions may result from tissue degradation over time without elastogenic replacement, such as due to aging, physical or mechanical stressors, surgical intervention or the like, and/or from genetic factors predisposing an individual to inadequate elastin fiber formation and/or to inappropriate distribution of elastic fibers. Conditions associated with inadequate elastin fiber formation may also result from the pathogenetic mechanisms of specific diseases, for instance, from aneurysms, restenosis lesions, emphysema, and/or from skin wounds or aging-associated damage such as skin wrinkling, and/or by genetic defects linked to the elastin gene (see, e.g., Robb et al., 1999 *Mol. Biol. Cell* 10:3595 and references cited therein).

Examples of conditions associated with inadequate elastin fiber formation include emphysema, chronic obstructive pulmonary disease, idiopathic pulmonary fibrosis, lymphangioleiomyomatosis (Merrilees et al., 2004 *J. Pathol.* 203:653), atherosclerosis, aneurysm, aortic dissection and restenosis, cutis laxa, pseudoxanthoma elasticum, a pelvic floor disorder (e.g., Liu et al 2006 *Am J Path.* 168:519), cardiac valvular disease, pregnancy, coarctation (narrowing) of the aorta, and bicuspid aortic valve. Determination of the presence in a subject, such as a patient, of a condition associated with inadequate elastin fiber formation may be made according to disclosure provided herein and as will be known to those familiar with the relevant art, for example, by reference to one or more of Lapiere C M and Krieg T (eds.), *Connective Tissue Diseases of the Skin*, 1993 Marcel Dekker, NY; *Mixed Connective Tissue Disease*, 2004 ICON Health Publications, London; Belch J J F and Zurier R B (eds.), *Connective Tissue Diseases*, 1995 Chapman and Hall, London and Boca Raton, Fla.; Royce P M and Steinmann B (eds.), *Connective Tissue and Its Heritable Disorders: Molecular, Genetic and Medical Aspects*—2$^{nd}$ Ed., 2002, Wiley-Liss, NY; Beighton P (Ed.), McKusick's Heritable Disorders of Connective Tissue-5$^{th}$ Ed., 1993, C.V. Mosby Co., St. Louis, Mo.; and Rimoin et al., *Emery and Rimoin's Principles and Practice of Medical Genetics*—4$^{th}$ Ed., 2001, Churchill Livingstone/Elsevier, N.Y. Descriptions of particular relevance to reported deficiencies in elastic fiber formation may include Hinek et al., 2004 *Am J Pathol.* 164:119; Hinek, 2003 *Ann. Diagnost. Pediatr. Pathol.* 7:7-14; Mochizuki et al., 2002 *J. Biol. Chem.* 277:44854; Urban et al., 2002 *Am. J. Hum. Genet.* 71:30-44; Hinek et al., 2000 *Am. J. Hum. Genet.* 67:23-36; Hinek et al., 2000 *Am J. Hum. Genet.* 66:859; and Hinek et al., 2000 *Am. J. Pathol.* 156:925-938.

Embodiments disclosed herein may find uses in promoting elastogenesis in a cell that is capable of elastogenesis and that is derived from a human or non-human subject, including embodiments whereby elastogenesis is promoted in vitro and also including embodiments whereby elastogenesis is promoted in vivo. Human and non-human subjects may, in particularly preferred embodiments, have or may be suspected of having or of being at risk for having or developing a condition associated with inadequate elastin fiber formation. Non-human subjects include non-human primates (e.g., chimpanzee, macaque, baboon, orangutan, etc.) and other non-human mammals such as lagomorphs (e.g., rabbit, hare, pika), rodents (e.g., mouse, rat, gerbil, guinea pig, hamster), ungulates (e.g., bovine, sheep, goat, horse, etc.), feliform (e.g., domestic cat), and caniform (e.g., dogs, seals, sea lions, beavers, otters, etc.).

Pro-Elastogenic Agents: Mutant Biglycan Polypeptides, Engineered Versican V3-Derived Polypeptides, and Metastatin As noted above, certain herein disclosed embodiments contemplate pro-elastogenic agents that may comprise a mutant biglycan polypeptide and/or an engineered versican V3-derived polypeptide, and/or a recombinant expression construct that comprises a promoter operably linked to a polynucleotide sequence that encodes such polypeptide(s).

A mutant biglycan polypeptide for use according to certain herein disclosed embodiments preferably lacks one or both glycosaminoglycan (GAG) chains that are typically found covalently attached to wildtype (i.e., non-mutant) biglycan polypeptides. Preparation of biglycan polypeptides, including recombinantly expressed biglycan polypeptides, is known in the art (e.g., Fisher et al., 1991 *J. Biol. Chem.* 266:14371; Tufvesson et al. 2002 *Eur. J. Bioch.* 269:3688; Schwarz et al., 1990 *J. Biol. Chem.* 265:22023), and generation of mutants lacking one or both GAG attachment sites may be accomplished according to routine methodologies as disclosed herein and using established molecular biology techniques. Exemplary mutant biglycan polypeptides comprise the 331-amino acid polypeptides (following processing to remove the N-terminal 37 amino acids of the precursor polypeptides) of SEQ ID NOS:3, 4 and 37 in which substitution mutations are found at amino acid positions 5 and/or 10 of the processed protein (corresponding, respectively, to amino acid positions 42 and 47 in SEQ ID NOS:3, 4 and 37) relative to the wildtype biglycan amino acid sequence set forth in SEQ ID NO:4, wherein the mutant biglycan polypeptides are incapable of covalent biosynthetic posttranslational attachment of GAG chains. In certain such embodiments, for example, the mutant biglycan polypeptide comprises the amino acid sequence set forth in SEQ ID NO:3, having alanine residues at positions 42 and 47 (corresponding, respectively, to positions 5 and 10 following processing to remove the N-terminal 37 amino acids of the precursor polypeptide) as substitution mutations for the serine residues found in the corresponding positions of the wildtype biglycan polypeptide (SEQ ID NO:4). In certain other such embodiments, for example, the mutant biglycan polypeptide comprises the amino acid sequence set forth in SEQ ID NO:37, having any amino acid other than serine as the amino acid residues at positions 42 and 47 (corresponding, respectively, to positions 5 and 10 following processing to remove the N-terminal 37 amino acids of the precursor polypeptide) as substitution mutations for the serine residues found in the corresponding positions of the wildtype biglycan polypeptide (SEQ ID NO:4). According to non-limiting theory, such substitution mutations prevent covalent attachment of glycosaminoglycan chains at these positions in the biglycan polypeptide, thereby altering its properties with respect to elastogenesis.

Variants, fragments, derivatives, truncations, and the like of such mutant biglycan polypeptides are also contemplated and are discussed in greater detail below, including routine methodologies for their production, structural characterization (e.g., for the absence of detectable GAG chains) and functional testing (e.g., for their elastogenic properties). According to certain preferred embodiments, a mutant biglycan polypeptide for use in the methods disclosed herein may comprise an amino acid sequence that has at least 80 percent, 85 percent, 90 percent, 95 percent, 96, 97, 98, 99 or greater percent sequence identity to SEQ ID NO:3 or SEQ ID NO:4.

As noted above, the present disclosure also relates in part to the unexpected observation that engineered versican V3-derived polypeptides described herein may exhibit pro-elastogenic properties despite lacking the complete hyaluronic acid (HA) binding domain, or despite lacking the complete epidermal growth factor-like (EGF) domain or the complete complement regulatory protein (CRP) domain, that is present in any pro-elastogenic versican isoform of the prior art, including V3 polypeptides described in US 2004/0213762. As such, and according to non-limiting theory, the engineered versican V3-derived polypeptides of the present invention expressly exclude any V3 polypeptides of US 2004/0213762 or of Wight et al. 2004 *Circ. Res.* 94:1158.

Exemplary pro-elastogenic engineered versican isoform V3-derived polypeptides according to the herein disclosed embodiments include polypeptides that comprise the amino acid sequences set forth in SEQ ID NOS:11, 13, 15, 17, 19, 21, 23 and 25, which may be encoded by polynucleotide sequences as set forth, for example, in SEQ ID NOS:10, 12, 14, 16, 18, 20, 22 and 24, respectively, and/or by variants and/or derivatives thereof. These and related embodiments may employ versican isoform V3-derived polypeptides having amino acid sequences as set forth in SEQ ID NOS:26 or 27.

Variants, fragments, derivatives, truncations, and the like of such engineered V3-derived polypeptides are also contemplated and are discussed in greater detail below, including routine methodologies for their production, structural characterization (e.g., for the absence of intact HA-binding domains) and functional testing (e.g., for their elastogenic properties). According to certain preferred embodiments, an engineered V3-derived polypeptide for use in the methods disclosed herein may comprise an amino acid sequence that has at least 80 percent, 85 percent, 90 percent, 95 percent, 96, 97, 98, 99 or greater percent sequence identity to any one or more of SEQ ID NOS:11, 13, 15, 17, 19, 21, 23 and 25.

As also noted above, certain other herein disclosed embodiments contemplate pro-elastogenic agents that may comprise metastatin, a hyaluronan-binding complex comprising a tryptic digest of vertebrate cartilage and including a tryptic fragment of cartilage link protein and a hyaluronan-binding region of aggrecan (HABR) polypeptide or a fragment, derivative or analogue thereof as provided herein. Determination of a HABR polypeptide in a hyaluronan-binding fraction of a vertebrate cartilage tryptic digest prepared according to art-accepted methodologies may therefore provide evidence of the presence of a metastatin preparation according to the elastogenic compositions and methods of the instant disclosure. Preparation and characterization of metastatin are described in, e.g., Liu et al. 2001 *Canc. Res.* 61:1022, and in WO99/45942.

Exemplary HABR polypeptides include polypeptides having highly conserved amino sequences across mammalian species lines, such as a polypeptide comprising any of the mammalian HABR sequences disclosed, for instance, by Barry et al. (1992 *Biochem. J.* 286:761) and including tryptic polypeptides derived therefrom, as disclosed for example in Table 1 and FIG. 2 of Barry et al. Persons familiar with the art will readily appreciate that HABR polypeptides may be detected in a hyaluronan-binding fraction of a vertebrate cartilage tryptic digest according to established methodologies (e.g., Barry et al. 1992), to provide an exemplary pro-elastogenic metastatin composition as described herein.

Additionally or alternatively, metastatin presence in a hyaluronan-binding fraction of a vertebrate cartilage tryptic digest prepared according to art-accepted methodologies may be determined by detection of a link 2 polypeptide module that may be present in a variety of hyaluronan-binding extracellular matrix proteins, including, as non-limiting examples, cartilage link protein, aggrecan, versican, CD44 and others (e.g., Barta et al., *Biochem. J.* 292:947-949 (1993); Kohda et al., *Cell* 86:767-775 (1996); Brisett et al., *FEBS Lett.* 388: 211-216 (1996); Peach et al., *J. Cell Biol.* 122:257-264 (1993)). Depending, for instance, on the source of cartilage (e.g., human, mouse, rat, bovine, chicken, chimpanzee), such detection according to established methodologies of a link 2 polypeptide such as at least one of the polypeptides having an amino acid sequence as set forth in SEQ ID NOS:28-36 and 38-41, may be used to confirm the presence of metastatin in a given preparation. Immunodetection of link 2 polypeptides, for example, is described by Caterson et al. (1985 *J. Biol. Chem.* 260:11348).

Recombinant Expression Constructs

The present invention further relates to constructs encoding pro-elastogenic proteins such as mutant biglycan polypeptides and engineered versican V3-derived polypeptides, and in particular to methods for administering recombinant constructs encoding such proteins that may be expressed, for example, as fragments, analogs and derivatives of such polypeptides. The terms "fragment," "derivative" and "analog" when referring to pro-elastogenic proteins such as mutant biglycan polypeptides and engineered versican V3-derived polypeptides, refers to any mutant biglycan or engineered versican V3-derived polypeptide described herein, or a fusion protein comprising such polypeptide, that retains essentially the same biological function or activity as such polypeptide. Thus, an analog includes a proprotein which can be activated by cleavage of the proprotein portion to produce an active pro-elastogenic polypeptide.

A fragment, derivative or analog of a pro-elastogenic mutant biglycan or engineered versican V3-derived polypeptide described herein, including polypeptides or fusion proteins encoded by the cDNAs referred to herein, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mutant biglycan or engineered versican V3-derived polypeptide, including amino acids that are employed for detection or specific functional alteration of the mutant biglycan or engineered versican V3-derived polypeptide or a proprotein sequence. Such fragments, derivatives and analogs are deemed to be within the scope of those skilled in the art from the teachings herein.

The polypeptides of the present invention include mutant biglycan or engineered versican V3-derived polypeptides and fusion proteins having amino acid sequence regions that are identical or similar to sequences known in the art, or fragments or portions thereof. For example by way of illustration and not limitation, a mutant biglycan polypeptide (e.g., SEQ ID NO:3) or an engineered versican V3-derived polypeptide (e.g., SEQ ID NOS:11, 13, 15, 17, 19, 21, 23 or 25) is contemplated for use according to the instant invention, as are polypeptides having at least 80% similarity (preferably a 80% identity) and more preferably 90% similarity (more preferably a 90% identity) to the reported polypeptide and still more preferably a 95% similarity (still more preferably a 95% identity) to the herein disclosed polypeptides and to portions of such polypeptides, wherein such portions of a mutant biglycan or engineered versican V3-derived polypeptide generally contain at least 30, 50, 70, 90 or 120 amino acids and more preferably at least 150, 175, 200, 240 or more amino acids.

As known in the art "similarity" between two polypeptides is determined by comparing the amino acid sequence and conserved amino acid substitutes thereto of the polypeptide to the sequence of a second polypeptide. Fragments or portions of the nucleic acids encoding polypeptides according to the presently disclosed embodiments may be used to synthesize full-length nucleic acids encoding a mutant biglycan polypeptide or an engineered versican V3-derived polypeptide. As used herein, "% identity" refers to the percentage of identical amino acids situated at corresponding amino acid residue positions when two or more polypeptide are aligned and their sequences analyzed using a gapped BLAST algorithm (e.g., Altschul et al., 1997 *Nucl. Ac. Res.* 25:3389) which weights sequence gaps and sequence mismatches according to the default weightings provided by the National Institutes of Health/NCBI database (Bethesda, Md.; see www.ncbi.nlm.nih.gov/cgi-bin/BLAST/nph-newblast).

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

The term "gene" means the segment of DNA involved in producing a polypeptide chain; it includes regions preceding and following the coding region "leader and trailer" as well as intervening sequences (introns) between individual coding segments (exons).

As described herein, certain invention embodiments provide mutant biglycan or engineered versican V3-derived polypeptides and fusion proteins encoded by nucleic acids that have the mutant biglycan or engineered versican V3-derived polypeptide coding sequence fused in frame to an additional fusion polypeptide encoding sequence to provide for expression of a mutant biglycan polypeptide or an engineered versican V3-derived polypeptide sequence fused to an additional functional fusion polypeptide sequence that permits, for example by way of illustration and not limitation, detection, functional alteration, isolation and/or purification of the resulting fusion protein. Such fusion proteins may permit functional alteration of a mutant biglycan or engineered versican V3-derived polypeptide by containing additional polypeptide sequences that influence behavior of the fusion product, for example by altering the availability of sufhydryl groups for participation in disulfide bond formation, for example, to influence the degree of multimerization or oligomerization that may be achieved, and/or to influence other factors contributing to ECM processes such as elastic fiber formation.

Modification of the polypeptide may be effected by any means known to those of skill in the relevant art. The preferred methods herein rely on modification of DNA encoding the fusion protein and expression of the modified DNA. DNA encoding one of the mutant biglycan or engineered versican V3-derived polypeptide fusions discussed above may be mutagenized using standard methodologies, including those described below. For example, cysteine residues that may otherwise facilitate multimer formation or promote particular molecular conformations can be deleted from a polypeptide or replaced, e.g., cysteine residues that are responsible for aggregate formation. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. In addition, fragments of mutant biglycan or engineered versican V3-derived polypeptide fusions may be constructed and used.

Conservative substitutions of amino acids are well known and may be made generally without altering the biological activity of the resulting mutant biglycan or engineered versican V3-derived polypeptide molecule. For example, such substitutions are generally made by interchanging within the groups of polar residues, charged residues, hydrophobic residues, small residues, and the like. If necessary, such substitutions may be determined empirically merely by testing the resulting modified protein for the ability to alter (i.e., increase or decrease in a statistically significant manner) elastogenesis in in vitro or in vivo biological assays, such as those described herein.

The present invention further relates to nucleic acids which hybridize to mutant biglycan or engineered versican V3-derived polypeptide encoding polynucleotide sequences as provided herein, or their complements, as will be readily apparent to those familiar with the art, if there is at least 70%, preferably 80-85%, more preferably at least 90%, and still more preferably at least 95%, 96%, 97%, 98% or 99% identity between the sequences. The present invention particularly relates to nucleic acids which hybridize under stringent conditions to the mutant biglycan or engineered versican V3-derived polypeptide encoding nucleic acids referred to herein. As used herein, the term "stringent conditions" means hybridization will occur only if there is at least 90-95% and preferably at least 97% identity between the sequences. The nucleic acids which hybridize to mutant biglycan or engineered versican V3-derived polypeptide encoding nucleic acids referred to herein, in preferred embodiments, encode polypeptides which retain substantially the same biological function or activity (e.g., promoting elastogenesis) as the mutant biglycan or engineered versican V3-derived polypeptides described herein.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically "high", "medium" and "low" stringency encompass the following conditions or equivalent conditions thereto: high stringency: 0.1×SSPE or SSC, 0.1% SDS, 65° C.; medium stringency: 0.2×SSPE or SSC, 0.1% SDS, 50° C.; and low stringency: 1.0×SSPE or SSC, 0.1% SDS, 50° C. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

The nucleic acids of the present invention, also referred to herein as polynucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes a mutant biglycan or engineered versican V3-derived polypeptide for use according to certain invention embodiments may contain sequence regions that are identical to portions of, respectively, the biglycan or versican coding sequences known in the art, or may for such reasons have a different coding sequence, which, as a result of the redundancy or degeneracy of the genetic code, encodes the same regions of such a biglycan or V3 polypeptide.

The nucleic acids which encode mutant biglycan or engineered versican V3-derived polypeptides for use according to certain invention embodiments may include, but are not limited to: only the coding sequence for the mutant biglycan or engineered versican V3-derived polypeptide; the coding sequence for the mutant biglycan or engineered versican V3-derived polypeptide and additional coding sequence; the coding sequence for the mutant biglycan or engineered versican V3-derived polypeptide (and optionally additional coding sequence) and non-coding sequence, such as introns or non-coding sequences 5' and/or 3' of the coding sequence for the mutant biglycan or engineered versican V3-derived polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding" or "polynucleotide encoding" a mutant biglycan or engineered versican V3-derived polypeptide encompasses a nucleic acid which includes only coding sequence for a mutant biglycan or engineered versican V3-derived polypeptide as well as a nucleic acid which includes additional coding and/or non-coding sequence(s).

Nucleic acids and oligonucleotides for use as described herein can be synthesized by any method known to those of skill in this art (see, e.g., WO 93/01286, U.S. application Ser. No. 07/723,454; U.S. Pat. No. 5,218,088; U.S. Pat. No. 5,175,269; U.S. Pat. No. 5,109,124). Identification of oligonucleotides and nucleic acid sequences for use in the present invention involves methods well known in the art. For example, the desirable properties, lengths and other characteristics of useful oligonucleotides are well known. In certain embodiments, synthetic oligonucleotides and nucleic acid sequences may be designed that resist degradation by endogenous host cell nucleolytic enzymes by containing such linkages as: phosphorothioate, methylphosphonate, sulfone, sulfate, ketyl, phosphorodithioate, phosphoramidate, phosphate esters, and other such linkages that have proven useful in antisense applications (see, e.g., Agrwal et al., *Tetrehedron Lett.* 28:3539-3542 (1987); Miller et al., *J. Am. Chem. Soc.* 93:6657-6665 (1971); Stec et al., *Tetrehedron Lett.* 26:2191-2194 (1985); Moody et al., *Nucl. Acids Res.* 12:4769-4782 (1989); Uznanski et al., *Nucl. Acids Res.* (1989); Letsinger et al., *Tetrahedron* 40:137-143 (1984); Eckstein, *Annu. Rev. Biochem.* 54:367-402 (1985); Eckstein, *Trends Biol. Sci.* 14:97-100 (1989); Stein In: *Oligodeoxynucleotides. Antisense Inhibitors of Gene Expression*, Cohen, Ed, Macmillan Press, London, pp. 97-117 (1989); Jager et al., *Biochemistry* 27:7237-7246 (1988)).

In one embodiment, the present invention provides truncated components (e.g., fragments of a mutant biglycan or engineered versican V3-derived polypeptide) for use in a mutant biglycan or engineered versican V3-derived polypeptide fusion protein, and in another embodiment the invention provides nucleic acids encoding a mutant biglycan or engineered versican V3-derived polypeptide fusion protein having such truncated components. A truncated molecule may be any molecule that comprises less than a full length version of the molecule. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences.

In other preferred embodiments, truncated molecules are polypeptides that comprise less than the full length amino acid sequence of a particular protein or polypeptide component. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues, including deletions of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41-50, 51-74, 75-100, 101-150, 151-200, 201-250 or 251-299 contiguous nucleotide or amino acid residues. In certain particularly preferred embodiments truncated nucleic acid molecules may have a deletion of 270-330 contiguous nucleotides. In certain other particularly preferred embodiments truncated polypeptide molecules may have a deletion of 80-140 contiguous amino acids. In certain related embodiments a truncated biglycan or mutant biglycan comprises a deletion at the carboxyl or C-terminus of the biglycan polypeptide (or the polynucleotide sequence encoding such polypeptide), and in certain other related embodiments a truncated biglycan comprises a deletion at the amino or N-terminus of the biglycan polypeptide (or the polynucleotide sequence encoding such polypeptide), including an N-terminal deletion whereby the amino acid at position 5 of SEQ ID NO:4 and/or the amino acid at position 10 of SEQ ID NO:4 is deleted.

The present invention further relates to variants of the herein referenced nucleic acids which encode fragments, analogs and/or derivatives of a mutant biglycan or engineered versican V3-derived polypeptide. The variants of the nucleic acids encoding mutant biglycan or engineered versican V3-derived polypeptides may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded mutant biglycan or engineered versican V3-derived polypeptide.

Variants and derivatives of mutant biglycan or engineered versican V3-derived polypeptides may be obtained by mutations of nucleotide sequences encoding mutant biglycan or engineered versican V3-derived polypeptides or any portion thereof. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, Jan. 1985, 12-19); Smith et al. (*Genetic Engineering: Principles and Methods BioTechniques*, Jan. 1985, 12-19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462.

As an example, modification of DNA may be performed by site-directed mutagenesis of DNA encoding the protein combined with the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (e.g., all or a component portion of a given mutant biglycan or engineered versican V3-derived polypeptide). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Equivalent DNA constructs that encode various additions or substitutions of amino acid residues or sequences, or deletions of terminal or internal residues or sequences not needed for biological activity are also encompassed by the invention. For example, and as discussed above, sequences encoding Cys residues that are not desirable or essential for biological activity can be altered to cause the Cys residues to be deleted or replaced with other amino acids, preventing formation of incorrect intramolecular disulfide bridges upon renaturation.

Host organisms include those organisms in which recombinant production of mutant biglycan or engineered versican V3-derived polypeptide products encoded by the recombinant constructs of certain presently disclosed invention embodiments may occur, such as bacteria (for example, *E. coli*), yeast (for example, *Saccharomyces cerevisiae* and *Pichia pastoris*), insect cells and mammals, including in vitro and in vivo expression. Host organisms thus may include organisms for the construction, propagation, expression or other steps in the production of the compositions provided herein; hosts may also include subjects in which elastogenesis takes place. Presently preferred host organisms are *E. coli* bacterial strains, inbred murine strains and murine cell lines, and human cells, subjects and cell lines.

The DNA construct encoding the desired mutant biglycan or engineered versican V3-derived polypeptide is introduced into a plasmid for expression in an appropriate host. In certain preferred embodiments, the host is a bacterial host. The sequence encoding the ligand or nucleic acid binding domain is preferably codon-optimized for expression in the particular host. Thus, for example, if a human mutant biglycan or engineered versican V3-derived polypeptide is expressed in bacteria, the codons would be optimized for bacterial usage. For small coding regions, the gene can be synthesized as a single oligonucleotide. For larger proteins, splicing of multiple oligonucleotides, mutagenesis, or other techniques known to those in the art may be used. The sequences of nucleotides in the plasmids that are regulatory regions, such as promoters and operators, are operationally associated with one another for transcription. The sequence of nucleotides encoding a mutant biglycan or engineered versican V3-derived polypeptide may also include DNA encoding a secretion signal, whereby the resulting peptide is a precursor protein. The resulting processed protein may be recovered from the periplasmic space or the fermentation medium.

In preferred embodiments, the DNA plasmids also include a transcription terminator sequence. As used herein, a "transcription terminator region" is a sequence that signals transcription termination. The entire transcription terminator may be obtained from a protein-encoding gene, which may be the same or different from the inserted mutant biglycan or engineered versican V3-derived polypeptide encoding gene or the source of the promoter. Transcription terminators are optional components of the expression systems herein, but are employed in preferred embodiments.

The plasmids used herein include a promoter in operative association with the DNA encoding the protein or polypeptide of interest and are designed for expression of proteins in a suitable host as described above (e.g., bacterial, murine or human) depending upon the desired use of the plasmid (e.g., administration of a mutant biglycan or engineered versican V3-derived polypeptide, or, alternatively or additionally, administration of a recombinant expression construct comprising a promoter operably linked to a polynucleotide sequence that encodes a mutant biglycan or engineered versican V3-derived polypeptide, for instance, in a viral vector). Suitable promoters for expression of proteins and polypeptides herein are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, and lac promoters, such as the lacUV5, from *E. coli*; the P10 or polyhedrin gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems. For expression of the proteins such promoters are inserted in a plasmid in operative linkage with a control region such as the lac operon.

Preferred promoter regions are those that are inducible and functional in *E. coli*. Examples of suitable inducible promoters and promoter regions include, but are not limited to: the *E. coli* lac operator responsive to isopropyl β-D-thiogalactopyranoside (IPTG; see Nakamura et al., *Cell* 18:1109-1117, 1979); the metallothionein promoter metal-regulatory-elements responsive to heavy-metal (e.g., zinc) induction (see, e.g., U.S. Pat. No. 4,870,009 to Evans et al.); the phage T7lac promoter responsive to IPTG (see, e.g., U.S. Pat. No. 4,952,496; and Studier et al., *Meth. Enzymol.* 185:60-89, 1990) and the TAC promoter.

The plasmids may optionally include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene (Amp$^r$), tetracycline resistance gene (Tc$^r$) and the kanamycin resistance gene (Kan$^r$).

The plasmids may also include DNA encoding a signal for secretion of the operably linked protein. Secretion signals suitable for use are widely available and are well known in the art. Prokaryotic and eukaryotic secretion signals functional in *E. coli* may be employed. The presently preferred secretion signals include, but are not limited to, those encoded by the following *E. coli* genes: ompA, ompT, ompF, ompC, beta-lactamase, and alkaline phosphatase, and the like (von Heijne, *J. Mol. Biol.* 184:99-105, 1985). In addition, the bacterial pelB gene secretion signal (Lei et al., *J. Bacteria* 169: 4379, 1987), the phoA secretion signal, and the cek2 functional in insect cell may be employed. The most preferred secretion signal is the *E. coli* ompA secretion signal. Other prokaryotic and eukaryotic secretion signals known to those of skill in the art may also be employed (see, e.g., von Heijne, *J. Mol. Biol.* 184:99-105, 1985), as may also be a fusion domain comprising the *E. coli* YebF carrier protein (Zhang et al., 2006 *Nat. Biotechnol.* 24:100). Using the methods described herein, one of skill in the art can substitute secretion signals that are functional in yeast, insect or mammalian cells to secrete proteins from those cells.

Preferred plasmids for transformation of *E. coli* cells include the pET expression vectors (e.g., pET-11a, pET-12a-c, pET-15b; see U.S. Pat. No. 4,952,496; available from Novagen, Madison, Wis.). Other preferred plasmids include the pKK plasmids, particularly pKK 223-3, which contains the tac promoter (Brosius et al., *Proc. Natl. Acad. Sci.* 81:6929, 1984; Ausubel et al., *Current Protocols in Molecular Biology*; U.S. Pat. Nos. 5,122,463, 5,173,403, 5,187,153, 5,204,254, 5,212,058, 5,212,286, 5,215,907, 5,220,013, 5,223,483, and 5,229,279). Plasmid pKK has been modified by replacement of the ampicillin resistance gene with a kanamycin resistance gene. (Available from Pharmacia; obtained from pUC4K, see, e.g., Vieira et al. (*Gene* 19:259-268, 1982; and U.S. Pat. No. 4,719,179.) Baculovirus vectors, such as pBlueBac (also called pJVETL and derivatives thereof), particularly pBlueBac III (see, e.g., U.S. Pat. Nos. 5,278,050, 5,244,805, 5,243,041, 5,242,687, 5,266,317, 4,745,051, and 5,169,784; available from Invitrogen, San Diego) may also be used for expression of the polypeptides in insect cells. Other plasmids include the pIN-IIIompA plasmids (see U.S. Pat. No. 4,575,013; see also Duffaud et al., *Meth. Enz.* 153:492-507, 1987), such as pIN-IIIompA2.

Preferably, the DNA molecule is replicated in bacterial cells, preferably in *E. coli*. The preferred DNA molecule also includes a bacterial origin of replication, to ensure the maintenance of the DNA molecule from generation to generation of the bacteria. In this way, large quantities of the DNA molecule can be produced by replication in bacteria. Preferred bacterial origins of replication include, but are not limited to, the f1-ori and col E1 origins of replication. Preferred hosts contain chromosomal copies of DNA encoding T7 RNA polymerase operably linked to an inducible promoter, such as the lacUV promoter (see U.S. Pat. No. 4,952, 496). Such hosts include, but are not limited to, lysogens *E. coli* strains HMS174(DE3)pLysS, BL21(DE3)pLysS, HMS174(DE3) and BL21(DE3). Strain BL21(DE3) is preferred. The pLys strains provide low levels of T7 lysozyme, a natural inhibitor of T7 RNA polymerase.

The DNA molecules provided may also contain a gene coding for a repressor protein. The repressor protein is capable of repressing the transcription of a promoter that contains sequences of nucleotides to which the repressor protein binds. The promoter can be derepressed by altering the physiological conditions of the cell. For example, the alteration can be accomplished by adding to the growth medium a molecule that inhibits the ability to interact with the operator or with regulatory proteins or other regions of the DNA or by altering the temperature of the growth media. Preferred repressor proteins include, but are not limited to the *E. coli* lacI repressor responsive to IPTG induction, the temperature sensitive λ cI857 repressor, and the like. The *E. coli* lacI repressor is preferred.

In general, recombinant constructs of the subject invention will also contain elements necessary for transcription and translation. In particular, such elements are preferred where the recombinant expression construct containing nucleic acid sequences encoding mutant biglycan or engineered versican V3-derived polypeptides is intended for expression in a host cell or organism. In certain embodiments of the present invention, cell type preferred or cell type specific expression of a mutant biglycan or engineered versican V3-derived polypeptide encoding gene may be achieved by placing the gene under regulation of a promoter. The choice of the promoter will depend upon the cell type to be transformed and the degree or type of control desired. Promoters can be constitutive or active and may further be cell type specific, tissue specific, individual cell specific, event specific, temporally specific or inducible. Cell-type specific promoters and event type specific promoters are preferred. Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), and adenovirus promoter. In addition to viral promoters, cellular promoters are also amenable within the context of this invention. In particular, cellular promoters for the so-called housekeeping genes are useful. Viral promoters are preferred, because generally they are stronger promoters than cellular promoters. Promoter regions have been identified in the genes of many eukaryotes including higher eukaryotes, such that suitable promoters for use in a particular host can be readily selected by those skilled in the art.

Inducible promoters may also be used. These promoters include MMTV LTR (PCT WO 91/13160), inducible by dexamethasone; metallothionein promoter, inducible by heavy metals; and promoters with cAMP response elements, inducible by cAMP. By using an inducible promoter, the nucleic acid sequence encoding a mutant biglycan or engineered versican V3-derived polypeptide may be delivered to a cell by the subject invention expression construct and will remain quiescent until the addition of the inducer. This allows further control on the timing of production of the gene product.

Event-type specific promoters are active or up-regulated only upon the occurrence of an event, such as tumorigenicity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed may be used when expression of a particular mutant biglycan or engineered versican V3-derived polypeptide-encoding gene is desired in concert with expression of one or more additional endogenous or exogenously introduced genes. This type of promoter is especially useful when one knows the pattern of gene expression relevant to induction of an elastogenic response in a particular tissue where de novo elastin fiber formation is desired, so that specific cells that are capable of elastogenesis within that tissue may be activated or otherwise recruited to participate in the elastogenic response.

In addition to the promoter, repressor sequences, negative regulators, or tissue-specific silencers may be inserted to reduce non-specific expression of mutant biglycan or engineered versican V3-derived polypeptide encoding genes in certain situations, such as, for example, a host in which it may be desired transiently and/or tissue-specifically or site-specifically to compromise elastin fiber formation as part of a therapeutic strategy. Multiple repressor elements may be inserted in the promoter region. Repression of transcription is independent on the orientation of repressor elements or distance from the promoter. One type of repressor sequence is an insulator sequence. Such sequences inhibit transcription (Dunaway et al., *Mol Cell Biol* 17: 182-9, 1997; Gdula et al., *Proc Natl Acad Sci USA* 93:9378-83, 1996, Chan et al., *J Virol* 70: 5312-28, 1996; Scott and Geyer, *EMBO J* 14:6258-67, 1995; Kalos and Fournier, *Mol Cell Biol* 15:198-207, 1995; Chung et al., *Cell* 74: 505-14, 1993) and will silence background transcription.

Repressor elements have also been identified in the promoter regions of the genes for type II (cartilage) collagen, choline acetyltransferase, albumin (Hu et al., *J. Cell Growth Differ.* 3(9):577-588, 1992), phosphoglycerate kinase (PGK-2) (Misuno et al., *Gene* 119(2):293-297, 1992), and in the 6-phosphofructo-2-kinase/fructose-2,6-bisphosphatase gene. (Lemaigre et al., *Mol. Cell Biol.* 11(2):1099-1106.) Furthermore, the negative regulatory element Tse-1 has been identified in a number of liver specific genes, and has been shown to block cAMP response element-(CRE) mediated induction of gene activation in hepatocytes. (Boshart et al., *Cell* 61(5):905-916, 1990).

In preferred embodiments, elements that increase the expression of the desired product are incorporated into the construct. Such elements include internal ribosome binding sites (IRES; Wang and Siddiqui, *Curr. Top. Microbiol. Immunol* 203:99, 1995; Ehrenfeld and Semler, *Curr. Top. Microbiol. Immunol.* 203:65, 1995; Rees et al., *Biotechniques* 20:102, 1996; Sugimoto et al., *Biotechnology* 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA, western blot, immunocytochemistry or other well known techniques.

Other elements may be incorporated into the mutant biglycan or engineered versican V3-derived polypeptide encoding constructs of the present invention. In preferred embodiments, the construct includes a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary for, or that enhance, propagation in bacteria are incorporated. Such elements include an origin of replication, a selectable marker and the like.

As provided herein, an additional level of controlling the expression of nucleic acids encoding mutant biglycan or engineered versican V3-derived polypeptide delivered to cells using the constructs of the invention may be provided by simultaneously delivering two or more differentially regulated nucleic acid constructs. The use of such a multiple nucleic acid construct approach may permit coordinated regulation of an elastogenic response such as, for example, spatiotemporal coordination that depends on the cell type and/or presence of another expressed encoded component (e.g., one or more additional ECM components such as elastic fiber protein constituents). Those familiar with the art will appreciate that multiple levels of regulated gene expression may be achieved in a similar manner by selection of suitable regulatory sequences, including but not limited to promoters, enhancers and other well known gene regulatory elements.

The present invention also relates to vectors, and to constructs prepared from known vectors that include nucleic acids of the present invention, and in particular to "recombinant expression constructs" that include any nucleic acids encoding mutant biglycan or engineered versican V3-derived polypeptides according to certain invention embodiments as provided above; to host cells which are genetically engineered with vectors and/or constructs of the invention and to methods of administering expression constructs comprising nucleic acid sequences encoding such mutant biglycan or engineered versican V3-derived polypeptide and fusion proteins of these and related invention embodiments, or fragments or variants thereof, by recombinant techniques. Mutant biglycan or engineered versican V3-derived polypeptides can be expressed in virtually any host cell under the control of appropriate promoters, depending on the nature of the construct (e.g., type of promoter, as described above), and on the nature of the desired host cell (e.g., whether postmitotic terminally differentiated or actively dividing; e.g., whether the expression construct occurs in a host cell as an episome or is integrated into the host cell genome). Appropriate cloning and expression vectors for use with prokaryotic and eukaryotic hosts are described by Sambrook, et al., *Molecular Cloning: A Laboratory Manual*, Third Edition, Cold Spring Harbor, N.Y., (2001); as noted above, in particularly preferred embodiments of the invention, recombinant expression is conducted in mammalian cells that have been transfected or transformed with the herein described recombinant expression construct.

Typically, the constructs are derived from plasmid vectors. A preferred construct is a modified pNASS vector (Clontech, Palo Alto, Calif.), which has nucleic acid sequences encoding an ampicillin resistance gene, a polyadenylation signal and a T7 promoter site. Other suitable mammalian expression vectors are well known (see, e.g., Ausubel et al., 1995; Sambrook et al., supra; see also, e.g., catalogues from Invitrogen, San Diego, Calif.; Novagen, Madison, Wis.; Pharmacia, Piscataway, N.J.; and others). Presently preferred constructs may be prepared that include a dihydrofolate reductase (DHFR) encoding sequence under suitable regulatory control, for promoting enhanced production levels of the mutant biglycan or engineered versican V3-derived polypeptides, which levels result from gene amplification following application of an appropriate selection agent (e.g., methetrexate).

Generally, recombinant expression vectors will include origins of replication and selectable markers permitting transformation of the host cell, and a promoter derived from a highly-expressed gene to direct transcription of a downstream structural sequence, as described above. The heterologous structural sequence is assembled in appropriate phase with translation initiation and termination sequences. Thus, for example, the mutant biglycan or engineered versican V3-derived polypeptide encoding nucleic acids as provided herein may be included in any one of a variety of expression vector constructs as a recombinant expression construct for expressing a mutant biglycan or engineered versican V3-derived polypeptide in a host cell. In certain preferred embodiments the constructs are included in formulations that are administered in vivo. Such vectors and constructs include chromosomal, nonchromosomal and synthetic DNA sequences, e.g., derivatives of SV40; bacterial plasmids; phage DNA; yeast plasmids; vectors derived from combinations of plasmids and phage DNA, viral DNA, such as from vaccinia virus, adenovirus, adeno-associated virus, herpesvirus, lentivirus, fowl pox or other poxvirus, retrovirus and/or pseudorabies, or replication deficient retroviruses as described below. However, any other vector may be used for preparation of a recombinant expression construct, and in preferred embodiments such a vector will be replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (2004 *Current Protocols in Molecular Biology*, John Wiley & Sons, Inc., Boston, Mass.); Sambrook et al. (2001 *Molecular Cloning*, Third Ed., Cold Spring Harbor Laboratory, Plainview, N.Y.); Maniatis et al. (1982 Molecular Cloning, Cold Spring Harbor Laboratory, Plainview, N.Y.); Glover (Ed.) (1985 *DNA Cloning Vol. I and II*, IRL Press, Oxford, UK); Hames and Higgins (Eds.), (1985 *Nucleic Acid Hybridization*, IRL Press, Oxford, UK); and elsewhere.

The DNA sequence in the expression vector is operatively linked to at least one appropriate expression control sequences (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a mutant biglycan or engineered versican V3-derived polypeptide is described herein.

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers.

As provided herein, in certain embodiments the vector may be a viral vector such as a retroviral vector. (Miller et al., 1989 *BioTechniques* 7:980; Coffin and Varmus, 1996 Retroviruses, Cold Spring Harbor Laboratory Press, NY.) For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

Retroviruses are RNA viruses which can replicate and integrate into the genome of a host cell via a DNA intermediate. This DNA intermediate, or provirus, may be stably integrated into the host cell DNA. According to certain embodiments of the present invention, an expression construct may comprise a retrovirus into which a foreign gene that encodes a foreign protein is incorporated in place of normal retroviral RNA. When retroviral RNA enters a host cell coincident with infection, the foreign gene is also introduced into the cell, and may then be integrated into host cell DNA as if it were part of the retroviral genome. Expression of this foreign gene within the host results in expression of the foreign protein.

Most retroviral vector systems which have been developed for gene therapy are based on murine retroviruses. Such retroviruses exist in two forms, as free viral particles referred to as virions, or as proviruses integrated into host cell DNA. The virion form of the virus contains the structural and enzymatic proteins of the retrovirus (including the enzyme reverse transcriptase), two RNA copies of the viral genome, and portions of the source cell plasma membrane containing viral envelope glycoprotein. The retroviral genome is organized into four main regions: the Long Terminal Repeat (LTR), which contains cis-acting elements necessary for the initiation and termination of transcription and is situated both 5' and 3' of the coding genes, and the three coding genes gag, pol, and env. These three genes gag, pol, and env encode, respectively, internal viral structures, enzymatic proteins (such as integrase), and the envelope glycoprotein (designated gp70 and p15e) which confers infectivity and host range specificity of the virus, as well as the "R" peptide of undetermined function.

Separate packaging cell lines and vector producing cell lines have been developed because of safety concerns regarding the uses of retroviruses, including their use in expression constructs as provided by the present invention. Briefly, this methodology employs the use of two components, a retroviral vector and a packaging cell line (PCL). The retroviral vector contains long terminal repeats (LTRs), the foreign DNA to be transferred and a packaging sequence (y). This retroviral vector will not reproduce by itself because the genes which encode structural and envelope proteins are not included within the vector genome. The PCL contains genes encoding the gag, pol, and env proteins, but does not contain the packaging signal "y". Thus, a PCL can only form empty virion particles by itself. Within this general method, the retroviral vector is introduced into the PCL, thereby creating a vector-producing cell line (VCL). This VCL manufactures virion particles containing only the retroviral vector's (foreign) genome, and therefore has previously been considered to be a safe retrovirus vector for therapeutic use.

"Retroviral vector construct" refers to an assembly which is, within preferred embodiments of the invention, capable of directing the expression of a sequence(s) or gene(s) of interest, such as mutant biglycan or engineered versican V3-derived polypeptide encoding nucleic acid sequences. Briefly, the retroviral vector construct must include a 5' LTR, a tRNA binding site, a packaging signal, an origin of second strand DNA synthesis and a 3' LTR. A wide variety of heterologous sequences may be included within the vector construct, including for example, a sequence which encodes a protein (e.g., a desired supplementary gene or a replacement gene), or which is itself useful as a transcribed molecule (e.g., as a ribozyme or antisense sequence).

Retroviral vector constructs of the present invention may be readily constructed from a wide variety of retroviruses, including for example, B, C, and D type retroviruses as well as spumaviruses and lentiviruses (see, e.g., RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Any of the above retroviruses may be readily utilized in order to assemble or construct retroviral vector constructs, packaging cells, or producer cells of the present invention given the disclosure provided herein, and standard recombinant techniques (e.g., Sambrook et al, *Molecular Cloning: A Laboratory Manual,* 2d ed., Cold Spring Harbor Laboratory Press, 1989; Kunkle, *PNAS* 82:488, 1985).

Suitable promoters for use in viral vectors generally may include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein, and may be from among either regulated promoters or promoters as described above.

As described above, the retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* 1:5-14 (1990). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the mutant biglycan or engineered versican V3-derived polypeptides or fusion proteins. Such retroviral vector particles then may be employed, to transduce eukaryotic cells, either in vitro or in vivo. The transduced eukaryotic cells will express the nucleic acid sequence(s) encoding the mutant biglycan or engineered versican V3-derived polypeptide or fusion protein. Eukaryotic cells which may be transduced include, in preferred embodiments, smooth muscle cells (e.g., vascular smooth muscle cells including arterial smooth muscle cells and venous smooth muscle cells, gastrointestinal tract smooth muscle cells, respiratory tract smooth muscle cells, urogenital tract smooth muscle cells), fibroblasts, myofibroblasts, chondrocytes, pericytes, glial cells, glioma cells, macrophages, and endothelial cells, but the invention is not intended to be so limited such that cells to be transduced may in certain embodiments also include, for example, embryonic stem cells, as well as hematopoietic stem cells, hepatocytes, fibroblasts, circulating peripheral blood mononuclear and polymorphonuclear cells including myelomonocytic cells, lymphocytes, myoblasts, tissue macrophages, dendritic cells, Kupffer cells, lymphoid and reticuloendothelia cells of the lymph nodes and spleen, keratinocytes, endothelial cells, and bronchial epithelial cells.

As another example of an embodiment of the invention in which a viral vector is used to prepare the recombinant mutant biglycan or engineered versican V3-derived polypeptide encoding expression construct, in one preferred embodiment, host cells transduced by a recombinant viral construct directing the expression of mutant biglycan or engineered versican V3-derived polypeptides may produce viral particles containing expressed mutant biglycan or engineered versican V3-derived polypeptides that are derived from portions of a host cell membrane incorporated by the viral particles during viral budding.

In another aspect, the present invention relates to host cells containing the above described recombinant mutant biglycan or engineered versican V3-derived polypeptide encoding expression constructs. Host cells are genetically engineered (transduced, transformed or transfected) with the vectors and/or expression constructs of these and related invention embodiments which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding mutant biglycan or engineered versican V3-derived polypeptides. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of mutant biglycan or engineered versican V3-derived polypeptide encoding expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

Certain embodiments provided herein relate to methods for promoting elastogenesis in a cell that is capable of elastogenesis, and for treating a condition associated with inadequate elastin fiber formation as provided herein. These and related methods may comprise one or more steps of contacting, exposing, administering or otherwise introducing to a cell that is capable of elastogenesis, or to a subject having or suspected of being at risk for having a condition associated with inadequate elastin fiber formation, an effective amount of a pro-elastogenic agent (e.g., a mutant biglycan polypeptide or an engineered V3-derived polypeptide or a recombinant expression construct encoding same, or metastatin) under conditions and for a time sufficient to promote elastogenesis. As described above, elastogenesis results in a detectable and statistically significant increase in elastin fiber formation according to accepted criteria and methodologies that may vary according to the specific application of the method, for example, by northern blot analysis for increased transcription of tropoelastin-encoding mRNA, by immunohistochemical detection of increased elastin fibers in a sample from a cultured cell or from a subject, by western immunoblot analysis for one or more elastin fiber protein components in a sample from a culture cell or from a subject, or by other criteria as will be known to those familiar with the relevant art. It will be evident to those skilled in the art that the number and frequency of administrations will be dependent upon the response of the cell that is capable of elastogenesis (or upon the resulting evidence of induced elastogenesis in the subject), from which may be determined what is an effective amount.

The presently disclosed mutant biglycan or engineered versican V3-derived polypeptides, or compositions comprising one or more polynucleotides encoding same as described herein, (for example, to be administered under conditions and for a time sufficient to permit expression of a mutant biglycan or engineered versican V3-derived polypeptide in a host cell in vivo or in vitro), may be formulated into pharmaceutical compositions for administration according to well known methodologies. Pharmaceutical compositions generally comprise one or more recombinant expression constructs, and/or expression products of such constructs, in combination with a pharmaceutically acceptable carrier, excipient or diluent. Such carriers will be nontoxic to recipients at the dosages and concentrations employed. For nucleic acid-based formulations, or for formulations comprising expression products of the subject invention recombinant constructs, about 0.01 µg/kg to about 100 mg/kg body weight will be adminstered, typically by the intradermal, subcutaneous, intramuscular or intravenous route, or by other routes. A preferred dosage is about 1 µg/kg to about 1 mg/kg, with about 5 µg/kg to about 200 µg/kg particularly preferred. It will be evident to those skilled in the art that the number and frequency of administration will be dependent upon the response of the host. "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The pharmaceutical compositions that contain one or more mutant biglycan or engineered versican V3-derived polypeptide encoding constructs (or their expressed products) may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more mutant biglycan or engineered versican V3-derived polypeptide encoding construct or expressed product, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

It may also be desirable to include other components in the preparation, such as delivery vehicles including but not limited to aluminum salts, water-in-oil emulsions, biodegradable oil vehicles, oil-in-water emulsions, biodegradable microcapsules, and liposomes. Examples of immunostimulatory substances (adjuvants) for use in such vehicles include N-acetylmuramyl-L-alanine-D-isoglutamine (MDP), lipopoly-saccharides (LPS), glucan, IL-12, GM-CSF, gamma interferon and IL-15.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

As described above, the subject invention includes compositions capable of delivering nucleic acid molecules encoding mutant biglycan or engineered versican V3-derived polypeptides. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. No. 4,769,330; U.S. Pat. No. 5,017,487; and WO 89/01973)), recombinant expression construct nucleic acid molecules complexed to a polycationic molecule (see WO 93/03709), and nucleic acids associated with liposomes (see Wang et al., *Proc. Natl. Acad. Sci. USA* 84:7851, 1987). In certain embodiments, the DNA may be linked to killed or inactivated adenovirus (see Curiel et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264:16985-16987, 1989) and lipid-DNA combinations (see Felgner et al., *Proc. Natl. Acad. Sci. USA* 84:7413-7417, 1989).

In addition to direct in vivo procedures, ex vivo procedures may be used in which cells are removed from a host, modified, and placed into the same or another host animal. It will be evident that one can utilize any of the compositions noted above for introduction of mutant biglycan or engineered versican V3-derived polypeptides or of mutant biglycan or engineered versican V3-derived polypeptide encoding nucleic acid molecules into tissue cells in an ex vivo context. Protocols for viral, physical and chemical methods of uptake are well known in the art.

Accordingly, the present invention is useful for treating a patient having, or suspected of being at risk for having, a condition associated with inadequate elastin fiber formation, or for treating a cell culture derived from such a patient. As used herein, the term "patient" refers to any warm-blooded animal, preferably a human. A patient may be afflicted with emphysema, chronic obstructive pulmonary disease, idiopathic pulmonary fibrosis, lymphangio-leiomyomatosis, atherosclerosis, aneurysm, aortic dissection or restenosis, cutis laxa, pseudoxanthoma elasticum, a pelvic floor disorder, cardiac valvular disease or bicuspid aortic valve, coarctation (narrowing) of the aorta, or may be pregnant or suffering from inadequate elastin fiber formation subsequent to pregnancy, or may suffer from an aging-associated condition including a condition that results in wrinkled skin, or the patient may in the alternative be normal (i.e., free of detectable disease or of a condition associated with inadequate elastin fiber formation, including any of the aforementioned conditions). See, e.g., Lapiere CM and Krieg T (eds.), *Connective Tissue Diseases of the Skin,* 1993 Marcel Dekker, NY; *Mixed Connective Tissue Disease,* 2004 ICON Health Publications, London; Belch J J F and Zurier R B (eds.), *Connective Tissue Diseases,* 1995 Chapman and Hall, London and Boca Raton, Fla.; Royce P M and Steinmann B (eds.), *Connective Tissue and Its Heritable Disorders: Molecular, Genetic and Medical Aspects—$2^{nd}$ Ed.,* 2002, Wiley-Liss, NY; Beighton P (Ed.), McKusick's Heritable Disorders of Connective Tissue—$5^{th}$ Ed., 1993, C.V. Mosby Co., St. Louis, Mo.; and Rimoin et al., *Emery and Rimoin's Principles and Practice of Medical Genetics*—$4^{th}$ *Ed.,* 2001, Churchill Livingstone/Elsevier, N.Y. Descriptions of particular relevance to reported deficiencies in elastic fiber formation may also include Hinek et al., 2004 *Am J Pathol.* 164:119; Hinek, 2003 *Ann. Diagnost. Pediatr. Pathol.* 7:7-14; Mochizuki et al., 2002 *J. Biol. Chem.* 277:44854; Urban et al., 2002 *Am. J. Hum. Genet.* 71:30-44; Hinek et al., 2000 *Am. J. Hum. Genet.* 67:23-36; Hinek et al., 2000 *Am J. Hum. Genet.* 66:859; and Hinek et al., 2000 *Am. J. Pathol.* 156:925-938.

A "cell culture" includes any preparation amenable to ex vivo treatment, for example a preparation containing a cell that is capable of elastogenesis, including in certain preferred and non-limiting embodiments a smooth muscle cell (e.g., vascular smooth muscle cells including arterial smooth muscle cells and venous smooth muscle cells, gastrointestinal tract smooth muscle cells, respiratory tract smooth muscle cells, urogenital tract smooth muscle cells), a fibroblast, a myofibroblast, a chondrocyte, a pericyte, a glial cell, a glioma cell, a macrophage, and an endothelial cell, or another cell type such as cell types described above. Such cells may be isolated by any of a variety of techniques well known to those of ordinary skill in the art (e.g., biopsy, tissue dissociation, tissue explant, primary culture, establishment of a cell line, Ficoll-hypaque density centrifugation, etc.). The cells may (but need not) have been isolated from a patient afflicted with a condition associated with inadequate elastin fiber formation, and may be reintroduced into a patient after treatment.

A liquid composition intended for either parenteral or oral administration should contain an amount of mutant biglycan or engineered versican V3-derived polypeptide encoding construct or expressed product such that a suitable dosage will be obtained. Typically, this amount is at least 0.01 wt % of a mutant biglycan or engineered versican V3-derived polypeptide encoding construct or expressed product in the composition. When intended for oral administration, this amount may be varied to be between 0.1 and about 70% of the weight of the composition. Preferred oral compositions contain between about 4% and about 50% of mutant biglycan or engineered versican V3-derived polypeptide encoding construct or expressed product(s). Preferred compositions and preparations are prepared so that a parenteral dosage unit contains between 0.01 to 1% by weight of active compound.

The pharmaceutical composition comprising agents for promoting elastogenesis as provided herein, such as mutant biglycan or engineered versican V3-derived polypeptide or a recombinant expression construct encoding the same, or a metastatin preparation, may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the mutant biglycan or engineered versican V3-derived polypeptide encoding construct or expressed product of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In certain other related embodied methods of the invention, the mutant biglycan or engineered versican V3-derived polypeptide encoding constructs or expressed product(s) may be administered through use of insert(s), bead(s), timed-release formulation(s), patch(es) or fast-release formulation(s).

The following Examples are presented by way of illustration and not limitation.

EXAMPLES

Example 1

Promotion of Elastogenesis by Mutant Biglycan Lacking GAG

This example describes mutation of the two GAG attachment sites on the core protein of human biglycan to preclude GAG chain attachment to the biglycan polypeptide. Using the retroviral vector LXSN, cultured rat smooth muscle cells were transduced with the mutated human biglycan, as well as normal (i.e., non-mutated at amino acid positions corresponding to serines at positions 5 and 10 in human biglycan, and thus capable of covalent GAG attachment) human biglycan and the empty vector as an additional control. Following characterization of the retrovirally modified cells in culture, the cells were seeded into balloon-damaged carotid arteries of adult rats to investigate effects on elastogenesis in neointima. Overexpression of mutant biglycan, without GAG chains, promoted elastogenesis in vitro and in vivo. Furthermore the increased elastogenesis was accompanied by decreased collagen synthesis and collagen fiber deposition.

A. Materials and Methods

Standard molecular biology protocols were used, e.g., as described in Ausubel et al. (2004 *Current Protocols in Molecular Biology*, John Wiley & Sons, Inc., Boston, Mass.); Sambrook et al. (2001 *Molecular Cloning*, Third Ed., Cold Spring Harbor Laboratory, Plainview, N.Y.); Maniatis et al. (1982 Molecular Cloning, Cold Spring Harbor Laboratory, Plainview, N.Y.); Glover (Ed.) (1985 *DNA Cloning Vol. I and II*, IRL Press, Oxford, UK); Hames and Higgins (Eds.), (1985 *Nucleic Acid Hybridization*, IRL Press, Oxford, UK); including with modifications as described herein. All reagents were from SigmaAldrich (St. Louis, Mo.) unless otherwise noted.

Retroviral Vectors and Construction of Mutant Biglycan.

The cDNA of human biglycan (courtesy of Dr Marian Young, National Institute of Dental research, National Institutes of Health, Bethesda, Md.) (Fisher et al., *Acta Orthop Scand. Suppl.*, 1995, 266:61-65) was inserted into the EcoR1 site of the replication defective retroviral vector LXSN (courtesy of Dr A D Miller, Fred Hutchinson Cancer Research Center, Seattle, Wash.) (Miller and Rosman, 1989 *Biotechniques* 7: 980-982; 984-980; 989-990) to create the biglycan-expressing vector (FIG. 1).

To assess the importance of the biglycan GAG side chains to ASMC phenotype and metabolism, site-directed mutagenesis was used to create mutant biglycan-encoding cDNA in which the serines at the two GAG attachment sites of the biglycan core protein were replaced by alanine residues. Two complementary oligonucleotides were used for the mutagenesis reaction:

```
forward
                                           [SEQ ID NO: 1]
5'-GAAC GAT GAG GAA GCT GCG GGC GCT GAC ACC GCA

GGC GTC CTG GACC-3' reverse
                                           [SEQ ID NO: 2]
5'-GGTC CAG GAC GCC TGC GGT GTC AGC GCC CGC AGC

TTC CTC ATC GTTC-3'
```

These primers encoded for T to G substitutions at the bases underlined on the forward primer, thus encoding for alanines rather than serines at the $5^{th}$ and $10^{th}$ amino acid residues of the biglycan core protein (SEQ ID NO:4) to give rise to a double mutant (SEQ ID NO:3) lacking these two serine residues as GAG attachment sites. The two mutagenic primers were used in a PCR using pBluescript plasmid containing the native human biglycan cDNA as a template. The products of the PCR were treated with the methylation-sensitive reaction enzyme Dpn1 to digest the parental DNA plasmid template.

Enriched mutant plasmids were transfected into *E. coli*, and the resultant colonies screened for mutant cDNA clones. The full-length mutant biglycan cDNA was sequenced to confirm the presence of the intended mutant biglycan sequence and the *E. coli* cDNA fragment encoding the mutant biglycan was inserted into the LXSN vector.

LXSN vectors containing human biglycan cDNA, or mutant human biglycan, were transfected into PA317 packaging cells (Corsaro and Pearson, 1981 *Somatic Cell Genet.* 7:603-616) and the resultant viruses LBSN (encoding wild-type human biglycan) and LMBSN (encoding the double mutant human biglycan) as well as the empty vector (LXSN) were used to transduce Fisher 344 rats ASMC as described previously (Clowes et al., 1994 *J. Clin. Invest.* 93:644-651).

Cell culture. ASMC were obtained and cultured as previously described (Clowes et al., 1994 *J. Clin. Invest.* 93:644-651). Transduced cells were maintained in DMEM high glucose medium supplemented with 10% fetal bovine serum, sodium pyruvate, non-essential amino acids, glutamine and penicillin-streptomycin (Invitrogen Corp., Carlsbad, Calif.). Cells were used between four and eight passages after the initial transduction.

Northern Blot Analysis.

For Northern analysis $7.5 \times 10^5$ cells were plated in 60 mm dishes and cultured for 14 days. Total RNA was extracted from cells by RNAeasy Mini Kits (Qiagen, Valencia, Calif.). Twelve micrograms per sample of total RNA was run on a 0.8% agarose gel containing formaldehyde, then subjected to limited hydrolysis and transferred to Zetaprobe (Bio-Rad, Hercules, Calif.) and cross linked by UV light. Membranes were prehybridized for two hours at 42° C. in 50% formamide (Life Technologies Inc., Gaithersburg, Md.), 6×SSPE, 5×Denhardt's solution, 0.5% SDS, 5% dextran sulphate, and 100 μg/ml salmon sperm DNA (Sigma). Probes were labeled by random priming using 5'-[α-$^{32}$P]dCTP (Amersham-Pharmacia Biotech Inc., Piscataway, N.J.) as described previously (Lemire et al., 1999 *Arterioscler. Thromb. Vasc. Biol.* 19:1630-1639). Hybridization was carried out at 42° C. for 16 hours, followed by three washes with 2×SSPE/0.1% SDS at 42° C. and 2 washes with 0.3%×SSPE/0.1% SDS at 65° C.

Full-length human biglycan cDNA (Fisher, L W., *Acta Orthop Scand Suppl* 1995, 266: 61-65) was used to detect all endogenous rat biglycan, human biglycan and mutant human biglycan mRNA. Tropelastin mRNA was detected with a specific probe (Boyd et al., *Conn Tiss Res* 1988:18:65-78) generously provided by Dr. C. D. Boyd, University of Hawaii, Manoa, Honolulu, Hi. Collagen α(I) was detected with human proα1(I) (Chu, M L et al., *Nucleic Acid Res* 1982, 10:5925-34)

Western Analysis.

48 hour conditioned media from 14-day cultures, seeded at $7.5 \times 10^5$ in 60 mm dishes, were collected for Western analysis of biglycan core protein. To confirm the absence of GAG chains on biglycan secreted by LMBSN-transduced cells, samples of conditioned medium were passed over 0.5 ml DEAE-Sephacel columns in 8 M urea, 0.5% Triton X-100, 0.01 Tris-HCL, pH 7.5, and 0.25 1 M NaCl (urea buffer), washed with 10 volumes of urea buffer, and eluted with 3 M NaCl in urea buffer to collect any biglycan with GAG chains attached.

Western blot analysis was performed as described previously (Schoenherr et al., *Arch. Biochem. Biophys.* 1997, 339: 353-361). Briefly, following the addition of 30 mg carrier chondroitin sulphate, eluted material was precipitated at 20° C. by addition of 3.5 volumes of 95% ethanol containing 1.3% potassium acetate. The pellet was dissolved in distilled water and the ethanol precipitation repeated without the addition of carrier. Following centrifugation the supernatant was discarded and the pellet air-dried. Samples were resuspended in 8 mol urea. Chondroitinase digestion with ABC lyase (0.02 U) was carried out in Tris buffer at pH 8 for 3 hours at 37° C. Samples were boiled for 5 minutes in SDS-containing gel electrophoresis sample buffer with β-mercaptoethanol.

All samples were electrophoresed on 10% SDS-polyacrylamide gels and transferred to nitrocellulose membranes (BA83, Whatman Scheicher and Schuell Inc., Florham Park, N.J.) and exposed to primary antibody against human biglycan (LF51, a kind gift from Dr. Larry Fischer, National Institute of Dental Research, Bethesda, Md.) (Fisher, L W et al., 1995:266:61-65). Following incubation with an alkaline phosphatase-conjugated secondary antibody, biglycan core protein was detected by enzyme-linked chemiluminescence (Tropix Inc., Bedford, Mass.).

Immunocytochemistry.

Polyclonal rabbit antisera to the human α1(I) c-telopeptide of collagen I (LF67) (Fisher, L W et al., 1995 *Acta Orthop Scand Suppl* 266: 61-15) was generously provided by Dr Larry Fisher (NIDR, Bethesda, Md.). Polyclonal rabbit antisera to recombinant bovine tropoelastin, which also recognizes rat elastin, was generously provided by Dr Robert Mecham, Washington University, St Louis, Mo.). Immunocytochemistry for cultured cells was performed as described previously (Lara, S et al., in Methods in Molecular Biology. Proteoglycan Protocols, Vol 171:271-290, 2001).

Balloon Injury and Cell Seeding.

Carotid artery balloon injury and cell seeding were performed in Fisher 344 rats as described previously (Fischer et al., 2000 *Circ. Res.* 86:676-683). All surgical procedures were performed according to the Principles of Laboratory Animal Care and the Guide for the Care and Use of Laboratory Animals (National Institutes of Health, publication No. 86-23, revised 1985). Ten animals were used for each group (LXSN, LBSN, LMBSN) at each time point (2 and 4 weeks). At week two, 6 animals from each group were used for light microscopy (LM) analysis, two animals for electron microscopy (EM), and two for RT-PCR. At week four, 8 animals were used for LM and two animals for EM.

Detection of Seeded Cells.

RNA was extracted from frozen and homogenized pooled carotid arteries by the method of Chomczynski and Sacchi (1987 *Anal. Biochem.* 162:156-159). One microgram of total RNA was reverse transcribed and amplified using random hexamer primers and the Superscript Preamplification System Kit (Gibco/BRL). To detect LXSN cDNA, a 510 base DNA fragment of LXSN was amplified (LXSN forward primer 1573, 5'-CCT TGA ACC TCC TCG TTC GAC-3' 1593 SEQ ID NO:5; LXSN reverse primer 2079, 5'-TCT TGT TCA ATC ATG CGA AAC G-3' 2061 SEQ ID NO:6). To detect LBSN and LMBSN cDNA, a 986-base DNA fragment of LBSN and LMBSN cDNA were amplified (LXSN forward primer 1573, 5'-CCT TGA ACC TCC TCG TTC GAC-3' 1593, SEQ ID NO:5; human biglycan reverse primer, 5'-GTA CAG CTT GGA GTA GCG AAG CA-3', 866 SEQ ID NO:7). Thirty-five PCR cycles were performed.

Histochemistry, Immunohistochemistry and Electron Microscopy.

Vessels for immunohistochemistry were perfusion fixed with 10% neutral-buffered formalin at 120 mm Hg pressure and sections from the paraffin-embedded carotids stained with H&E, Massons Trichrome, and orcein to show general morphology, collagen and elastin respectively. Human biglycan and mutant human biglycan were detected with polyclonal antisera against recombinant human biglycan, LF121 (Fisher et al, 1995 *Acta Orthop Scand Suppl* 266: 61-65) (kind gift from Dr Larry Fischer). Vessel segments for electron microscopy were fixed in 3% glutaraldehyde in 0.1 mol/L cacodylate buffer, secondarily fixed in 1% OsO$_4$, processed, and sectioned at right angles to the vessel axis. Thin sections were mounted on formvar-coated grids, stained with uranyl acetate and lead citrate and viewed on a JOEL 1200 EXII microscope.

Data were analyzed by Student's T test and a value of $p<0.05$ taken as significant.

B. Results

Expression and Secretion of Human Biglycan and Mutant Human Biglycan.

Figure 2:
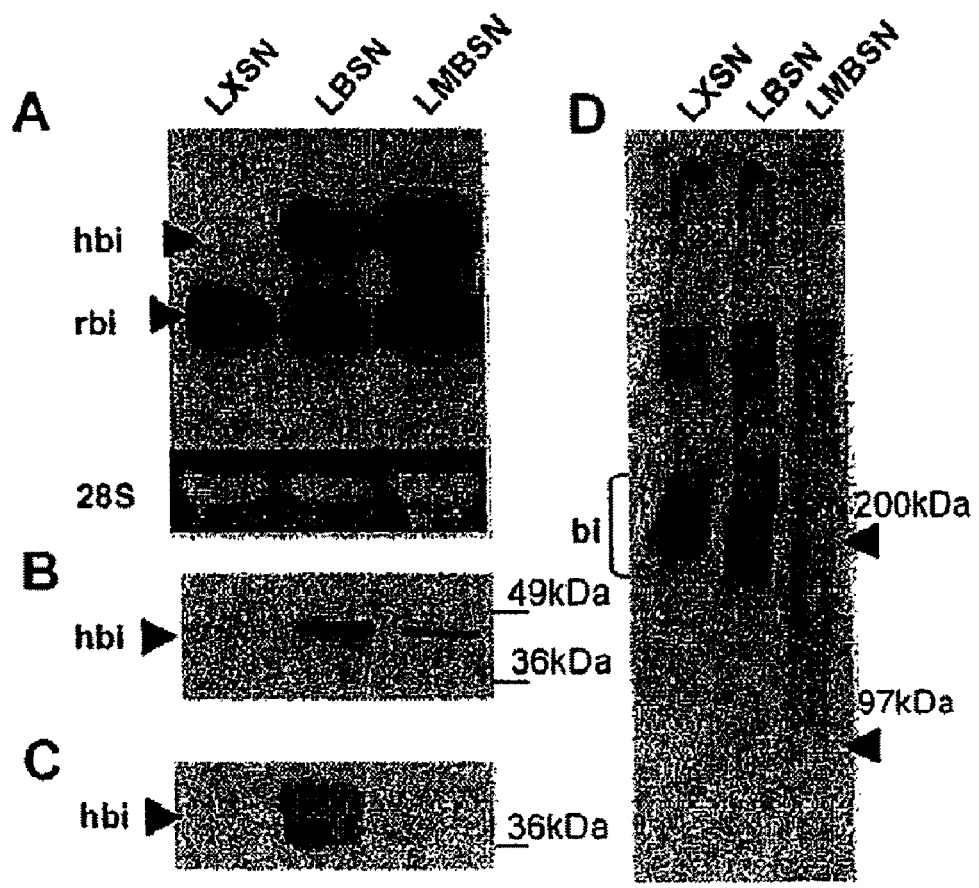

Messenger RNA for endogenous rat biglycan and mRNAs for retrovirally introduced human biglycan and mutant biglycan were expressed and distinguishable by Northern blot in early (4-day) and extended (14-day, FIG. 2A) cultures of Fisher rat smooth muscle cells. Human biglycan core protein, isolated from 48 hour conditioned media from 14-day LBSN cultures, and digested with chondroitin ABC lyase, was detected on Western blot using antibody LF 51 that recognizes the core protein of human but not rat biglycan (FIG. 2B). Passage of conditioned media samples over a DEAE column prior to chondroitinase digestion showed that mutant human biglycan was not retained on the column, confirming the absence of GAG chains (FIG. 2C). PAGE analysis of [$^{35}$S] sulphate-labeled secreted proteoglycans further confirmed the absence of GAG chains on mutant biglycan produced by the LMBSN-transduced cells as well as confirming the increase in total wildtype biglycan in the LBSN-transduced biglycan overexpressing cells (FIG. 2D).

Tropoelastin Expression, Insoluble Elastin Production and Collagen α(I) Expression.

Northern blot of mRNA isolated from 14-day cultures and hybridized with a human tropoelastin probe that also recognized rat tropoelastin showed a 3.5 fold increase in message in the LMBSN-transduced cells (FIGS. 3A,B). The tropoelastin message level in the LBSN-transduced cells was decreased by a small amount. Similar results were obtained for 4-day cultures (data not shown). Quantitative analysis of immunoprecipitable [$^3$H]-valine-labeled insoluble elastin showed a significant increase ($p<0.05$) in insoluble elastin in the LMBSN-transduced cultures and a corresponding and significant decrease in the LBSN (FIG. 3C). Collagen α(I) mRNA by the human mutant biglycan producing cells was markedly reduced compared with both LXSN-transduced and LBSN-transduced cells (FIG. 4A).

Immunostaining for Tropoelastin and for Type I Collagen.

Differences in immunostaining of cultured cells (FIG. 5) matched the differences in the mRNA expression patterns (FIGS. 3A, 3B) and the insoluble elastin levels (FIG. 3C). Elastic fibers were present in both LXSN-transduced and LMBSN-transduced cultures, but the latter displayed both more and better defined fibers (FIG. 5). In contrast, elastin staining was markedly reduced in the LBSN-transduced cultures. Type I collagen immunostaining was markedly reduced in the LMBSN cultures compared with both the LXSN and LBSN cultures (FIG. 5).

Expression and Production of Human Biglycan in Balloon-Injured Seeded Vessels.

RT-PCR of carotid vessels 4 weeks after injury and cell seeding demonstrated the presence of appropriately sized transcripts for LXSN, LBSN and LMBSN (FIG. 6). Immunostaining of 2 and 4 week-old seeded carotids with LF121, a polyclonal antibody that recognized human biglycan, demonstrated strong staining at both time points in LBSN and LMBSN neointimae, and negative staining in the medial and adventitial layers as well as in the LXSN neointimae. Staining was generally evenly intense through the full width of neointimae, but with slightly stronger staining in the deep intimae.

Elastin Deposition.

Orcein staining of 2 and 4 week-old seeded carotids demonstrated elastin deposits in the neointimae of all vessels (FIG. 7). The LXSN and LBSN seeded vessels contained numerous punctate and generally small deposits of elastin scattered throughout the extracellular matrix of the neointimae. In contrast, LMBSN neointimae contained more elastin and in larger deposits, often aggregated into lamellae-like structures arranged parallel to the internal elastic lamina. The cell density in the LMBSN neointimae was also significantly increased compared with the LXSN and LBSN neointimae ($p<0.05$).

The increased deposition of elastin in the LMBSN neointimae, compared with LBSN, and the enhanced aggregation of elastin into nascent fibers and lamellae, were clearly demonstrated by electron microscopy (FIG. 8). Furthermore, in addition to the increased amount and aggregation of mature elastin, LMBSN neointimae contained large amounts of immature and microfibrillar-rich elastin (FIG. 8B), indicative of continuing elastin production and assembly. Notably, the extracellular matrix of the LMBSN neointimae contained a relatively low content of collagen fibers, in contrast to LBSN neointimae, which contained dense bundles of collagen fibrils (FIG. 8A).

Example 2

Promotion of Elastogenesis by Engineered Versican V3-Derived Polypeptides

This example describes unexpected elastogenic properties of engineered versican V3-derived polypeptides that were derived from a rat V3 polymorph (SEQ ID NO:27) differing in sequence by a single amino acid substitution from a reported rat versican isoform V3 polypeptide (SEQ ID NO:26). Materials and methods were as described above in Example 1 and as described in Huang et al., 2006 Circ. Res. 98:370-377 using the LXSN viral vector system, except engineered versican V3-derived polypeptides were encoded by cDNA inserts comprising the polynucleotide sequences of SEQ ID NOS:8, 10, 12, 14, and 18, which directed, respectively, the expression of polypeptides having the amino acid sequences set forth in SEQ ID NOS:9, 11, 13, 15 and 19.

Vectors comprising polynucleotide sequences of SEQ ID NOS:16, 20, 22 and 24 are also contemplated, and may be constructed as described above, to direct the expression, respectively, of polypeptides having the amino acid sequences set forth in SEQ ID NOS:17, 21, 23 and 25.

FIG. 9 shows a schematic diagram of versican V3 isoform exon utilization by the engineered versican V3-derived polypeptides comprising the amino acid sequences set forth in SEQ ID NOS:9 (exon 3 deleted), 11 (exons 4/5 deleted), 12 (exon 6 deleted), 15 (exons 9/10 deleted), 17 (exons 11/12/13 deleted) and 19 (exon 14 deleted). The effects of the engineered V3-derived polypeptides on smooth muscle cell tropoelastin mRNA expression were assessed by northern blot analysis as described above in Example 1 and in Huang et al. (2006) and the results are shown in FIG. 10.

Example 3

Promotion of Elastogenesis by Metastatin

This example describes unexpected elastogenic properties of metastatin when administered to rat vascular smooth muscle cells and analysis of tropoelastin mRNA expression and elastin fiber formation as described in the preceding Examples and in Huang et al. (2006 Circ. Res. 98:370-377).

Metastatin was prepared and characterized as described by Liu et al. (2001 Canc. Res. 61:1022) and used to treat smooth muscle cell cultures at 20 µg/ml. To verify the hyauronan-binding activity of metastatin, preabsorption with hyaluronic acid (HA, 100 µg/ml) was performed for some experimental groups. Immunofluorescent staining of cell cultures to detect patterns of elastin distribution, and northern blot analysis for tropoelastin mRNA, were conducted as described above. Elastin immunostaining and tropoelastin mRNA levels were increased in cultures treated with metastatin, and decreased in cultures that were treated with the HA-preabsorbed metastatin. Metastatin treatment also decreased versican immunostaining in the smooth muscle cell cultures.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for promoting tropoelastin mRNA expression in a cell, comprising:
    contacting a cell that is capable of elastogenesis with an effective amount of a composition which comprises a polypeptide that is selected from:
    (a) a polypeptide which comprises the amino acid sequence as set forth in one of SEQ ID NOS:11, 13, 19, 21 and 23, and
    (b) a polypeptide which comprises at least 95% amino acid sequence identity to the amino acid sequence set forth in one of SEQ ID NOS:11, 13, 19, 21 and 23,
    and thereby promoting tropoelastin mRNA expression in the cell.

2. The method of claim 1 wherein the step of contacting is performed in vitro.

3. The method of claim 1 wherein the step of contacting is performed in vitro and wherein the cell is present in an engineered biological tissue.

4. The method of claim 3 wherein the biological tissue is a connective tissue.

5. The method of claim 4 wherein the connective tissue is selected from cartilage, ligament and tendon.

6. The method of claim 3 wherein the engineered biological tissue is selected from the group consisting of a blood vessel, heart tissue, skin, lung tissue, urogenital tissue and gastrointestinal tissue.

7. The method of claim 1 wherein the step of contacting is performed in a human or in a non-human mammal.

8. The method of claim 7 wherein the non-human mammal is selected from the group consisting of a non-human primate, a lagomorph, a rodent, an ungulate, a feliform, and a caniform.

9. The method of claim 8 wherein the lagomorph is selected from a rabbit, a hare and a pika, and wherein the rodent is selected from a mouse, a rat, a gerbil, a guinea pig and a hamster.

10. The method of claim 1 wherein the cell is a connective tissue cell.

11. The method of claim 1 wherein the cell is selected from the group consisting of a smooth muscle cell, a fibroblast, a myofibroblast, a chondrocyte, a pericyte, a glial cell, a glioma cell, a macrophage and an epithelial cell.

12. The method of claim 11 wherein the smooth muscle cell is selected from the group consisting of a vascular smooth muscle cell, a gastrointestinal tract smooth muscle cell, a respiratory tract smooth muscle cell and a urogenital tract smooth muscle cell.

13. The method of claim 11 wherein the smooth muscle cell is a vascular smooth muscle cell that is selected from an arterial smooth muscle cell and a venous smooth muscle cell.

14. A method for treating a subject having or suspected of being at risk for having a condition associated with inadequate elastin fiber formation, comprising:
    administering, to a subject having or suspected of being at risk for having a condition associated with inadequate elastin fiber formation, an effective amount of a composition that promotes tropoelastin mRNA expression, which composition comprises a polypeptide that is selected from:
    (a) a polypeptide which comprises the amino acid sequence as set forth in one of SEQ ID NOS:11, 13, 19, 21 and 23, and
    (b) a polypeptide which comprises at least 95% amino acid sequence identity to the amino acid sequence as set forth in one of SEQ ID NOS:11, 13, 19.21 and 23,
    and thereby treating the subject having or suspected of being at risk for having the condition associated with inadequate elastin fiber formation.

15. The method of claim 14 wherein the condition associated with inadequate elastin fiber formation is selected from the group consisting of emphysema, chronic obstructive pulmonary disease, idiopathic pulmonary fibrosis, lymphangioleiomyomatosis, atherosclerosis, aneurysm, aortic dissection and restenosis.

16. The method of claim 14 wherein the condition associated with inadequate elastin fiber formation is selected from the group consisting of cutis laxa, pseudoxanthoma elasticum and a pelvic floor disorder.

17. The method of claim 14 wherein the condition associated with inadequate elastin fiber formation is an aging-associated condition.

18. The method of claim 14 wherein the condition associated with inadequate elastin fiber formation results in wrinkled skin.

19. The method of claim 14 wherein the condition associated with inadequate elastin fiber formation comprises a valvular disease.

20. The method of claim 14 wherein the condition associated with inadequate elastin fiber formation is selected from the group consisting of Costello Syndrome, Hurler Disease, Williams-Beuren Syndrome, Morquio B disease, infantile GM1-gangliosidosis, supravalvular aortic stenosis, pregnancy, Marfan's syndrome, Ehlers-Danlos syndrome, aortic coarctation, and bicuspid aortic valve disease.

* * * * *

UNITED STATES PATENT AND TRADEMARK OFFICE
CERTIFICATE OF CORRECTION

PATENT NO. : 8,367,619 B2  Page 1 of 1
APPLICATION NO. : 12/526625
DATED : February 5, 2013
INVENTOR(S) : Thomas N. Wight et al.

It is certified that error appears in the above-identified patent and that said Letters Patent is hereby corrected as shown below:

In the Claims
Column 106, Line 31:
"set forth in one of SEQ ID NOS: 11, 13, 19.21 and 23," should read, --set forth in one of SEQ ID NOS: 1, 13, 19, 21 and 23,--.

Signed and Sealed this
Twenty-fourth Day of December, 2013

Margaret A. Focarino
*Commissioner for Patents of the United States Patent and Trademark Office*

SEQUENCE LISTING

<160> NUMBER OF SEQ ID NOS: 41

<210> SEQ ID NO 1
<211> LENGTH: 47
<212> TYPE: DNA
<213> ORGANISM: Artificial Sequence
<220> FEATURE:
<223> OTHER INFORMATION: Oligonucleotide

<400> SEQUENCE: 1
gaacgatgag gaagctgcgg gcgctgacac cgcaggcgtc ctggacc            47

<210> SEQ ID NO 2
<211> LENGTH: 47
<212> TYPE: DNA
<213> ORGANISM: Artificial Sequence
<220> FEATURE:
<223> OTHER INFORMATION: Oligonucleotide

<400> SEQUENCE: 2
ggtccaggac gcctgcggtg tcagcgcccg cagcttcctc atcgttc            47

<210> SEQ ID NO 3
<211> LENGTH: 368
<212> TYPE: PRT
<213> ORGANISM: Artificial Sequence
<220> FEATURE:
<223> OTHER INFORMATION: Mutant human biglycan polypeptide

<400> SEQUENCE: 3

Met Trp Pro Leu Trp Arg Leu Val Ser Leu Leu Ala Leu Ser Gln Ala
 1               5                   10                  15

Leu Pro Phe Glu Gln Arg Gly Phe Trp Asp Phe Thr Leu Asp Asp Gly
                20                  25                  30

Pro Phe Met Met Asn Asp Glu Glu Ala Gly Ala Asp Thr Ala Gly
            35                  40                  45

Val Leu Asp Pro Asp Ser Val Thr Pro Thr Tyr Ser Ala Met Cys Pro
 50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
210                 215                 220

```
Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
            245                 250                 255

Arg Leu Gly Leu Gly His Asn Gln Ile Arg Met Ile Glu Asn Gly Ser
        260                 265                 270

Leu Ser Phe Leu Pro Thr Leu Arg Glu Leu His Leu Asp Asn Asn Lys
    275                 280                 285

Leu Ala Arg Val Pro Ser Gly Leu Pro Asp Leu Lys Leu Leu Gln Val
290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
                340                 345                 350

Arg Cys Val Thr Asp Arg Leu Ala Ile Gln Phe Gly Asn Tyr Lys Lys
                355                 360                 365
```

<210> SEQ ID NO 4
<211> LENGTH: 368
<212> TYPE: PRT
<213> ORGANISM: Homo sapiens

<400> SEQUENCE: 4

```
Met Trp Pro Leu Trp Arg Leu Val Ser Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
210                 215                 220

Lys Asp Leu Pro Glu Thr Leu Asn Glu Leu His Leu Asp His Asn Lys
225                 230                 235                 240
```

-continued

```
Ile Gln Ala Ile Glu Leu Glu Asp Leu Leu Arg Tyr Ser Lys Leu Tyr
                245                 250                 255
Arg Leu Gly Leu Gly His Asn Gln Ile Arg Met Ile Glu Asn Gly Ser
            260                 265                 270
Leu Ser Phe Leu Pro Thr Leu Arg Glu Leu His Leu Asp Asn Asn Lys
        275                 280                 285
Leu Ala Arg Val Pro Ser Gly Leu Pro Asp Leu Lys Leu Leu Gln Val
    290                 295                 300
Val Tyr Leu His Ser Asn Asn Ile Thr Lys Val Gly Val Asn Asp Phe
305                 310                 315                 320
Cys Pro Met Gly Phe Gly Val Lys Arg Ala Tyr Asn Gly Ile Ser
                325                 330                 335
Leu Phe Asn Asn Pro Val Pro Tyr Trp Glu Val Gln Pro Ala Thr Phe
            340                 345                 350
Arg Cys Val Thr Asp Arg Leu Ala Ile Gln Phe Gly Asn Tyr Lys Lys
        355                 360                 365

<210> SEQ ID NO 5
<211> LENGTH: 21
<212> TYPE: DNA
<213> ORGANISM: Artificial Sequence
<220> FEATURE:
<223> OTHER INFORMATION: Olignucleotide

<400> SEQUENCE: 5
ccttgaacct cctcgttcga c                                           21

<210> SEQ ID NO 6
<211> LENGTH: 22
<212> TYPE: DNA
<213> ORGANISM: Artificial Sequence
<220> FEATURE:
<223> OTHER INFORMATION: Olignucleotide

<400> SEQUENCE: 6
tcttgttcaa tcatgcgaaa cg                                          22

<210> SEQ ID NO 7
<211> LENGTH: 23
<212> TYPE: DNA
<213> ORGANISM: Artificial Sequence
<220> FEATURE:
<223> OTHER INFORMATION: Olignucleotide

<400> SEQUENCE: 7
gtacagcttg gagtagcgaa gca                                         23

<210> SEQ ID NO 8
<211> LENGTH: 1855
<212> TYPE: DNA
<213> ORGANISM: Artificial Sequence
<220> FEATURE:
<223> OTHER INFORMATION: DNA encoding engineered versican V-3-derived
      polypeptide having exon 3 deleted

<400> SEQUENCE: 8
taagccgcct ttcaaggaca agatgttgat aaatatgaac ggcatcctat ggatgtgctc     60
aaccttactg ttaacgcatg cactgcataa agccaaatg gaagaaaacc cacctgttaa     120
aggctctctg tctggaaaag tgatcggcat tgaagacact cagaacacga tgtcgctggc    180
cgtggacggt gtcgtgtttc actacagggc agcgaccagc agatacactc tgaacttcga    240
gtctgctcaa caggcttgtt tggacatcgg ggcggtcata gcaaccccag agcagctgtt    300
```

```
cgctgcctat gaggatggat ttgagcagtg tgatgcagga tggctgtctg accaaactgt    360
cagatatccc atacgggctc cccgagaggg ctgttatgga gacatgatgg ggaaggaagg    420
ggtccggacc tatggattcc gctctcccca ggaaacctat gatgtgtatt gctatgtgga    480
tcatctggac ggcgatgtgt ccacatcac tgctcccagt aaattcacct tcgaggaggc    540
cgaagcagag tgtgcaaacc gggatgccag gctggcgact gttggggaac ttcacgcagc    600
ttggaggaac ggctttgacc agtgcgatta cggctggctg tcggatgcca gcgtgcggca    660
ccctgtgact gtggccaggg cccagtgtgg aggtggtcta cttggggtga acccctgta    720
tcgttttgag aaccagacat gcttccctct ccctgatagc agatttgatg cctactgctt    780
taaacgacct gatctctgca aaacaaaccc atgcctcaat ggaggcacct gctatcctac    840
tgagacttcc tatgtgtgca cctgtgcacc tggctacagt ggagaccagt gtgaactgga    900
ttttgatgaa tgtcactcta acccttgtcg gaatggagcc acctgtgtgg acggtctgaa    960
tacatttaga tgcctctgcc ttccgagtta tgtcggtgca ctctgcgaac aagacactga   1020
gacatgcgac tatggctggc acaaattcca agggcaatgc acaagtactt tgctcatcg   1080
ccgtacatgg gatgctgctg aaagggagtg tcgcctgcag ggtgcccacc tcacaagcat   1140
cctttctcat gaggaacaaa tgtttgtgaa tcgtgtgggc catgattacc agtggattgg   1200
cctcaatgac aagatgtttg aacatgactt ccgctggact gacggcagcg cactgcaata   1260
tgagaactgg agacccaacc agccagacag cttctttttct gctggagaag actgcgttgt   1320
gatcatttgg catgagaatg gccagtggaa tgacgtcccc tgcaactacc acctcaccta   1380
cacctgcaag aagggaacag ttgcttgcgg ccaaccccct gttgtagaaa atgccaagac   1440
ctttggaaag atgaaaccac gttatgaaat caactccttg attagatacc actgcaaaga   1500
tggtttcatt cagcgtcacc ttccaactat ccggtgccta ggaaatggga gatgggcaat   1560
gcctaaaata acctgcatga acccatctgc ataccaaagg acttattcta agaaatactt   1620
aaaaaattcc tcatcagtca aggacaattc tataaatacg tcaaaacatg agcatcgctg   1680
gagccggagg tggcaggaaa cgaggcgctg atcctaaaat ggcgaacata agcttcattc   1740
atcatttcag ccaaagccct gcctttccgt gcctttccta tcacctcaag gagaattagc   1800
agttggtttg gattttggga ctgccgtctg gtcatttggg gtggctgtat tccta         1855
```

<210> SEQ ID NO 9
<211> LENGTH: 562
<212> TYPE: PRT
<213> ORGANISM: Artificial Sequence
<220> FEATURE:
<223> OTHER INFORMATION: Engineered versican V-3-dervied polypeptide
      having exon 3 deleted

<400> SEQUENCE: 9

Met Leu Ile Asn Met Asn Gly Ile Leu Trp Met Cys Ser Thr Leu Leu
 1               5                  10                  15

Leu Thr His Ala Leu His Lys Ala Lys Met Glu Glu Asn Pro Pro Val
             20                  25                  30

Lys Gly Ser Leu Ser Gly Lys Val Ile Gly Ile Glu Asp Thr Gln Asn
         35                  40                  45

Thr Met Ser Leu Ala Val Asp Gly Val Val Phe His Tyr Arg Ala Ala
     50                  55                  60

Thr Ser Arg Tyr Thr Leu Asn Phe Glu Ser Ala Gln Gln Ala Cys Leu
65                  70                  75                  80

Asp Ile Gly Ala Val Ile Ala Thr Pro Glu Gln Leu Phe Ala Ala Tyr

-continued

```
                85                  90                  95
Glu Asp Gly Phe Glu Gln Cys Asp Ala Gly Trp Leu Ser Asp Gln Thr
                100                 105                 110

Val Arg Tyr Pro Ile Arg Ala Pro Arg Glu Gly Cys Tyr Gly Asp Met
                115                 120                 125

Met Gly Lys Glu Gly Val Arg Thr Tyr Gly Phe Arg Ser Pro Gln Glu
                130                 135                 140

Thr Tyr Asp Val Tyr Cys Tyr Val Asp His Leu Asp Gly Asp Val Phe
145                 150                 155                 160

His Ile Thr Ala Pro Ser Lys Phe Thr Phe Glu Glu Ala Glu Ala Glu
                165                 170                 175

Cys Ala Asn Arg Asp Ala Arg Leu Ala Thr Val Gly Glu Leu His Ala
                180                 185                 190

Ala Trp Arg Asn Gly Phe Asp Gln Cys Asp Tyr Gly Trp Leu Ser Asp
                195                 200                 205

Ala Ser Val Arg His Pro Val Thr Val Ala Arg Ala Gln Cys Gly Gly
                210                 215                 220

Gly Leu Leu Gly Val Arg Thr Leu Tyr Arg Phe Glu Asn Gln Thr Cys
225                 230                 235                 240

Phe Pro Leu Pro Asp Ser Arg Phe Asp Ala Tyr Cys Phe Lys Arg Pro
                245                 250                 255

Asp Leu Cys Lys Thr Asn Pro Cys Leu Asn Gly Gly Thr Cys Tyr Pro
                260                 265                 270

Thr Glu Thr Ser Tyr Val Cys Thr Cys Ala Pro Gly Tyr Ser Gly Asp
                275                 280                 285

Gln Cys Glu Leu Asp Phe Asp Glu Cys His Ser Asn Pro Cys Arg Asn
                290                 295                 300

Gly Ala Thr Cys Val Asp Gly Leu Asn Thr Phe Arg Cys Leu Cys Leu
305                 310                 315                 320

Pro Ser Tyr Val Gly Ala Leu Cys Glu Gln Asp Thr Glu Thr Cys Asp
                325                 330                 335

Tyr Gly Trp His Lys Phe Gln Gly Gln Cys Tyr Lys Tyr Phe Ala His
                340                 345                 350

Arg Arg Thr Trp Asp Ala Ala Glu Arg Glu Cys Arg Leu Gln Gly Ala
                355                 360                 365

His Leu Thr Ser Ile Leu Ser His Glu Glu Gln Met Phe Val Asn Arg
                370                 375                 380

Val Gly His Asp Tyr Gln Trp Ile Gly Leu Asn Asp Lys Met Phe Glu
385                 390                 395                 400

His Asp Phe Arg Trp Thr Asp Gly Ser Ala Leu Gln Tyr Glu Asn Trp
                405                 410                 415

Arg Pro Asn Gln Pro Asp Ser Phe Phe Ser Ala Gly Glu Asp Cys Val
                420                 425                 430

Val Ile Ile Trp His Glu Asn Gly Gln Trp Asn Asp Val Pro Cys Asn
                435                 440                 445

Tyr His Leu Thr Tyr Thr Cys Lys Lys Gly Thr Val Ala Cys Gly Gln
                450                 455                 460

Pro Pro Val Val Glu Asn Ala Lys Thr Phe Gly Lys Met Lys Pro Arg
465                 470                 475                 480

Tyr Glu Ile Asn Ser Leu Ile Arg Tyr His Cys Lys Asp Gly Phe Ile
                485                 490                 495

Gln Arg His Leu Pro Thr Ile Arg Cys Leu Gly Asn Gly Arg Trp Ala
                500                 505                 510
```

```
Met Pro Lys Ile Thr Cys Met Asn Pro Ser Ala Tyr Gln Arg Thr Tyr
    515                 520                 525

Ser Lys Lys Tyr Leu Lys Asn Ser Ser Val Lys Asp Asn Ser Ile
    530                 535                 540

Asn Thr Ser Lys His Glu His Arg Trp Ser Arg Arg Trp Gln Glu Thr
545                 550                 555                 560

Arg Arg

<210> SEQ ID NO 10
<211> LENGTH: 1858
<212> TYPE: DNA
<213> ORGANISM: Artificial Sequence
<220> FEATURE:
<223> OTHER INFORMATION: DNA encoding engineered versican V-3-derived
      polypeptide having exons 4 and 5 deleted

<400> SEQUENCE: 10
taagccgcct ttcaaggaca agatgttgat aaatatgaac ggcatcctat ggatgtgctc      60
aaccttactg ttaacgcatg cactgcataa agccaaaatg gaagaaaacc cacctgttaa     120
aggctctctg tctggaaaag tgatcctacc ttgtcatttt tcaaccttgc ccacttacc      180 acccgattac aacacgagtg aatttctcag aatcaaatgg tctaaaatag aagtggacaa     240
aaatggaaaa gacataaagg agactactgt cctggtggcc caagacggga acatcaagat     300
tggtcaggac tacaaggggc gggtatcagt gcctacgcat cccgatgacg taggcgatgc     360
ctctctcacc atggtcaaac tccgtgctag tgacgcaggt gtctaccgct gtgatgtcat     420
gtatggcatt gaagacactc agaacacgat gtcgctggcc gtggacgtgt attgctatgt     480
ggatcatctg gacggcgatg tgttccacat cactgctccc agtaaattca ccttcgagga     540
ggccgaagca gagtgtgcaa accgggatgc caggctggcg actgttgggg aacttcacgc     600
agcttggagg aacggcttg accagtgcga ttacggctgg ctgtcggatg ccagcgtgcg     660
gcaccctgtg actgtggcca gggcccagtg tggaggtggt ctacttgggg tgagaaccct     720
gtatcgtttt gagaaccaga catgcttccc tctccctgat agcagatttg atgcctactg     780 cttaacga cctgatctct gcaaaacaaa cccatgcctc aatggaggca cctgctatcc     840
tactgagact tcctatgtgt gcacctgtgc acctggctac agtggagacc agtgtgaact     900
ggattttgat gaatgtcact ctaacccttg tcggaatgga gccacctgtg tggacggtct     960
gaatacattt agatgcctct gccttccgag ttatgtcggt gcactctgcg aacaagacac    1020
tgagacatgc gactatggct ggcacaaatt ccaagggcaa tgctacaagt actttgctca    1080
tcgccgtaca tgggatgctg ctgaaagggaa gtgtcgcctg cagggtgccc acctcacaag    1140
catcctttct catgaggaac aaatgtttgt gaatcgtgtg ggccatgatt accagtggat    1200
tggcctcaat gacaagatgt tgaacatga cttccgctgg actgacggca gcgcactgca    1260
atatgagaac tggagaccca accagccaga cagcttcttt tctgctggag aagactgcgt    1320
tgtgatcatt tggcatgaga atggccagtg gaatgacgtc ccctgcaact accacctcac    1380
ctacacctgc aagaagggaa cagttgcttg cggccaaccc cctgttgtag aaaatgccaa    1440
gacctttgga aagatgaaac cacgttatga aatcaactcc ttgattagat accactgcaa    1500
agatggtttc attcagcgtc accttccaac tatccggtgc ctaggaaatg ggagatgggc    1560
aatgcctaaa ataacctgca tgaacccatc tgcataccaa aggacttatt ctaagaaata    1620
cttaaaaaat tcctcatcag tcaaggacaa ttctataaat acgtcaaaac atgagcatcg    1680
ctggagccgg aggtggcagg aaacgaggcg ctgatcctaa aatggcgaac ataagcttca    1740
```

```
ttcatcattt cagccaaagc cctgcctttc cgtgcctttc ctatcacctc aaggagaatt    1800
agcagttggt ttggattttg ggactgccgt ctggtcattt ggggtggctg tattccta      1858
```

<210> SEQ ID NO 11
<211> LENGTH: 563
<212> TYPE: PRT
<213> ORGANISM: Artificial Sequence
<220> FEATURE:
<223> OTHER INFORMATION: Engineered versican V-3-dervied polypeptide
      having exons 4 and 5 deleted

<400> SEQUENCE: 11

```
Met Leu Ile Asn Met Asn Gly Ile Leu Trp Met Cys Ser Thr Leu Leu
 1               5                  10                  15

Leu Thr His Ala Leu His Lys Ala Lys Met Glu Glu Asn Pro Pro Val
            20                  25                  30

Lys Gly Ser Leu Ser Gly Lys Val Ile Leu Pro Cys His Phe Ser Thr
        35                  40                  45

Leu Pro Thr Leu Pro Pro Asp Tyr Asn Thr Ser Glu Phe Leu Arg Ile
    50                  55                  60

Lys Trp Ser Lys Ile Glu Val Asp Lys Asn Gly Lys Asp Ile Lys Glu
65                  70                  75                  80

Thr Thr Val Leu Val Ala Gln Asp Gly Asn Ile Lys Ile Gly Gln Asp
                85                  90                  95

Tyr Lys Gly Arg Val Ser Val Pro Thr His Pro Asp Val Gly Asp
            100                 105                 110

Ala Ser Leu Thr Met Val Lys Leu Arg Ala Ser Asp Ala Gly Val Tyr
        115                 120                 125

Arg Cys Asp Val Met Tyr Gly Ile Glu Asp Thr Gln Asn Thr Met Ser
    130                 135                 140

Leu Ala Val Asp Val Tyr Cys Tyr Val Asp His Leu Asp Gly Asp Val
145                 150                 155                 160

Phe His Ile Thr Ala Pro Ser Lys Phe Thr Phe Glu Glu Ala Glu Ala
                165                 170                 175

Glu Cys Ala Asn Arg Asp Ala Arg Leu Ala Thr Val Gly Glu Leu His
            180                 185                 190

Ala Ala Trp Arg Asn Gly Phe Asp Gln Cys Asp Tyr Gly Trp Leu Ser
        195                 200                 205

Asp Ala Ser Val Arg His Pro Val Thr Val Ala Arg Ala Gln Cys Gly
    210                 215                 220

Gly Gly Leu Leu Gly Val Arg Thr Leu Tyr Arg Phe Glu Asn Gln Thr
225                 230                 235                 240

Cys Phe Pro Leu Pro Asp Ser Arg Phe Asp Ala Tyr Cys Phe Lys Arg
                245                 250                 255

Pro Asp Leu Cys Lys Thr Asn Pro Cys Leu Asn Gly Gly Thr Cys Tyr
            260                 265                 270

Pro Thr Glu Thr Ser Tyr Val Cys Thr Cys Ala Pro Gly Tyr Ser Gly
        275                 280                 285

Asp Gln Cys Glu Leu Asp Phe Asp Glu Cys His Ser Asn Pro Cys Arg
    290                 295                 300

Asn Gly Ala Thr Cys Val Asp Gly Leu Asn Thr Phe Arg Cys Leu Cys
305                 310                 315                 320

Leu Pro Ser Tyr Val Gly Ala Leu Cys Glu Gln Asp Thr Glu Thr Cys
                325                 330                 335

Asp Tyr Gly Trp His Lys Phe Gln Gly Gln Cys Tyr Lys Tyr Phe Ala
            340                 345                 350
```

His Arg Arg Thr Trp Asp Ala Ala Glu Arg Glu Cys Arg Leu Gln Gly
        355                 360                 365

Ala His Leu Thr Ser Ile Leu Ser His Glu Glu Gln Met Phe Val Asn
    370                 375                 380

Arg Val Gly His Asp Tyr Gln Trp Ile Gly Leu Asn Asp Lys Met Phe
385                 390                 395                 400

Glu His Asp Phe Arg Trp Thr Asp Gly Ser Ala Leu Gln Tyr Glu Asn
                405                 410                 415

Trp Arg Pro Asn Gln Pro Asp Ser Phe Phe Ser Ala Gly Glu Asp Cys
                420                 425                 430

Val Val Ile Ile Trp His Glu Asn Gly Gln Trp Asn Asp Val Pro Cys
            435                 440                 445

Asn Tyr His Leu Thr Tyr Thr Cys Lys Lys Gly Thr Val Ala Cys Gly
    450                 455                 460

Gln Pro Pro Val Val Glu Asn Ala Lys Thr Phe Gly Lys Met Lys Pro
465                 470                 475                 480

Arg Tyr Glu Ile Asn Ser Leu Ile Arg Tyr His Cys Lys Asp Gly Phe
                485                 490                 495

Ile Gln Arg His Leu Pro Thr Ile Arg Cys Leu Gly Asn Gly Arg Trp
                500                 505                 510

Ala Met Pro Lys Ile Thr Cys Met Asn Pro Ser Ala Tyr Gln Arg Thr
            515                 520                 525

Tyr Ser Lys Lys Tyr Leu Lys Asn Ser Ser Val Lys Asp Asn Ser
    530                 535                 540

Ile Asn Thr Ser Lys His Glu His Arg Trp Ser Arg Arg Trp Gln Glu
545                 550                 555                 560

Thr Arg Arg

<210> SEQ ID NO 12
<211> LENGTH: 1867
<212> TYPE: DNA
<213> ORGANISM: Artificial Sequence
<220> FEATURE:
<223> OTHER INFORMATION: DNA encoding engineered versican V-3-derived
      polypeptide having exon 6 deleted

<400> SEQUENCE: 12
taagccgcct ttcaaggaca agatgttgat aaatatgaac ggcatcctat ggatgtgctc      60
aaccttactg ttaacgcatg cactgcataa agccaaaatg gaagaaaacc cacctgttaa     120
aggctctctg tctggaaaag tgatcctacc ttgtcatttt tcaaccttgc ccaccttacc     180
acccgattac aacacgagtg aatttctcag aatcaaatgg tctaaaatag aagtggacaa     240
aaatggaaaa gacataaagg agactactgt cctggtggcc aagacgggaa acatcaagat     300
tggtcaggac tacaaggggc gggtatcagt gcctacgcat cccgatgacg taggcgatgc     360
ctctctcacc atggtcaaac tccgtgctag tgacgcaggt gtctaccgct gtgatgtcat     420
gtatggcatt gaagacactc agaacacgat gtcgctggcc gtggacggtg tcgtgtttca     480
ctacagggca gcgaccagca gatacactct gaacttcgag tctgctcaac aggcttgttt     540
ggacatcggg gcggtcatag caaccccaga gcagctgttc gctgcctatg aggatggatt     600
tgagcagtgt gatgcaggat ggctgtctga ccaaactgtc agatatccca tacgggctcc     660
ccgagagggc tgttatggag acatgatggg gaaggaaggg gtccggacct atgattccg      720 ctctccccag gaaacctatg atgtgtattg ctatgtggat catctggacg gcagatttga     780
tgcctactgc tttaaacgac tgatctctg caaaacaaac ccatgcctca atggaggcac     840

-continued

```
ctgctatcct actgagactt cctatgtgtg cacctgtgca cctggctaca gtggagacca      900
gtgtgaactg gattttgatg aatgtcactc taacccttgt cggaatggag ccacctgtgt      960
ggacggtctg aatacattta gatgcctctg ccttccgagt tatgtcggtg cactctgcga     1020
acaagacact gagacatgcg actatggctg gcacaaattc aagggcaat gctacaagta     1080 ctttgctcat cgccgtacat gggatgctgc tgaaagggag tgtcgcctgc agggtgccca     1140
cctcacaagc atcctttctc atgaggaaca aatgtttgtg aatcgtgtgg gccatgatta     1200
ccagtggatt ggcctcaatg acaagatgtt tgaacatgac ttccgctgga ctgacggcag     1260
cgcactgcaa tatgagaact ggagacccaa ccagccagac agcttctttt ctgctggaga     1320
agactgcgtt gtgatcattt ggcatgagaa tggccagtgg aatgacgtcc cctgcaacta     1380
ccacctcacc tacacctgca agaagggaac agttgcttgc ggccaacccc ctgttgtaga     1440
aaatgccaag cctttggaa agatgaaacc acgttatgaa atcaactcct tgattagata     1500
ccactgcaaa gatggtttca ttcagcgtca ccttccaact atccggtgcc taggaaatgg     1560
gagatgggca atgcctaaaa taacctgcat gaacccatct gcataccaaa ggacttattc     1620
taagaaatac ttaaaaaatt cctcatcagt caaggacaat tctataaata cgtcaaaaca     1680
tgagcatcgc tggagccgga ggtggcagga aacgaggcgc tgatcctaaa atggcgaaca     1740
taagcttcat tcatcatttc agccaaagcc ctgcctttcc gtgcctttcc tatcacctca     1800
aggagaatta gcagttggtt tggattttgg gactgccgtc tggtcatttg gggtggctgt     1860
attccta                                                               1867
```

<210> SEQ ID NO 13
<211> LENGTH: 566
<212> TYPE: PRT
<213> ORGANISM: Artificial Sequence
<220> FEATURE:
<223> OTHER INFORMATION: Engineered versican V-3-derived
      polypeptide having exon 6 deleted

<400> SEQUENCE: 13

```
Met Leu Ile Asn Met Asn Gly Ile Leu Trp Met Cys Ser Thr Leu Leu
 1               5                  10                  15

Leu Thr His Ala Leu His Lys Ala Lys Met Glu Glu Asn Pro Pro Val
             20                  25                  30

Lys Gly Ser Leu Ser Gly Lys Val Ile Leu Pro Cys His Phe Ser Thr
         35                  40                  45

Leu Pro Thr Leu Pro Pro Asp Tyr Asn Thr Ser Glu Phe Leu Arg Ile
     50                  55                  60

Lys Trp Ser Lys Ile Glu Val Asp Lys Asn Gly Lys Asp Ile Lys Glu
 65                  70                  75                  80

Thr Thr Val Leu Val Ala Gln Asp Gly Asn Ile Lys Ile Gly Gln Asp
                 85                  90                  95

Tyr Lys Gly Arg Val Ser Val Pro Thr His Pro Asp Val Gly Asp
                100                 105                 110

Ala Ser Leu Thr Met Val Lys Leu Arg Ala Ser Asp Ala Gly Val Tyr
            115                 120                 125

Arg Cys Asp Val Met Tyr Gly Ile Glu Asp Thr Gln Asn Thr Met Ser
        130                 135                 140

Leu Ala Val Asp Gly Val Val Phe His Tyr Arg Ala Ala Thr Ser Arg
145                 150                 155                 160

Tyr Thr Leu Asn Phe Glu Ser Ala Gln Gln Ala Cys Leu Asp Ile Gly
                165                 170                 175
```

```
Ala Val Ile Ala Thr Pro Glu Gln Leu Phe Ala Ala Tyr Glu Asp Gly
            180                 185                 190

Phe Glu Gln Cys Asp Ala Gly Trp Leu Ser Asp Gln Thr Val Arg Tyr
            195                 200                 205

Pro Ile Arg Ala Pro Arg Glu Gly Cys Tyr Gly Asp Met Met Gly Lys
            210                 215                 220

Glu Gly Val Arg Thr Tyr Gly Phe Arg Ser Pro Gln Glu Thr Tyr Asp
225                 230                 235                 240

Val Tyr Cys Tyr Val Asp His Leu Asp Gly Arg Phe Asp Ala Tyr Cys
                245                 250                 255

Phe Lys Arg Pro Asp Leu Cys Lys Thr Asn Pro Cys Leu Asn Gly Gly
            260                 265                 270

Thr Cys Tyr Pro Thr Glu Thr Ser Tyr Val Cys Thr Cys Ala Pro Gly
            275                 280                 285

Tyr Ser Gly Asp Gln Cys Glu Leu Asp Phe Asp Glu Cys His Ser Asn
            290                 295                 300

Pro Cys Arg Asn Gly Ala Thr Cys Val Asp Gly Leu Asn Thr Phe Arg
305                 310                 315                 320

Cys Leu Cys Leu Pro Ser Tyr Val Gly Ala Leu Cys Glu Gln Asp Thr
                325                 330                 335

Glu Thr Cys Asp Tyr Gly Trp His Lys Phe Gln Gly Asn Cys Tyr Lys
            340                 345                 350

Tyr Phe Ala His Arg Arg Thr Trp Asp Ala Ala Glu Arg Glu Cys Arg
            355                 360                 365

Leu Gln Gly Ala His Leu Thr Ser Ile Leu Ser His Glu Glu Gln Met
370                 375                 380

Phe Val Asn Arg Val Gly His Asp Tyr Gln Trp Ile Gly Leu Asn Asp
385                 390                 395                 400

Lys Met Phe Glu His Asp Phe Arg Trp Thr Asp Gly Ser Ala Leu Gln
                405                 410                 415

Tyr Glu Asn Trp Arg Pro Asn Gln Pro Asp Ser Phe Phe Ser Ala Gly
            420                 425                 430

Glu Asp Cys Val Val Ile Ile Trp His Glu Asn Gly Gln Trp Asn Asp
            435                 440                 445

Val Pro Cys Asn Tyr His Leu Thr Tyr Thr Cys Lys Lys Gly Thr Val
450                 455                 460

Ala Cys Gly Gln Pro Pro Val Val Glu Asn Ala Lys Thr Phe Gly Lys
465                 470                 475                 480

Met Lys Pro Arg Tyr Glu Ile Asn Ser Leu Ile Arg Tyr His Cys Lys
                485                 490                 495

Asp Gly Phe Ile Gln Arg His Leu Pro Thr Ile Arg Cys Leu Gly Asn
            500                 505                 510

Gly Arg Trp Ala Met Pro Lys Ile Thr Cys Met Asn Pro Ser Ala Tyr
            515                 520                 525

Gln Arg Thr Tyr Ser Lys Lys Tyr Leu Lys Asn Ser Ser Ser Val Lys
            530                 535                 540

Asp Asn Ser Ile Asn Thr Ser Lys His Glu His Arg Trp Ser Arg Arg
545                 550                 555                 560

Trp Gln Glu Thr Arg Arg
                565

<210> SEQ ID NO 14
<211> LENGTH: 1927
<212> TYPE: DNA
```

<210> SEQ ID NO 14
<211> LENGTH: 1927
<212> TYPE: DNA
<213> ORGANISM: Artificial Sequence
<220> FEATURE:
<223> OTHER INFORMATION: DNA encoding engineered versican V-3-derived polypeptide having exons 9 and 10 deleted

<400> SEQUENCE: 14

```
taagccgcct ttcaaggaca agatgttgat aaatatgaac ggcatcctat ggatgtgctc     60
aaccttactg ttaacgcatg cactgcataa agccaaaatg aagaaaacc cacctgttaa    120
aggctctctg tctggaaaag tgatcctacc ttgtcatttt tcaaccttgc ccaccttacc    180
acccgattac aacacgagtg aatttctcag aatcaaatgg tctaaaatag aagtggacaa    240
aaatggaaaa gacataaagg agactactgt cctggtggcc aagacgggga acatcaagat    300
tggtcaggac tacaaggggc gggtatcagt gcctacgcat cccgatgacg taggcgatgc    360
ctctctcacc atggtcaaac tccgtgctag tgacgcaggt gtctaccgct gtgatgtcat    420
gtatggcatt gaagacactc agaacacgat gtcgctggcc gtggacggtg tcgtgtttca    480
ctacagggca gcgaccagca gatacactct gaacttcgag tctgctcaac aggcttgttt    540
ggacatcggg gcggtcatag cagcccccaga gcagctgttc gctgcctatg aggatggatt    600
tgagcagtgt gatgcaggat ggctgtctga ccaaactgtc agatatccca tacgggctcc    660
ccgagagggc tgttatggag acatgatggg gaaggaaggg gtccggacct atggattccg    720
ctctccccag gaaacctatg atgtgtattg ctatgtggat catctggacg gcgatgtgtt    780
ccacatcact gctcccagta aattccactt cgaggaggcc gaagcagagt gtgcaaaccg    840
ggatgccagg ctggcgactg ttggggaact tcacgcagct tggaggaacg gctttgacca    900
gtgcgattac ggctggctgt cggatgccag cgtgcggcac cctgtgactg tggccagggc    960
ccagtgtgga ggtggtctac ttgggggtgag aaccctgtat cgttttgaga accagacatg   1020
cttccctctc cctgatagca gatttgatgc ctactgcttt aaacgacctg cactctgcga   1080
acaagacact gagacatgcg actatggctg gcacaaattc caagggcaat gctacaagta   1140
ctttgctcat cgccgtacat gggatgctgc tgaaagggag tgtcgcctgc agggtgccca   1200
cctcacaagc atcctttctc atgaggaaca aatgtttgtg aatcgtgtgg gccatgatta   1260
ccagtggatt ggcctcaatg acaagatgtt tgaacatgac ttccgctgga ctgacggcag   1320
cgcactgcaa tatgagaact ggagacccaa ccagccagac agcttcttt ctgctggaga   1380
agactgcgtt gtgatcattt ggcatgagaa tggccagtgg aatgacgtcc cctgcaacta   1440
ccacctcacc tacacctgca agaagggaac agttgcttgc ggccaacccc ctgttgtaga   1500
aaatgccaag acctttggaa agatgaaacc acgttatgaa atcaactcct tgattagata   1560
ccactgcaaa gatggtttca ttcagcgtca ccttccaact atccggtgcc taggaaatgg   1620
gagatgggca atgcctaaaa taacctgcat gaacccatct gcataccaaa ggacttattc   1680
taagaaatac ttaaaaaatt cctcatcagt caaggacaat tctataaata cgtcaaaaca   1740
tgagcatcgc tggagccgga ggtggcagga acgaggcgc tgatcctaaa atggcgaaca   1800
taagcttcat tcatcatttc agccaaagcc ctgcctttcc gtgcctttcc tatcacctca   1860
aggagaatta gcagttggtt tggattttgg gactgccgtc tggtcatttg gggtggctgt   1920
attccta                                                             1927
```

<210> SEQ ID NO 15
<211> LENGTH: 586
<212> TYPE: PRT
<213> ORGANISM: Artificial Sequence
<220> FEATURE:
<223> OTHER INFORMATION: Engineered versican V-3-derived polypeptide having exons 9 and 10 deleted

<400> SEQUENCE: 15

```
Met Leu Ile Asn Met Asn Gly Ile Leu Trp Met Cys Ser Thr Leu Leu
 1               5                  10                  15

Leu Thr His Ala Leu His Lys Ala Lys Met Glu Glu Asn Pro Pro Val
            20                  25                  30

Lys Gly Ser Leu Ser Gly Lys Val Ile Leu Pro Cys His Phe Ser Thr
        35                  40                  45

Leu Pro Thr Leu Pro Pro Asp Tyr Asn Thr Ser Glu Phe Leu Arg Ile
    50                  55                  60

Lys Trp Ser Lys Ile Glu Val Asp Lys Asn Gly Lys Asp Ile Lys Glu
65                  70                  75                  80

Thr Thr Val Leu Val Ala Gln Asp Gly Asn Ile Lys Ile Gly Gln Asp
                85                  90                  95

Tyr Lys Gly Arg Val Ser Val Pro Thr His Pro Asp Asp Val Gly Asp
            100                 105                 110

Ala Ser Leu Thr Met Val Lys Leu Arg Ala Ser Asp Ala Gly Val Tyr
        115                 120                 125

Arg Cys Asp Val Met Tyr Gly Ile Glu Asp Thr Gln Asn Thr Met Ser
    130                 135                 140

Leu Ala Val Asp Gly Val Val Phe His Tyr Arg Ala Ala Thr Ser Arg
145                 150                 155                 160

Tyr Thr Leu Asn Phe Glu Ser Ala Gln Gln Ala Cys Leu Asp Ile Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ser Asp Gln Thr Val Arg Tyr
        195                 200                 205

Pro Ile Arg Ala Pro Arg Glu Gly Cys Tyr Gly Asp Met Met Gly Lys
    210                 215                 220

Glu Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Ile Thr
                245                 250                 255

Ala Pro Ser Lys Phe Thr Phe Glu Glu Ala Glu Ala Cys Ala Asn
            260                 265                 270

Arg Asp Ala Arg Leu Ala Thr Val Gly Glu Leu His Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Cys Phe Pro Leu
                325                 330                 335

Pro Asp Ser Arg Phe Asp Ala Tyr Cys Phe Lys Arg Pro Ala Leu Cys
            340                 345                 350

Glu Gln Asp Thr Glu Thr Cys Asp Tyr Gly Trp His Lys Phe Gln Gly
        355                 360                 365

Gln Cys Tyr Lys Tyr Phe Ala His Arg Arg Thr Trp Asp Ala Ala Glu
    370                 375                 380

Arg Glu Cys Arg Leu Gln Gly Ala His Leu Thr Ser Ile Leu Ser His
385                 390                 395                 400

Glu Glu Gln Met Phe Val Asn Arg Val Gly His Asp Tyr Gln Trp Ile
```

405                 410                 415
Gly Leu Asn Asp Lys Met Phe Glu His Asp Phe Arg Trp Thr Asp Gly
            420                 425                 430

Ser Ala Leu Gln Tyr Glu Asn Trp Arg Pro Asn Gln Pro Asp Ser Phe
            435                 440                 445

Phe Ser Ala Gly Glu Asp Cys Val Val Ile Ile Trp His Glu Asn Gly
            450                 455                 460

Gln Trp Asn Asp Val Pro Cys Asn Tyr His Leu Thr Tyr Thr Cys Lys
465                 470                 475                 480

Lys Gly Thr Val Ala Cys Gly Gln Pro Pro Val Val Glu Asn Ala Lys
                485                 490                 495

Thr Phe Gly Lys Met Lys Pro Arg Tyr Glu Ile Asn Ser Leu Ile Arg
            500                 505                 510

Tyr His Cys Lys Asp Gly Phe Ile Gln Arg His Leu Pro Thr Ile Arg
            515                 520                 525

Cys Leu Gly Asn Gly Arg Trp Ala Met Pro Lys Ile Thr Cys Met Asn
            530                 535                 540

Pro Ser Ala Tyr Gln Arg Thr Tyr Ser Lys Lys Tyr Leu Lys Asn Ser
545                 550                 555                 560

Ser Ser Val Lys Asp Asn Ser Ile Asn Thr Ser Lys His Glu His Arg
                565                 570                 575

Trp Ser Arg Arg Trp Gln Glu Thr Arg Arg
            580                 585

<210> SEQ ID NO 16
<211> LENGTH: 1804
<212> TYPE: DNA
<213> ORGANISM: Artificial Sequence
<220> FEATURE:
<223> OTHER INFORMATION: DNA encoding engineered versican V-3-derived
      polypeptide having exons 11-13 deleted

<400> SEQUENCE: 16
taagccgcct ttcaaggaca agatgttgat aaatatgaac ggcatcctat ggatgtgctc      60
aaccttactg ttaacgcatg cactgcataa agccaaaatg gaagaaaacc cacctgttaa     120
aggctctctg tctggaaaag tgatcctacc ttgtcatttt tcaaccttgc ccaccttacc     180
acccgattac aacacgagtg aatttctcag aatcaaatgg tctaaaatag aagtggacaa     240
aaatggaaaa gacataaagg agactactgt cctggtggcc caagacggga acatcaagat     300
tggtcaggac tacaaggggc gggtatcagt gcctacgcat cccgatgacg taggcgatgc     360
ctctctcacc atggtcaaac tccgtgctag tgacgcaggt gtctaccgct gtgatgtcat     420
gtatggcatt gaagacactc agaacacgat gtcgctggcc gtggacggtg tcgtgtttca     480
ctacagggca gcgaccagca gatacactct gaacttcgag tctgctcaac aggcttgttt     540
ggacatcggg gcggtcatag caaccccaga gcagctgttc gctgcctatg aggatggatt     600
tgagcagtgt gatgcaggat ggctgtctga ccaaactgtc agatatccca tacgggctcc     660
ccgagagggc tgttatggag acatgatggg gaaggaaggg gtccggacct atggattccg     720
ctctccccag gaaacctatg atgtgtattg ctatgtggat catctggacg gcgatgtgtt     780
ccacatcact gctcccagta aattcacctt cgaggaggcc gaagcagagt gtgcaaaccg     840
ggatgccagg ctggcgactg ttggggaact tcacgcagct ggaggaacg gctttgacca     900 gtgcgattac ggctggctgt cggatgccag cgtgcggcac cctgtgactg tggccagggc     960
ccagtgtgga ggtggtctac ttggggtgag aaccctgtat cgttttgaga accagacatg    1020

-continued

```
cttccctctc cctgatagca gatttgatgc ctactgcttt aaacgacctg atctctgcaa    1080
aacaaaccca tgcctcaatg gaggcacctg ctatcctact gagacttcct atgtgtgcac    1140
ctgtgcacct ggctacagtg gagaccagtg tgaactggat tttgatgaat gtcactctaa    1200
cccttgtcgg aatggagcca cctgtgtgga cggtctgaat acatttagat gcctctgcct    1260
tccgagttat gtcggtgcac tctgcgaaca agacactgag acatgcccct gcaactacca    1320
cctcacctac acctgcaaga agggaacagt tgcttgcggc caaccccctg ttgtagaaaa    1380
tgccaagacc tttggaaaga tgaaaccacg ttatgaaatc aactccttga ttagatacca    1440
ctgcaaagat ggtttcattc agcgtcacct tccaactatc cggtgcctag gaaatgggag    1500
atgggcaatg cctaaaataa cctgcatgaa cccatctgca taccaaagga cttattctaa    1560
gaaatactta aaaaattcct catcagtcaa ggacaattct ataaatacgt caaaacatga    1620
gcatcgctgg agccggaggt ggcaggaaac gaggcgctga tcctaaaatg gcgaacataa    1680
gcttcattca tcatttcagc caaagccctg cctttccgtg cctttcctat cacctcaagg    1740
agaattagca gttggtttgg attttgggac tgccgtctgg tcatttgggg tggctgtatt    1800
ccta                                                                 1804
```

<210> SEQ ID NO 17
<211> LENGTH: 545
<212> TYPE: PRT
<213> ORGANISM: Artificial Sequence
<220> FEATURE:
<223> OTHER INFORMATION: Engineered versican V-3-derived
      polypeptide having exons 11-13 deleted

<400> SEQUENCE: 17

```
Met Leu Ile Asn Met Asn Gly Ile Leu Trp Met Cys Ser Thr Leu Leu
  1               5                  10                  15

Leu Thr His Ala Leu His Lys Ala Lys Met Glu Glu Asn Pro Pro Val
             20                  25                  30

Lys Gly Ser Leu Ser Gly Lys Val Ile Leu Pro Cys His Phe Ser Thr
         35                  40                  45

Leu Pro Thr Leu Pro Pro Asp Tyr Asn Thr Ser Glu Phe Leu Arg Ile
     50                  55                  60

Lys Trp Ser Lys Ile Glu Val Asp Lys Asn Gly Lys Asp Ile Lys Glu
 65                  70                  75                  80

Thr Thr Val Leu Val Ala Gln Asp Gly Asn Ile Lys Ile Gly Gln Asp
                 85                  90                  95

Tyr Lys Gly Arg Val Ser Val Pro Thr His Pro Asp Asp Val Gly Asp
            100                 105                 110

Ala Ser Leu Thr Met Val Lys Leu Arg Ala Ser Asp Ala Gly Val Tyr
        115                 120                 125

Arg Cys Asp Val Met Tyr Gly Ile Glu Asp Thr Gln Asn Thr Met Ser
    130                 135                 140

Leu Ala Val Asp Gly Val Val Phe His Tyr Arg Ala Ala Thr Ser Arg
145                 150                 155                 160

Tyr Thr Leu Asn Phe Glu Ser Ala Gln Gln Ala Cys Leu Asp Ile Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ser Asp Gln Thr Val Arg Tyr
        195                 200                 205

Pro Ile Arg Ala Pro Arg Glu Gly Cys Tyr Gly Asp Met Met Gly Lys
    210                 215                 220
```

```
Glu Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Ile Thr
            245                 250                 255

Ala Pro Ser Lys Phe Thr Phe Glu Glu Ala Glu Ala Glu Cys Ala Asn
        260                 265                 270

Arg Asp Ala Arg Leu Ala Thr Val Gly Glu Leu His Ala Ala Trp Arg
    275                 280                 285

Asn Gly Phe Asp Gln Cys Asp Tyr Gly Trp Leu Ser Asp Ala Ser Val
290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Cys Phe Pro Leu
                325                 330                 335

Pro Asp Ser Arg Phe Asp Ala Tyr Cys Phe Lys Arg Pro Asp Leu Cys
            340                 345                 350

Lys Thr Asn Pro Cys Leu Asn Gly Gly Thr Cys Tyr Pro Thr Glu Thr
        355                 360                 365

Ser Tyr Val Cys Thr Cys Ala Pro Gly Tyr Ser Gly Asp Gln Cys Glu
    370                 375                 380

Leu Asp Phe Asp Glu Cys His Ser Asn Pro Cys Arg Asn Gly Ala Thr
385                 390                 395                 400

Cys Val Asp Gly Leu Asn Thr Phe Arg Cys Leu Cys Leu Pro Ser Tyr
                405                 410                 415

Val Gly Ala Leu Cys Glu Gln Asp Thr Glu Thr Cys Pro Cys Asn Tyr
            420                 425                 430

His Leu Thr Tyr Thr Cys Lys Lys Gly Thr Val Ala Cys Gly Gln Pro
        435                 440                 445

Pro Val Val Glu Asn Ala Lys Thr Phe Gly Lys Met Lys Pro Arg Tyr
    450                 455                 460

Glu Ile Asn Ser Leu Ile Arg Tyr His Cys Lys Asp Gly Phe Ile Gln
465                 470                 475                 480

Arg His Leu Pro Thr Ile Arg Cys Leu Gly Asn Gly Arg Trp Ala Met
                485                 490                 495

Pro Lys Ile Thr Cys Met Asn Pro Ser Ala Tyr Gln Arg Thr Tyr Ser
            500                 505                 510

Lys Lys Tyr Leu Lys Asn Ser Ser Val Lys Asp Asn Ser Ile Asn
        515                 520                 525

Thr Ser Lys His Glu His Arg Trp Ser Arg Arg Trp Gln Glu Thr Arg
    530                 535                 540

Arg
545

<210> SEQ ID NO 18
<211> LENGTH: 1939
<212> TYPE: DNA
<213> ORGANISM: Artificial Sequence
<220> FEATURE:
<223> OTHER INFORMATION: DNA encoding engineered versican V-3-derived
      polypeptide having exon 14 deleted

<400> SEQUENCE: 18
taagccgcct ttcaaggaca agatgttgat aaatatgaac ggcatcctat ggatgtgctc      60
aaccttactg ttaacgcatg cactgcataa agccaaaatg gaagaaaacc cacctgttaa     120
aggctctctg tctggaaaag tgatcctacc ttgtcatttt tcaaccttgc ccaccttacc    180
```

```
acccgattac aacacgagtg aatttctcag aatcaaatgg tctaaaatag aagtggacaa    240 aaaatggaaaa gacataaagg agactactgt cctggtggcc aagacgggga acatcaagat    300
tggtcaggac tacaaggggc gggtatcagt gcctacgcat cccgatgacg taggcgatgc    360
ctctctcacc atggtcaaac tccgtgctag tgacgcaggt gtctaccgct gtgatgtcat    420
gtatggcatt gaagacactc agaacacgat gtcgctggcc gtggacggtg tcgtgtttca    480
ctacagggca gcgaccagca gatacactct gaacttcgag tctgctcaac aggcttgttt    540
ggacatcggg gcggtcatag caaccccaga gcagctgttc gctgcctatg aggatggatt    600
tgagcagtgt gatgcaggat ggctgtctga ccaaactgtc agatatccca tacgggctcc    660
ccgagagggc tgttatggag acatgatggg aaggaaggg gtccggacct atggattccg    720
ctctccccag gaaacctatg atgtgtattg ctatgtggat catctggacg gcgatgtgtt    780
ccacatcact gctcccagta aattcacctt cgaggaggcc gaagcagagt gtgcaaaccg    840
ggatgccagg ctggcgactg ttggggaact tcacgcagct tggaggaacg cttttgacca    900
gtgcgattac ggctggctgt cggatgccag cgtgcggcac cctgtgactg tggccagggc    960
ccagtgtgga ggtggtctac ttggggtgag aaccctgtat cgttttgaga ccagacatg    1020 cttccctctc cctgatagca gatttgatgc ctactgcttt aaacgacctg atctctgcaa    1080
aacaaaccca tgcctcaatg gaggcacctg ctatcctact gagacttcct atgtgtgcac    1140
ctgtgcacct ggctacagtg agaccagtg tgaactggat tttgatgaat gtcactctaa    1200 ccctttgtcgg aatggagcca cctgtgtgga cggtctgaat acatttagat gcctctgcct    1260
tccgagttat gtcggtgcac tctgcgaaca agacactgag acatgcgact atggctggca    1320
caaattccaa gggcaatgct acaagtactt tgctcatcgc cgtacatggg atgctgctga    1380
aagggagtgt cgcctgcagg gtgcccacct cacaagcatc ctttctcatg aggaacaaat    1440
gtttgtgaat cgtgtgggcc atgattacca gtggattggc ctcaatgaca agatgtttga    1500
acatgacttc cgctggactg acggcagcgc actgcaatat gagaactgga gacccaacca    1560
gccagacagc ttcttttctg ctggagaaga ctgcgttgtg atcatttggc atgagaatgg    1620
ccagtggaat gacgtccct gcaactacca cctcacctac acctgcccat ctgcatacca    1680
aaggacttat tctaagaaat acttaaaaaa ttcctcatca gtcaaggaca attctataaa    1740
tacgtcaaaa catgagcatc gctggagccg gaggtggcag gaaacgaggc gctgatccta    1800 aaaatggcgaa cataagcttc attcatcatt tcagccaaag ccctgccttt ccgtgccttt    1860
cctatcacct caaggagaat tagcagttgg tttggatttt gggactgccg tctggtcatt    1920
tggggtggct gtattccta                                                 1939
```

<210> SEQ ID NO 19
<211> LENGTH: 590
<212> TYPE: PRT
<213> ORGANISM: Artificial Sequence
<220> FEATURE:
<223> OTHER INFORMATION: Engineered versican V-3-derived
      polypeptide having exon 14 deleted

<400> SEQUENCE: 19

```
Met Leu Ile Asn Met Asn Gly Ile Leu Trp Met Cys Ser Thr Leu Leu
  1               5                  10                  15

Leu Thr His Ala Leu His Lys Ala Lys Met Glu Glu Asn Pro Pro Val
             20                  25                  30

Lys Gly Ser Leu Ser Gly Lys Val Ile Leu Pro Cys His Phe Ser Thr
         35                  40                  45
```

-continued

```
Leu Pro Thr Leu Pro Pro Asp Tyr Asn Thr Ser Glu Phe Leu Arg Ile
     50                  55                  60
Lys Trp Ser Lys Ile Glu Val Asp Lys Asn Gly Lys Asp Ile Lys Glu
 65                  70                  75                  80
Thr Thr Val Leu Val Ala Gln Asp Gly Asn Ile Lys Ile Gly Gln Asp
                 85                  90                  95
Tyr Lys Gly Arg Val Ser Val Pro Thr His Pro Asp Asp Val Gly Asp
            100                 105                 110
Ala Ser Leu Thr Met Val Lys Leu Arg Ala Ser Asp Ala Gly Val Tyr
        115                 120                 125
Arg Cys Asp Val Met Tyr Gly Ile Glu Asp Thr Gln Asn Thr Met Ser
    130                 135                 140
Leu Ala Val Asp Gly Val Val Phe His Tyr Arg Ala Ala Thr Ser Arg
145                 150                 155                 160
Tyr Thr Leu Asn Phe Glu Ser Ala Gln Gln Ala Cys Leu Asp Ile Gly
                165                 170                 175
Ala Val Ile Ala Thr Pro Glu Gln Leu Phe Ala Ala Tyr Glu Asp Gly
            180                 185                 190
Phe Glu Gln Cys Asp Ala Gly Trp Leu Ser Asp Gln Thr Val Arg Tyr
        195                 200                 205
Pro Ile Arg Ala Pro Arg Glu Gly Cys Tyr Gly Asp Met Met Gly Lys
    210                 215                 220
Glu Gly Val Arg Thr Tyr Gly Phe Arg Ser Pro Gln Glu Thr Tyr Asp
225                 230                 235                 240
Val Tyr Cys Tyr Val Asp His Leu Asp Gly Asp Val Phe His Ile Thr
                245                 250                 255
Ala Pro Ser Lys Phe Thr Phe Glu Glu Ala Glu Ala Glu Cys Ala Asn
            260                 265                 270
Arg Asp Ala Arg Leu Ala Thr Val Gly Glu Leu His Ala Ala Trp Arg
        275                 280                 285
Asn Gly Phe Asp Gln Cys Asp Tyr Gly Trp Leu Ser Asp Ala Ser Val
    290                 295                 300
Arg His Pro Val Thr Val Ala Arg Ala Gln Cys Gly Gly Gly Leu Leu
305                 310                 315                 320
Gly Val Arg Thr Leu Tyr Arg Phe Glu Asn Gln Thr Cys Phe Pro Leu
                325                 330                 335
Pro Asp Ser Arg Phe Asp Ala Tyr Cys Phe Lys Arg Pro Asp Leu Cys
            340                 345                 350
Lys Thr Asn Pro Cys Leu Asn Gly Gly Thr Cys Tyr Pro Thr Glu Thr
        355                 360                 365
Ser Tyr Val Cys Thr Cys Ala Pro Gly Tyr Ser Gly Asp Gln Cys Glu
    370                 375                 380
Leu Asp Phe Asp Glu Cys His Ser Asn Pro Cys Arg Asn Gly Ala Thr
385                 390                 395                 400
Cys Val Asp Gly Leu Asn Thr Phe Arg Cys Leu Cys Leu Pro Ser Tyr
                405                 410                 415
Val Gly Ala Leu Cys Glu Gln Asp Thr Glu Thr Cys Asp Tyr Gly Trp
            420                 425                 430
His Lys Phe Gln Gly Gln Cys Tyr Lys Tyr Phe Ala His Arg Arg Thr
        435                 440                 445
Trp Asp Ala Ala Glu Arg Glu Cys Arg Leu Gln Gly Ala His Leu Thr
    450                 455                 460
Ser Ile Leu Ser His Glu Glu Gln Met Phe Val Asn Arg Val Gly His
```

```
                465                 470                 475                 480
Asp Tyr Gln Trp Ile Gly Leu Asn Asp Lys Met Phe Glu His Asp Phe
                            485                 490                 495

Arg Trp Thr Asp Gly Ser Ala Leu Gln Tyr Glu Asn Trp Arg Pro Asn
                500                 505                 510

Gln Pro Asp Ser Phe Phe Ser Ala Gly Glu Asp Cys Val Val Ile Ile
            515                 520                 525

Trp His Glu Asn Gly Gln Trp Asn Asp Val Pro Cys Asn Tyr His Leu
        530                 535                 540

Thr Tyr Thr Cys Pro Ser Ala Tyr Gln Arg Thr Tyr Ser Lys Lys Tyr
545                 550                 555                 560

Leu Lys Asn Ser Ser Val Lys Asp Asn Ser Ile Asn Thr Ser Lys
                565                 570                 575

His Glu His Arg Trp Ser Arg Arg Trp Gln Glu Thr Arg Arg
            580                 585                 590

<210> SEQ ID NO 20
<211> LENGTH: 1561
<212> TYPE: DNA
<213> ORGANISM: Artificial Sequence
<220> FEATURE:
<223> OTHER INFORMATION: DNA encoding engineered versican V-3-derived
      polypeptide having exons 4-5-6 deleted

<400> SEQUENCE: 20
taagccgcct ttcaaggaca agatgttgat aaatatgaac ggcatcctat ggatgtgctc      60
aaccttactg ttaacgcatg cactgcataa agccaaaatg aagaaaacc cacctgttaa     120 aggctctctg tctggaaaag tgatcctacc ttgtcatttt tcaaccttgc ccaccttacc    180
acccgattac aacacgagtg aatttctcag aatcaaatgg tctaaaatag aagtggacaa    240
aaatggaaaa gacataaagg agactactgt cctggtggcc aagacggga acatcaagat     300 tggtcaggac tacaagggc gggtatcagt gcctacgcat cccgatgacg taggcgatgc    360
ctctctcacc atggtcaaac tccgtgctag tgacgcaggt gtctaccgct gtgatgtcat    420
gtatggcatt gaagacactc agaacacgat gtcgctggcc gtggacagat ttgatgccta    480
ctgctttaaa cgacctgatc tctgcaaaac aaacccatgc ctcaatggag cacctgcta    540 tcctactgag acttcctatg tgtgcacctg tgcacctggc tacagtggag accagtgtga    600
actggatttt tgatgaatgtc actctaaccc ttgtcggaat ggagccacct gtgtggacgg    660
tctgaataca tttagatgcc tctgccttcc gagttatgtc ggtgcactct gcgaacaaga    720
cactgagaca tgcgactatg ctggcacaa attccaaggg caatgctaca agtactttgc    780
tcatcgccgt acatgggatg ctgctgaaag ggagtgtcgc ctgcagggtg cccacctcac    840
aagcatcctt tctcatgagg aacaaatgtt tgtgaatcgt gtgggccatg attaccagtg    900
gattggcctc aatgacaaga tgtttgaaca tgacttccgc tggactacg gcagcgcact    960 gcaatatgag aactggagac caaccagcc agacagcttc ttttctgctg gagaagactg   1020
cgttgtgatc atttggcatg agaatggcca gtggaatgac gtcccctgca actaccacct   1080
cacctacacc tgcaagaagg gaacagttgc ttgcggccaa ccccctgttg tagaaaatgc   1140
caagaccttt ggaaagatga aaccacgtta tgaaatcaac tccttgatta gataccactg   1200
caaagatggt ttcattcagc gtcaccttcc aactatccgg tgcctaggaa atgggagatg   1260
ggcaatgcct aaaataaacct gcatgaaccc atctgcatac caaaggactt attctaagaa   1320
atacttaaaa aattcctcat cagtcaagga caattctata aatacgtcaa acatgagca    1380
```

-continued

```
tcgctggagc cggaggtggc aggaaacgag gcgctgatcc taaaatggcg aacataagct    1440
tcattcatca tttcagccaa agccctgcct ttccgtgcct ttcctatcac ctcaaggaga    1500
attagcagtt ggtttggatt ttgggactgc cgtctggtca tttggggtgg ctgtattcct    1560
a                                                                    1561
```

<210> SEQ ID NO 21
<211> LENGTH: 464
<212> TYPE: PRT
<213> ORGANISM: Artificial Sequence
<220> FEATURE:
<223> OTHER INFORMATION: Engineered versican V-3-derived
      polypeptide having exons 4-5-6 deleted

<400> SEQUENCE: 21

```
Met Leu Ile Asn Met Asn Gly Ile Leu Trp Met Cys Ser Thr Leu Leu
 1               5                  10                  15

Leu Thr His Ala Leu His Lys Ala Lys Met Glu Glu Asn Pro Pro Val
            20                  25                  30

Lys Gly Ser Leu Ser Gly Lys Val Ile Leu Pro Cys His Phe Ser Thr
        35                  40                  45

Leu Pro Thr Leu Pro Pro Asp Tyr Asn Thr Ser Glu Phe Leu Arg Ile
    50                  55                  60

Lys Trp Ser Lys Ile Glu Val Asp Lys Asn Gly Lys Asp Ile Lys Glu
65                  70                  75                  80

Thr Thr Val Leu Val Ala Gln Asp Gly Asn Ile Lys Ile Gly Gln Asp
                85                  90                  95

Tyr Lys Gly Arg Val Ser Val Pro Thr His Pro Asp Asp Val Gly Asp
            100                 105                 110

Ala Ser Leu Thr Met Val Lys Leu Arg Ala Ser Asp Ala Gly Val Tyr
        115                 120                 125

Arg Cys Asp Val Met Tyr Gly Ile Glu Asp Thr Gln Asn Thr Met Ser
    130                 135                 140

Leu Ala Val Asp Arg Phe Asp Ala Tyr Cys Phe Lys Arg Pro Asp Leu
145                 150                 155                 160

Cys Lys Thr Asn Pro Cys Leu Asn Gly Gly Thr Cys Tyr Pro Thr Glu
                165                 170                 175

Thr Ser Tyr Val Cys Thr Cys Ala Pro Gly Tyr Ser Gly Asp Gln Cys
            180                 185                 190

Glu Leu Asp Phe Asp Glu Cys His Ser Asn Pro Cys Arg Asn Gly Ala
        195                 200                 205

Thr Cys Val Asp Gly Leu Asn Thr Phe Arg Cys Leu Cys Leu Pro Ser
    210                 215                 220

Tyr Val Gly Ala Leu Cys Glu Gln Asp Thr Glu Thr Cys Asp Tyr Gly
225                 230                 235                 240

Trp His Lys Phe Gln Gly Gln Cys Tyr Lys Tyr Phe Ala His Arg Arg
                245                 250                 255

Thr Trp Asp Ala Ala Glu Arg Glu Cys Arg Leu Gln Gly Ala His Leu
            260                 265                 270

Thr Ser Ile Leu Ser His Glu Glu Gln Met Phe Val Asn Arg Val Gly
        275                 280                 285

His Asp Tyr Gln Trp Ile Gly Leu Asn Asp Lys Met Phe Glu His Asp
    290                 295                 300

Phe Arg Trp Thr Asp Gly Ser Ala Leu Gln Tyr Glu Asn Trp Arg Pro
305                 310                 315                 320

Asn Gln Pro Asp Ser Phe Phe Ser Ala Gly Glu Asp Cys Val Val Ile
```

|  | 325 |  |  |  | 330 |  |  |  |  | 335 |  |
|---|---|---|---|---|---|---|---|---|---|---|---|
| Ile | Trp | His | Glu | Asn | Gly | Gln | Trp | Asn | Asp | Val | Pro | Cys | Asn | Tyr | His |
|  |  |  | 340 |  |  |  |  | 345 |  |  |  |  | 350 |  |  |

Leu Thr Tyr Thr Cys Lys Lys Gly Thr Val Ala Cys Gly Gln Pro Pro
            355                 360                 365

Val Val Glu Asn Ala Lys Thr Phe Gly Lys Met Lys Pro Arg Tyr Glu
        370                 375                 380

Ile Asn Ser Leu Ile Arg Tyr His Cys Lys Asp Gly Phe Ile Gln Arg
385                 390                 395                 400

His Leu Pro Thr Ile Arg Cys Leu Gly Asn Gly Arg Trp Ala Met Pro
                405                 410                 415

Lys Ile Thr Cys Met Asn Pro Ser Ala Tyr Gln Arg Thr Tyr Ser Lys
                420                 425                 430

Lys Tyr Leu Lys Asn Ser Ser Val Lys Asp Asn Ser Ile Asn Thr
            435                 440                 445

Ser Lys His Glu His Arg Trp Ser Arg Arg Trp Gln Glu Thr Arg Arg
    450                 455                 460

<210> SEQ ID NO 22
<211> LENGTH: 1858
<212> TYPE: DNA
<213> ORGANISM: Artificial Sequence
<220> FEATURE:
<223> OTHER INFORMATION: DNA encoding engineered versican V-3-derived
      polypeptide having exons 4-5 deleted

<400> SEQUENCE: 22

```
taagccgcct tcaaggaca agatgttgat aaatatgaac ggcatcctat ggatgtgctc      60
aaccttactg ttaacgcatg cactgcataa agccaaaatg gaagaaaacc cacctgttaa     120
aggctctctg tctggaaaag tgatcctacc ttgtcatttt tcaaccttgc ccaccttacc    180
acccgattac aacacgagtg aatttctcag aatcaaatgg tctaaaatag aagtggacaa    240
aaatggaaaa gacataaagg agactactgt cctggtggcc aagacgggga catcaagat    300 tggtcaggac tacaaggggc gggtatcagt gcctacgcat cccgatgacg taggcgatgc    360
ctctctcacc atggtcaaac tccgtgctag tgacgcaggt gtctaccgct gtgatgtcat    420
gtatggcatt gaagacactc agaacacgat gtcgctggcc gtggacgtgt attgctatgt    480
ggatcatctg gacggcgatg tgttccacat cactgctccc agtaaattca ccttcgagga    540
ggccgaagca gagtgtgcaa accgggatgc caggctggcg actgttgggg aacttcacgc    600
agcttggagg aacggctttg accagtgcga ttacggctgg ctgtcggatg ccagcgtgcg    660 gcacccctgtg actgtggcca gggcccagtg tggaggtggt ctacttgggg tgagaacct    720 gtatcgtttt gagaaccaga catgcttccc tctccctgat agcagatttg atgcctactg    780
ctttaaacga cctgatctct gcaaaacaaa cccatgcctc aatggaggca cctgctatcc    840
tactgagact tcctatgtgt gcacctgtgc acctggctac agtggagacc agtgtgaact    900
ggattttgat gaatgtcact ctaacccttg tcggaatgga ccacctgtg tggacggtct    960 gaatacattt agatgcctct gccttccgag ttatgtcggt gcactctgcg aacaagacac   1020
tgagacatgc gactatggct ggcacaaatt ccaagggcaa tgctacaagt actttgctca   1080
tcgccgtaca tgggatgctg ctgaaaggga gtgtcgcctg cagggtgccc acctcacaag   1140 catccttttct catgaggaac aaatgtttgt gaatcgtgtg ggccatgatt accagtggat   1200
tggcctcaat gacaagatgt ttgaacatga cttccgctgg actgacgca gcgcactgca   1260 atatgagaac tggagaccca accagccaga cagcttcttt tctgctggag aagactgcgt   1320
```

```
tgtgatcatt tggcatgaga atggccagtg gaatgacgtc ccctgcaact accacctcac    1380
ctacacctgc aagaagggaa cagttgcttg cggccaaccc cctgttgtag aaaatgccaa    1440
gacctttgga aagatgaaac cacgttatga aatcaactcc ttgattagat accactgcaa    1500
agatggtttc attcagcgtc accttccaac tatccggtgc ctaggaaatg ggagatgggc    1560
aatgcctaaa ataacctgca tgaacccatc tgcataccaa aggacttatt ctaagaaata    1620
cttaaaaaat tcctcatcag tcaaggacaa ttctataaat acgtcaaaac atgagcatcg    1680
ctggagccgg aggtggcagg aaacgaggcg ctgatcctaa aatggcgaac ataagcttca    1740
ttcatcattt cagccaaagc cctgcctttc cgtgcctttc ctatcacctc aaggagaatt    1800
agcagttggt ttggattttg ggactgccgt ctggtcattt ggggtggctg tattccta      1858
```

<210> SEQ ID NO 23
<211> LENGTH: 563
<212> TYPE: PRT
<213> ORGANISM: Artificial Sequence
<220> FEATURE:
<223> OTHER INFORMATION: Engineered versican V-3-derived
       polypeptide having exons 4-5 deleted

<400> SEQUENCE: 23

```
Met Leu Ile Asn Met Asn Gly Ile Leu Trp Met Cys Ser Thr Leu Leu
 1               5                   10                  15

Leu Thr His Ala Leu His Lys Ala Lys Met Glu Glu Asn Pro Pro Val
            20                  25                  30

Lys Gly Ser Leu Ser Gly Lys Val Ile Leu Pro Cys His Phe Ser Thr
        35                  40                  45

Leu Pro Thr Leu Pro Pro Asp Tyr Asn Thr Ser Glu Phe Leu Arg Ile
    50                  55                  60

Lys Trp Ser Lys Ile Glu Val Asp Lys Asn Gly Lys Asp Ile Lys Glu
65                  70                  75                  80

Thr Thr Val Leu Val Ala Gln Asp Gly Asn Ile Lys Ile Gly Gln Asp
                85                  90                  95

Tyr Lys Gly Arg Val Ser Val Pro Thr His Pro Asp Asp Val Gly Asp
            100                 105                 110

Ala Ser Leu Thr Met Val Lys Leu Arg Ala Ser Asp Ala Gly Val Tyr
        115                 120                 125

Arg Cys Asp Val Met Tyr Gly Ile Glu Asp Thr Gln Asn Thr Met Ser
    130                 135                 140

Leu Ala Val Asp Val Tyr Cys Tyr Val Asp His Leu Asp Ser Gly Asp Val
145                 150                 155                 160

Phe His Ile Thr Ala Pro Ser Lys Phe Thr Phe Glu Glu Ala Glu Ala
                165                 170                 175

Glu Cys Ala Asn Arg Asp Ala Arg Leu Ala Thr Val Gly Glu Leu His
            180                 185                 190

Ala Ala Trp Arg Asn Gly Phe Asp Gln Cys Asp Tyr Gly Trp Leu Ser
        195                 200                 205

Asp Ala Ser Val Arg His Pro Val Thr Val Ala Arg Ala Gln Cys Gly
    210                 215                 220

Gly Gly Leu Leu Gly Val Arg Thr Leu Tyr Arg Phe Glu Asn Gln Thr
225                 230                 235                 240

Cys Phe Pro Leu Pro Asp Ser Arg Phe Asp Ala Tyr Cys Phe Lys Arg
                245                 250                 255

Pro Asp Leu Cys Lys Thr Asn Pro Cys Leu Asn Gly Gly Thr Cys Tyr
            260                 265                 270
```

Pro Thr Glu Thr Ser Tyr Val Cys Thr Cys Ala Pro Gly Tyr Ser Gly
            275                 280                 285

Asp Gln Cys Glu Leu Asp Phe Asp Glu Cys His Ser Asn Pro Cys Arg
        290                 295                 300

Asn Gly Ala Thr Cys Val Asp Gly Leu Asn Thr Phe Arg Cys Leu Cys
305                 310                 315                 320

Leu Pro Ser Tyr Val Gly Ala Leu Cys Glu Gln Asp Thr Glu Thr Cys
                325                 330                 335

Asp Tyr Gly Trp His Lys Phe Gln Gly Gln Cys Tyr Lys Tyr Phe Ala
            340                 345                 350

His Arg Arg Thr Trp Asp Ala Ala Glu Arg Glu Cys Arg Leu Gln Gly
        355                 360                 365

Ala His Leu Thr Ser Ile Leu Ser His Glu Glu Gln Met Phe Val Asn
    370                 375                 380

Arg Val Gly His Asp Tyr Gln Trp Ile Gly Leu Asn Asp Lys Met Phe
385                 390                 395                 400

Glu His Asp Phe Arg Trp Thr Asp Gly Ser Ala Leu Gln Tyr Glu Asn
                405                 410                 415

Trp Arg Pro Asn Gln Pro Asp Ser Phe Phe Ser Ala Gly Glu Asp Cys
            420                 425                 430

Val Val Ile Ile Trp His Glu Asn Gly Gln Trp Asn Asp Val Pro Cys
        435                 440                 445

Asn Tyr His Leu Thr Tyr Thr Cys Lys Lys Gly Thr Val Ala Cys Gly
    450                 455                 460

Gln Pro Pro Val Val Glu Asn Ala Lys Thr Phe Gly Lys Met Lys Pro
465                 470                 475                 480

Arg Tyr Glu Ile Asn Ser Leu Ile Arg Tyr His Cys Lys Asp Gly Phe
                485                 490                 495

Ile Gln Arg His Leu Pro Thr Ile Arg Cys Leu Gly Asn Gly Arg Trp
            500                 505                 510

Ala Met Pro Lys Ile Thr Cys Met Asn Pro Ser Ala Tyr Gln Arg Thr
        515                 520                 525

Tyr Ser Lys Lys Tyr Leu Lys Asn Ser Ser Ser Val Lys Asp Asn Ser
    530                 535                 540

Ile Asn Thr Ser Lys His Glu His Arg Trp Ser Arg Arg Trp Gln Glu
545                 550                 555                 560

Thr Arg Arg

<210> SEQ ID NO 24
<211> LENGTH: 1813
<212> TYPE: DNA
<213> ORGANISM: Artificial Sequence
<220> FEATURE:
<223> OTHER INFORMATION: DNA encoding engineered versican V-3-derived
      polypeptide having exons 3-4-5 deleted

<400> SEQUENCE: 24
taagccgcct ttcaaggaca agatgttgat aaatatgaac ggcatcctat ggatgtgctc      60
aaccttactg ttaacgcatg cactgcataa agccaaaatg gaagaaaacc cacctgttaa     120
aggctctctg tctggaaaag tgatcggtgt cgtgtttcac tacagggcag cgaccagcag     180
atacactctg aacttcgagt ctgctcaaca ggcttgtttg gacatcgggg cggtcatagc     240
aaccccagag cagctgttcg ctgcctatga ggatggattt gagcagtgtg atgcaggatg     300
gctgtctgac caaactgtca gatatcccat acgggctccc cgagagggct gttatggaga     360

```
catgatgggg aaggaagggg tccggaccta tggattccgc tctccccagg aaacctatga    420
tgtgtattgc tatgtggatc atctggacgg cgatgtgttc cacatcactg ctcccagtaa    480
attcaccttc gaggaggccg aagcagagtg tgcaaaccgg gatgccaggc tggcgactgt    540
tggggaactt cacgcagctt ggaggaacgg ctttgaccag tgcgattacg gctggctgtc    600
ggatgccagc gtgcggcacc ctgtgactgt ggccagggcc cagtgtggag gtggtctact    660
tggggtgaga accctgtatc gttttgagaa ccagacatgc ttccctctcc ctgatagcag    720
atttgatgcc tactgcttta acgacctgct ctctgcaaa acaaacccat gcctcaatgg    780
aggcacctgc tatcctactg agacttccta tgtgtgcacc tgtgcacctg ctacagtgg    840
agaccagtgt gaactggatt ttgatgaatg tcactctaac ccttgtcgga atggagccac    900
ctgtgtggac ggtctgaata catttagatg cctctgcctt ccgagttatg tcggtgcact    960
ctgcgaacaa gacactgaga catgcgacta tggctggcac aaattccaag ggcaatgcta   1020
caagtacttt gctcatcgcc gtacatggga tgctgctgaa agggagtgtc gcctgcaggg   1080
tgcccacctc acaagcatcc tttctcatga ggaacaaatg tttgtgaatc gtgtgggcca   1140
tgattaccag tggattggcc tcaatgacaa gatgtttgaa catgacttcc gctggactga   1200
cggcagcgca ctgcaatatg agaactggag acccaaccag ccagacagct tcttttctgc   1260
tggagaagac tgcgttgtga tcatttggca tgagaatggc cagtggaatg acgtcccctg   1320
caactaccac ctcacctaca cctgcaagaa gggaacagtt gcttgcggcc aaccccctgt   1380
tgtagaaaat gccaagacct ttggaaagat gaaaccacgt tatgaaatca actccttgat   1440
tagataccac tgcaaagatg gtttcattca gcgtcacctt ccaactatcc ggtgcctagg   1500
aaatgggaga tggcaatgc ctaaaataac ctgcatgaac ccatctgcat accaaaggac   1560
ttattctaag aaatacttaa aaaattcctc atcagtcaag gacaattcta taaatacgtc   1620
aaaacatgag catcgctgga gccggaggtg gcaggaaacg aggcgctgat cctaaaatgg   1680
cgaacataag cttcattcat catttcagcc aaagccctgc ctttccgtgc ctttcctatc   1740
acctcaagga gaattagcag ttggtttgga ttttgggact gccgtctggt catttggggt   1800
ggctgtattc cta                                                      1813
```

<210> SEQ ID NO 25
<211> LENGTH: 456
<212> TYPE: PRT
<213> ORGANISM: Artificial Sequence
<220> FEATURE:
<223> OTHER INFORMATION: Engineered versican V-3-derived
      polypeptide having exons 3-4-5 deleted

<400> SEQUENCE: 25

```
Met Leu Ile Asn Met Asn Gly Ile Leu Trp Met Cys Ser Thr Leu Leu
  1               5                  10                  15

Leu Thr His Ala Leu His Lys Ala Lys Met Glu Glu Asn Pro Pro Val
             20                  25                  30

Lys Gly Ser Leu Ser Gly Lys Val Ile Val Tyr Cys Tyr Val Asp His
         35                  40                  45

Leu Asp Gly Asp Val Phe His Ile Thr Ala Pro Ser Lys Phe Thr Phe
     50                  55                  60

Glu Glu Ala Glu Ala Glu Cys Ala Asn Arg Asp Ala Arg Leu Ala Thr
 65                  70                  75                  80

Val Gly Glu Leu His Ala Ala Trp Arg Asn Gly Phe Asp Gln Cys Asp
                 85                  90                  95

Tyr Gly Trp Leu Ser Asp Ala Ser Val Arg His Pro Val Thr Val Ala
```

```
            100                 105                 110
Arg Ala Gln Cys Gly Gly Gly Leu Leu Gly Val Arg Thr Leu Tyr Arg
            115                 120                 125

Phe Glu Asn Gln Thr Cys Phe Pro Leu Pro Asp Ser Arg Phe Asp Ala
            130                 135                 140

Tyr Cys Phe Lys Arg Pro Asp Leu Cys Lys Thr Asn Pro Cys Leu Asn
145                 150                 155                 160

Gly Gly Thr Cys Tyr Pro Thr Glu Thr Ser Tyr Val Cys Thr Cys Ala
                165                 170                 175

Pro Gly Tyr Ser Gly Asp Gln Cys Glu Leu Asp Phe Asp Glu Cys His
            180                 185                 190

Ser Asn Pro Cys Arg Asn Gly Ala Thr Cys Val Asp Gly Leu Asn Thr
            195                 200                 205

Phe Arg Cys Leu Cys Leu Pro Ser Tyr Val Gly Ala Leu Cys Glu Gln
            210                 215                 220

Asp Thr Glu Thr Cys Asp Tyr Gly Trp His Lys Phe Gln Gly Gln Cys
225                 230                 235                 240

Tyr Lys Tyr Phe Ala His Arg Arg Thr Trp Asp Ala Ala Glu Arg Glu
                245                 250                 255

Cys Arg Leu Gln Gly Ala His Leu Thr Ser Ile Leu Ser His Glu Glu
            260                 265                 270

Gln Met Phe Val Asn Arg Val Gly His Asp Tyr Gln Trp Ile Gly Leu
            275                 280                 285

Asn Asp Lys Met Phe Glu His Asp Phe Arg Trp Thr Asp Gly Ser Ala
            290                 295                 300

Leu Gln Tyr Glu Asn Trp Arg Pro Asn Gln Pro Asp Ser Phe Phe Ser
305                 310                 315                 320

Ala Gly Glu Asp Cys Val Val Ile Ile Trp His Glu Asn Gly Gln Trp
                325                 330                 335

Asn Asp Val Pro Cys Asn Tyr His Leu Thr Tyr Thr Cys Lys Lys Gly
            340                 345                 350

Thr Val Ala Cys Gly Gln Pro Pro Val Val Glu Asn Ala Lys Thr Phe
            355                 360                 365

Gly Lys Met Lys Pro Arg Tyr Glu Ile Asn Ser Leu Ile Arg Tyr His
            370                 375                 380

Cys Lys Asp Gly Phe Ile Gln Arg His Leu Pro Thr Ile Arg Cys Leu
385                 390                 395                 400

Gly Asn Gly Arg Trp Ala Met Pro Lys Ile Thr Cys Met Asn Pro Ser
                405                 410                 415

Ala Tyr Gln Arg Thr Tyr Ser Lys Lys Tyr Leu Lys Asn Ser Ser Ser
            420                 425                 430

Val Lys Asp Asn Ser Ile Asn Thr Ser Lys His Glu His Arg Trp Ser
            435                 440                 445

Arg Arg Trp Gln Glu Thr Arg Arg
            450                 455

<210> SEQ ID NO 26
<211> LENGTH: 655
<212> TYPE: PRT
<213> ORGANISM: Rattus norvegicus

<400> SEQUENCE: 26

Met Leu Ile Asn Met Asn Gly Ile Leu Trp Met Cys Ser Thr Leu Leu
1               5                   10                  15

Leu Thr His Ala Leu His Lys Ala Lys Met Glu Glu Asn Pro Pro Val
```

-continued

```
                    20                  25                  30
Lys Gly Ser Leu Ser Gly Lys Val Ile Leu Pro Cys His Phe Ser Thr
                35                  40                  45
Leu Pro Thr Leu Pro Pro Asp Tyr Asn Thr Ser Glu Phe Leu Arg Ile
 50                  55                  60
Lys Trp Ser Lys Ile Glu Val Asp Lys Asn Gly Lys Asp Ile Lys Glu
 65                  70                  75                  80
Thr Thr Val Leu Val Ala Gln Asp Gly Asn Ile Lys Ile Gly Gln Asp
                 85                  90                  95
Tyr Lys Gly Arg Val Ser Val Pro Thr His Pro Asp Asp Val Gly Asp
                100                 105                 110
Ala Ser Leu Thr Met Val Lys Leu Arg Ala Ser Asp Ala Gly Val Tyr
                115                 120                 125
Arg Cys Asp Val Met Tyr Gly Ile Glu Asp Thr Gln Asn Thr Met Ser
                130                 135                 140
Leu Ala Val Asp Gly Val Val Phe His Tyr Arg Ala Ala Thr Ser Arg
145                 150                 155                 160
Tyr Thr Leu Asn Phe Glu Ser Ala Gln Gln Ala Cys Leu Asp Ile Gly
                165                 170                 175
Ala Val Ile Ala Thr Pro Glu Gln Leu Phe Ala Ala Tyr Glu Asp Gly
                180                 185                 190
Phe Glu Gln Cys Asp Ala Gly Trp Leu Ser Asp Gln Thr Val Arg Tyr
                195                 200                 205
Pro Ile Arg Ala Pro Arg Glu Gly Cys Tyr Gly Asp Met Met Gly Lys
                210                 215                 220
Glu Gly Val Arg Thr Tyr Gly Phe Arg Ser Pro Gln Glu Thr Tyr Asp
225                 230                 235                 240
Val Tyr Cys Tyr Val Asp His Leu Asp Gly Asp Val Phe His Ile Thr
                245                 250                 255
Ala Pro Ser Lys Phe Thr Phe Glu Glu Ala Glu Ala Cys Ala Asn
                260                 265                 270
Arg Asp Ala Arg Leu Ala Thr Val Gly Glu Leu His Ala Ala Trp Arg
                275                 280                 285
Asn Gly Phe Asp Gln Cys Asp Tyr Gly Trp Leu Ser Asp Ala Ser Val
                290                 295                 300
Arg His Pro Val Thr Val Ala Arg Ala Gln Cys Gly Gly Gly Leu Leu
305                 310                 315                 320
Gly Val Arg Thr Leu Tyr Arg Phe Glu Asn Gln Thr Cys Phe Pro Leu
                325                 330                 335
Pro Asp Ser Arg Phe Asp Ala Tyr Cys Phe Lys Arg Pro Asp Leu Cys
                340                 345                 350
Lys Thr Asn Pro Cys Leu Asn Gly Gly Thr Cys Tyr Pro Thr Glu Thr
                355                 360                 365
Ser Tyr Val Cys Thr Cys Ala Pro Gly Tyr Ser Gly Asp Gln Cys Glu
                370                 375                 380
Leu Asp Phe Asp Glu Cys His Ser Asn Pro Cys Arg Asn Gly Ala Thr
385                 390                 395                 400
Cys Val Asp Gly Leu Asn Thr Phe Arg Cys Leu Cys Leu Pro Ser Tyr
                405                 410                 415
Val Gly Ala Leu Cys Glu Gln Asp Thr Glu Thr Cys Asp Tyr Gly Trp
                420                 425                 430
His Lys Phe Gln Gly Gln Cys Tyr Lys Tyr Phe Ala His Arg Arg Thr
                435                 440                 445
```

-continued

```
Trp Asp Ala Glu Arg Glu Cys Arg Leu Gln Gly Ala His Leu Thr
450                 455                 460

Ser Ile Leu Ser His Glu Gln Met Phe Val Asn Arg Val Gly His
465                 470                 475                 480

Asp Tyr Gln Trp Ile Gly Leu Asn Asp Lys Met Phe Glu His Asp Phe
                    485                 490                 495

Arg Trp Thr Asp Gly Ser Ala Leu Gln Tyr Glu Asn Trp Arg Pro Asn
                500                 505                 510

Gln Pro Asp Ser Phe Phe Ser Ala Gly Glu Asp Cys Val Val Ile Ile
                515                 520                 525

Trp His Glu Asn Gly Gln Trp Asn Asp Val Pro Cys Asn Tyr His Leu
530                 535                 540

Thr Tyr Thr Cys Lys Lys Gly Thr Val Ala Cys Gly Gln Pro Pro Val
545                 550                 555                 560

Val Glu Asn Ala Lys Thr Phe Gly Lys Met Lys Pro Arg Tyr Glu Ile
                565                 570                 575

Asn Ser Leu Ile Arg Tyr His Cys Lys Asp Gly Phe Ile Gln Arg His
                580                 585                 590

Leu Pro Thr Ile Arg Cys Leu Gly Asn Gly Arg Trp Ala Met Pro Lys
                595                 600                 605

Ile Thr Cys Met Asn Pro Ser Ala Tyr Gln Arg Thr Tyr Ser Lys Lys
610                 615                 620

Tyr Leu Lys Asn Ser Ser Val Lys Asp Asn Ser Ile Asn Thr Ser
625                 630                 635                 640

Lys His Glu His Arg Trp Ser Arg Arg Trp Gln Glu Thr Arg Arg
                645                 650                 655

<210> SEQ ID NO 27
<211> LENGTH: 655
<212> TYPE: PRT
<213> ORGANISM: Rattus norvegicus

<400> SEQUENCE: 27

Met Leu Ile Asn Met Asn Gly Ile Leu Trp Met Cys Ser Thr Leu Leu
1               5                   10                  15

Leu Thr His Ala Leu His Lys Ala Lys Met Glu Glu Asn Pro Pro Val
                20                  25                  30

Lys Gly Ser Leu Ser Gly Lys Val Ile Leu Pro Cys His Phe Ser Thr
                35                  40                  45

Leu Pro Thr Leu Pro Pro Asp Tyr Asn Thr Ser Glu Phe Leu Arg Ile
                50                  55                  60

Lys Trp Ser Lys Ile Glu Val Asp Lys Asn Gly Lys Asp Ile Lys Glu
65                  70                  75                  80

Thr Thr Val Leu Val Ala Gln Asp Gly Asn Ile Lys Ile Gly Gln Asp
                85                  90                  95

Tyr Lys Gly Arg Val Ser Val Pro Thr His Pro Asp Asp Val Gly Asp
                100                 105                 110

Ala Ser Leu Thr Met Val Lys Leu Arg Ala Ser Asp Ala Gly Val Tyr
                115                 120                 125

Arg Cys Asp Val Met Tyr Gly Ile Glu Asp Thr Gln Asn Thr Met Ser
                130                 135                 140

Leu Ala Val Asp Gly Val Val Phe His Tyr Arg Ala Ala Thr Ser Arg
145                 150                 155                 160

Tyr Thr Leu Asn Phe Glu Ser Ala Gln Gln Ala Cys Leu Asp Ile Gly
                165                 170                 175
```

-continued

```
Ala Val Ile Ala Thr Pro Glu Gln Leu Phe Ala Ala Tyr Glu Asp Gly
            180                 185                 190

Phe Glu Gln Cys Asp Ala Gly Trp Leu Ser Asp Gln Thr Val Arg Tyr
        195                 200                 205

Pro Ile Arg Ala Pro Arg Glu Gly Cys Tyr Gly Asp Met Met Gly Lys
    210                 215                 220

Glu Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Ile Thr
                245                 250                 255

Ala Pro Ser Lys Phe Thr Phe Glu Glu Ala Glu Ala Cys Ala Asn
            260                 265                 270

Arg Asp Ala Arg Leu Ala Thr Val Gly Glu Leu His Ala Ala Trp Arg
    275                 280                 285

Asn Gly Phe Asp Gln Cys Asp Tyr Gly Trp Leu Ser Asp Ala Ser Val
290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Cys Phe Pro Leu
                325                 330                 335

Pro Asp Ser Arg Phe Asp Ala Tyr Cys Phe Lys Arg Pro Asp Leu Cys
            340                 345                 350

Lys Thr Asn Pro Cys Leu Asn Gly Gly Thr Cys Tyr Pro Thr Glu Thr
        355                 360                 365

Ser Tyr Val Cys Thr Cys Ala Pro Gly Tyr Ser Gly Asp Gln Cys Glu
    370                 375                 380

Leu Asp Phe Asp Glu Cys His Ser Asn Pro Cys Arg Asn Gly Ala Thr
385                 390                 395                 400

Cys Val Asp Gly Leu Asn Thr Phe Arg Cys Leu Cys Leu Pro Ser Tyr
                405                 410                 415

Val Gly Ala Leu Cys Glu Gln Asp Thr Glu Thr Cys Asp Tyr Gly Trp
            420                 425                 430

His Lys Phe Gln Gly Gln Cys Tyr Lys Tyr Phe Ala His Arg Arg Thr
        435                 440                 445

Trp Asp Ala Ala Glu Arg Glu Cys Arg Leu Gln Gly Ala His Leu Thr
    450                 455                 460

Ser Ile Leu Ser His Glu Glu Gln Met Phe Val Asn Arg Val Gly His
465                 470                 475                 480

Asp Tyr Gln Trp Ile Gly Leu Asn Asp Lys Met Phe Glu His Asp Phe
                485                 490                 495

Arg Trp Thr Asp Gly Ser Ala Leu Gln Tyr Glu Asn Trp Arg Pro Asn
            500                 505                 510

Gln Pro Asp Ser Phe Phe Ser Ala Gly Glu Asp Cys Val Val Ile Ile
        515                 520                 525

Trp His Glu Asn Gly Gln Trp Asn Asp Val Pro Cys Asn Tyr His Leu
    530                 535                 540

Thr Tyr Thr Cys Lys Lys Gly Thr Val Ala Cys Gly Gln Pro Pro Val
545                 550                 555                 560

Val Glu Asn Ala Lys Thr Phe Gly Lys Met Lys Pro Arg Tyr Glu Ile
                565                 570                 575

Asn Ser Leu Ile Arg Tyr His Cys Lys Asp Gly Phe Ile Gln Arg His
            580                 585                 590

Leu Pro Thr Ile Arg Cys Leu Gly Asn Gly Arg Trp Ala Met Pro Lys
        595                 600                 605
```

```
Ile Thr Cys Met Asn Leu Ser Ala Tyr Gln Arg Thr Tyr Ser Lys Lys
        610                 615                 620

Tyr Leu Lys Asn Ser Ser Val Lys Asp Asn Ser Ile Asn Thr Ser
625                 630                 635                 640

Lys His Glu His Arg Trp Ser Arg Arg Trp Gln Glu Thr Arg Arg
                645                 650                 655

<210> SEQ ID NO 28
<211> LENGTH: 74
<212> TYPE: PRT
<213> ORGANISM: Bos taurus

<400> SEQUENCE: 28

Val Val Phe His Tyr Arg Ala Ala Thr Ser Arg Tyr Thr Leu Asn Phe
1               5                   10                  15

Glu Met Ala Gln Lys Ala Cys Val Asp Ile Gly Ala Val Ile Ala Thr
            20                  25                  30

Pro Glu Gln Leu His Ala Ala Tyr Glu Asp Gly Phe Glu Gln Cys Asp
        35                  40                  45

Ala Gly Trp Leu Ser Asp Gln Thr Val Arg Tyr Pro Ile Arg Val Pro
    50                  55                  60

Arg Glu Gly Cys Tyr Gly Asp Met Met Gly
65                  70

<210> SEQ ID NO 29
<211> LENGTH: 74
<212> TYPE: PRT
<213> ORGANISM: Gallus gallus

<400> SEQUENCE: 29

Val Val Phe His Tyr Arg Ala Ala Thr Ser Arg Tyr Thr Leu Asn Phe
1               5                   10                  15

Thr Gln Ala Gln Gln Thr Cys Leu Asp Asn Gly Ala Val Ile Ala Ser
            20                  25                  30

Pro Glu Gln Leu Lys Ala Ala Tyr Glu Asp Gly Phe Glu Gln Cys Asp
        35                  40                  45

Ala Gly Trp Leu Ser Asp Gln Thr Val Arg Tyr Pro Ile Arg His Pro
    50                  55                  60

Arg Ile Gly Cys Phe Gly Asp Lys Met Gly
65                  70

<210> SEQ ID NO 30
<211> LENGTH: 74
<212> TYPE: PRT
<213> ORGANISM: Homo sapiens

<400> SEQUENCE: 30

Val Val Phe His Tyr Arg Ala Ala Thr Ser Arg Tyr Thr Leu Asn Phe
1               5                   10                  15

Glu Ala Ala Gln Lys Ala Cys Leu Asp Val Gly Ala Val Ile Ala Thr
            20                  25                  30

Pro Glu Gln Leu Phe Ala Ala Tyr Glu Asp Gly Phe Glu Gln Cys Asp
        35                  40                  45

Ala Gly Trp Leu Ala Asp Gln Thr Val Arg Tyr Pro Ile Arg Ala Pro
    50                  55                  60

Arg Val Gly Cys Tyr Gly Asp Lys Met Gly
65                  70
```

```
<210> SEQ ID NO 31
<211> LENGTH: 74
<212> TYPE: PRT
<213> ORGANISM: Mus musculus

<400> SEQUENCE: 31

Val Val Phe His Tyr Arg Ala Ala Thr Ser Arg Tyr Thr Leu Asn Phe
1               5                   10                  15

Ala Ala Ala Gln Gln Ala Cys Leu Asp Ile Gly Ala Val Ile Ala Ser
            20                  25                  30

Pro Glu Gln Leu Phe Ala Ala Tyr Glu Asp Gly Phe Glu Gln Cys Asp
        35                  40                  45

Ala Gly Trp Leu Ser Asp Gln Thr Val Arg Tyr Pro Ile Arg Ala Pro
    50                  55                  60

Arg Glu Gly Cys Tyr Gly Asp Met Met Gly
65                  70

<210> SEQ ID NO 32
<211> LENGTH: 74
<212> TYPE: PRT
<213> ORGANISM: Rattus norvegicus

<400> SEQUENCE: 32

Val Val Phe His Tyr Arg Ala Ala Thr Ser Arg Tyr Thr Leu Asn Phe
1               5                   10                  15

Glu Ser Ala Gln Gln Ala Cys Leu Asp Ile Gly Ala Val Ile Ala Thr
            20                  25                  30

Pro Glu Gln Leu Phe Ala Ala Tyr Glu Asp Gly Phe Glu Gln Cys Asp
        35                  40                  45

Ala Gly Trp Leu Ser Asp Gln Thr Val Arg Tyr Pro Ile Arg Ala Pro
    50                  55                  60

Arg Glu Gly Cys Tyr Gly Asp Met Met Gly
65                  70

<210> SEQ ID NO 33
<211> LENGTH: 74
<212> TYPE: PRT
<213> ORGANISM: Homo sapiens

<400> SEQUENCE: 33

Val Val Phe His Tyr Arg Ser Ala Arg Asp Arg Tyr Ala Leu Thr Phe
1               5                   10                  15

Ala Glu Ala Gln Glu Ala Cys Arg Leu Ser Ser Ala Ile Ile Ala Ala
            20                  25                  30

Pro Arg His Leu Gln Ala Ala Phe Glu Asp Gly Phe Asp Asn Cys Asp
        35                  40                  45

Ala Gly Trp Leu Ser Asp Arg Thr Val Arg Tyr Pro Ile Thr Gln Ser
    50                  55                  60

Arg Pro Gly Cys Tyr Gly Asp Arg Ser Ser
65                  70

<210> SEQ ID NO 34
<211> LENGTH: 74
<212> TYPE: PRT
<213> ORGANISM: Mus musculus

<400> SEQUENCE: 34

Val Val Phe His Tyr Arg Ala Ala Arg Asp Arg Tyr Ala Leu Thr Phe
1               5                   10                  15

Ala Glu Ala Gln Glu Ala Cys Arg Leu Ser Ser Ala Thr Ile Ala Ala
```

```
                    20                  25                  30
Pro Arg His Leu Gln Ala Ala Phe Glu Asp Gly Phe Asp Asn Cys Asp
            35                  40                  45

Ala Gly Trp Leu Ser Asp Arg Thr Val Arg Tyr Pro Ile Thr Gln Ser
        50                  55                  60

Arg Pro Gly Cys Tyr Gly Asp Arg Ser Ser
65                  70

<210> SEQ ID NO 35
<211> LENGTH: 74
<212> TYPE: PRT
<213> ORGANISM: Pan troglodytus

<400> SEQUENCE: 35

Val Val Phe His Tyr Arg Ser Ala Arg Asp Arg Tyr Ala Leu Thr Phe
1               5                   10                  15

Ala Glu Ala Gln Glu Ala Cys Arg Leu Ser Ser Ala Ile Ile Ala Ala
            20                  25                  30

Pro Arg His Leu Gln Ala Ala Phe Glu Asp Gly Phe Asp Asn Cys Asp
            35                  40                  45

Ala Gly Trp Leu Ser Asp Arg Thr Val Arg Tyr Pro Ile Thr Gln Ser
        50                  55                  60

Arg Pro Gly Cys Tyr Gly Asp Arg Ser Ser
65                  70

<210> SEQ ID NO 36
<211> LENGTH: 74
<212> TYPE: PRT
<213> ORGANISM: Rattus norvegicus

<400> SEQUENCE: 36

Val Val Phe His Tyr Arg Ala Ala Arg Asp Arg Tyr Ala Leu Thr Phe
1               5                   10                  15

Ala Glu Ala Gln Glu Ala Cys His Leu Ser Ser Ala Thr Ile Ala Ala
            20                  25                  30

Pro Arg His Leu Gln Ala Ala Phe Glu Asp Gly Phe Asp Asn Cys Asp
            35                  40                  45

Ala Gly Trp Leu Ser Asp Arg Thr Val Arg Tyr Pro Ile Thr Gln Ser
        50                  55                  60

Arg Pro Gly Cys Tyr Gly Asp Arg Ser Ser
65                  70

<210> SEQ ID NO 37
<211> LENGTH: 368
<212> TYPE: PRT
<213> ORGANISM: Artificial Sequence
<220> FEATURE:
<223> OTHER INFORMATION: Mutant human biglycan polypeptide
<220> FEATURE:
<221> NAME/KEY: VARIANT
<222> LOCATION: 42, 47
<223> OTHER INFORMATION: Xaa = Any Amino Acid other than Serine

<400> SEQUENCE: 37

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Xaa Gly Ala Asp Thr Xaa Gly
            35                  40                  45
```

```
Val Leu Asp Pro Asp Ser Val Thr Pro Thr Tyr Ser Ala Met Cys Pro
 50                  55                  60

Phe Gly Cys His Cys His Leu Arg Val Val Gln Cys Ser Asp Leu Gly
 65                  70                  75                  80

Leu Lys Ser Val Pro Lys Glu Ile Ser Pro Asp Thr Thr Leu Leu Asp
                 85                  90                  95

Leu Gln Asn Asn Asp Ile Ser Glu Leu Arg Lys Asp Asp Phe Lys Gly
                100                 105                 110

Leu Gln His Leu Tyr Ala Leu Val Leu Asn Asn Lys Ile Ser Lys
                115                 120                 125

Ile His Glu Lys Ala Phe Ser Pro Leu Arg Lys Leu Gln Lys Leu Tyr
        130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                    165                 170                 175

Gly Val Phe Ser Gly Leu Arg Asn Met Asn Cys Ile Glu Met Gly Gly
                180                 185                 190

Asn Pro Leu Glu Asn Ser Gly Phe Glu Pro Gly Ala Phe Asp Gly Leu
                195                 200                 205

Lys Leu Asn Tyr Leu Arg Ile Ser Glu Ala Lys Leu Thr Gly Ile Pro
                210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                    245                 250                 255

Arg Leu Gly Leu Gly His Asn Gln Ile Arg Met Ile Glu Asn Gly Ser
                260                 265                 270

Leu Ser Phe Leu Pro Thr Leu Arg Glu Leu His Leu Asp Asn Asn Lys
                275                 280                 285

Leu Ala Arg Val Pro Ser Gly Leu Pro Asp Leu Lys Leu Leu Gln Val
                290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                    325                 330                 335

Leu Phe Asn Asn Pro Val Pro Tyr Trp Glu Val Gln Pro Ala Thr Phe
                340                 345                 350

Arg Cys Val Thr Asp Arg Leu Ala Ile Gln Phe Gly Asn Tyr Lys Lys
                355                 360                 365

<210> SEQ ID NO 38
<211> LENGTH: 97
<212> TYPE: PRT
<213> ORGANISM: Rattus norvegicus

<400> SEQUENCE: 38

Asp Val Phe His Ile Thr Ala Pro Ser Lys Phe Thr Phe Glu Glu Ala
 1                   5                  10                  15

Glu Ala Glu Cys Ala Asn Arg Asp Ala Arg Leu Ala Thr Val Gly Glu
                 20                  25                  30

Leu His Ala Ala Trp Arg Asn Gly Phe Asp Gln Cys Asp Tyr Gly Trp
                 35                  40                  45

Leu Ser Asp Ala Ser Val Arg His Pro Val Thr Val Ala Arg Ala Gln
 50                  55                  60
```

```
Cys Gly Gly Gly Leu Leu Gly Val Arg Thr Leu Tyr Arg Phe Glu Asn
 65                  70                  75                  80

Gln Thr Cys Phe Pro Leu Pro Asp Ser Arg Phe Asp Ala Tyr Cys Phe
                 85                  90                  95

Lys

<210> SEQ ID NO 39
<211> LENGTH: 97
<212> TYPE: PRT
<213> ORGANISM: Homo sapiens

<400> SEQUENCE: 39

Asp Val Phe His Leu Thr Val Pro Ser Lys Phe Thr Phe Glu Glu Ala
  1               5                  10                  15

Ala Lys Glu Cys Glu Asn Gln Asp Ala Arg Leu Ala Thr Val Gly Glu
                 20                  25                  30

Leu Gln Ala Ala Trp Arg Asn Gly Phe Asp Gln Cys Asp Tyr Gly Trp
             35                  40                  45

Leu Ser Asp Ala Ser Val Arg His Pro Val Thr Val Ala Arg Ala Gln
 50                  55                  60

Cys Gly Gly Gly Leu Leu Gly Val Arg Thr Leu Tyr Arg Phe Glu Asn
 65                  70                  75                  80

Gln Thr Gly Phe Pro Pro Pro Asp Ser Arg Phe Asp Ala Tyr Cys Phe
                 85                  90                  95

Lys

<210> SEQ ID NO 40
<211> LENGTH: 97
<212> TYPE: PRT
<213> ORGANISM: Mus musculus

<400> SEQUENCE: 40

Asp Val Phe His Ile Thr Ala Pro Ser Lys Phe Thr Phe Glu Glu Ala
  1               5                  10                  15

Glu Ala Glu Cys Thr Ser Arg Asp Ala Arg Leu Ala Thr Val Gly Glu
                 20                  25                  30

Leu Gln Ala Ala Trp Arg Asn Gly Phe Asp Gln Cys Asp Tyr Gly Trp
             35                  40                  45

Leu Ser Asp Ala Ser Val Arg His Pro Val Thr Val Ala Arg Ala Gln
 50                  55                  60

Cys Gly Gly Gly Leu Leu Gly Val Arg Thr Leu Tyr Arg Phe Glu Asn
 65                  70                  75                  80

Gln Thr Cys Phe Pro Leu Pro Asp Ser Arg Phe Asp Ala Tyr Cys Phe
                 85                  90                  95

Lys

<210> SEQ ID NO 41
<211> LENGTH: 97
<212> TYPE: PRT
<213> ORGANISM: Bos taurus

<400> SEQUENCE: 41

Asp Val Phe His Ile Thr Ala Pro Asn Lys Phe Thr Phe Glu Glu Ala
  1               5                  10                  15

Gly Glu Glu Cys Lys Thr Gln Asp Ala Arg Leu Ala Thr Val Gly Glu
                 20                  25                  30

Leu Gln Ala Ala Trp Arg Asn Gly Phe Asp Arg Cys Asp Tyr Gly Trp
             35                  40                  45
```

-continued

```
Leu Leu Asp Ala Ser Val Arg His Pro Val Thr Val Ala Arg Ala Gln
     50                  55                  60

Cys Gly Gly Gly Leu Leu Gly Val Arg Thr Leu Tyr Arg Phe Glu Asn
 65              70                  75                      80

Gln Thr Gly Phe Pro Thr Pro Asp Ser Arg Phe Asp Ala Tyr Cys Phe
                 85                  90                  95

Lys
```